(12) United States Patent
Asano et al.

(10) Patent No.: US 9,708,639 B2
(45) Date of Patent: Jul. 18, 2017

(54) METHOD FOR QUANTIFYING AMINO ACIDS WITH PYROPHOSPHATE

(71) Applicants: Yasuhisa Asano, Toyama (JP); Masafumi Kameya, Toyama (JP)

(72) Inventors: Yasuhisa Asano, Toyama (JP); Masafumi Kameya, Toyama (JP)

(73) Assignees: TOYAMA PREFECTURE, Toyama (JP); AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/453,189

(22) Filed: Aug. 6, 2014

(65) Prior Publication Data

US 2014/0357524 A1    Dec. 4, 2014

Related U.S. Application Data

(63) Continuation of application No. PCT/JP2013/053146, filed on Feb. 8, 2013.

(30) Foreign Application Priority Data

| Feb. 9, 2012 | (JP) | 2012-026534 |
| Mar. 26, 2012 | (JP) | 2012-069625 |

(51) Int. Cl.
| G01N 33/68 | (2006.01) |
| C12Q 1/48 | (2006.01) |
| C12Q 1/25 | (2006.01) |
| C12Q 1/32 | (2006.01) |
| C12Q 1/34 | (2006.01) |

(52) U.S. Cl.
CPC .............. *C12Q 1/485* (2013.01); *C12Q 1/25* (2013.01); *C12Q 1/32* (2013.01); *C12Q 1/34* (2013.01); *C12Q 1/48* (2013.01); *G01N 33/6812* (2013.01); *G01N 33/6815* (2013.01)

(58) Field of Classification Search
None
See application file for complete search history.

(56) References Cited

U.S. PATENT DOCUMENTS

| 6,846,638 B2 * | 1/2005 | Shipwash | B01L 3/5027 |
| | | | 435/287.1 |
| 8,961,960 B2 * | 2/2015 | Chiang | C07K 16/40 |
| | | | 424/94.5 |
| 2006/0269915 A1 * | 11/2006 | Yukimasa | C12Q 1/42 |
| | | | 435/6.12 |
| 2008/0132586 A1 * | 6/2008 | Droux | C12Q 1/18 |
| | | | 514/789 |
| 2013/0052679 A1 | 2/2013 | Asano et al. | |
| 2013/0344526 A1 | 12/2013 | Asano et al. | |

FOREIGN PATENT DOCUMENTS

| JP | 60-246362 A | 12/1985 |
| JP | 61012300 A | 1/1986 |
| JP | 08-336399 A | 12/1996 |
| JP | 2001-017198 A | 1/2001 |
| JP | 2001-252095 A | 9/2001 |
| JP | 2003-174900 A | 6/2003 |
| JP | 2006-166709 A | 6/2006 |
| JP | 2006-187251 A | 7/2006 |
| JP | 2007-501019 A | 1/2007 |
| JP | 2007-097471 A | 4/2007 |
| JP | 2008-086312 A | 4/2008 |
| JP | 2008-523791 A | 7/2008 |
| JP | 2009-225784 A | 10/2009 |
| JP | 2010-200656 | * 9/2010 |
| JP | 2010-200656 A | 9/2010 |
| JP | 2011-050357 A | 3/2011 |
| WO | WO2005/003750 A1 | 1/2005 |
| WO | WO2005/070014 A2 | 8/2005 |

(Continued)

OTHER PUBLICATIONS

Research of psychosomatic disorders, Ministry of Health and Welfare, 1993, "Research on evaluation method of mass screening system", pp. 237-240 (1993).
Boyde, T.R. & Rahmatullah M. (1980), Optimization of conditions for the colorimetric determination of citrulline, using diacetylmonoxime, Anal. Biochem., 107, 424-431.
Baldwin, A.N. & Berg, P. (1966), Transfer ribonucleic acid-induced hydrolysis of valyladenylate bound to isoleucyl ribonucleic acid synthetase, J. Biol. Chem., 241, 839-845.
Forbes, C.D., Myung, J., Szewczak, A.A. & Landro, J.A. (2007), A high-throughput competitive scintillation proximity aminoacyl-tRNA synthetase charging assay to measure amino acid concentration, Anal. Biochem., 363, 246-254.
Masafumi Kameya et al., Japan Society for Bioscience, Biotechonology, and Agrochemistry Taikai Koen Yoshishu, Mar. 5, 2012.

(Continued)

*Primary Examiner* — Ralph Gitomer
(74) *Attorney, Agent, or Firm* — Shelly Guest Cermak; Cermak Nakajima & McGowan LLP

(57) ABSTRACT

There is provided a method for quantifying a subject substance, of which typical examples are amino acids. The method of the present invention comprises the following steps: the step of allowing an enzyme that can generate pyrophosphate by using adenosine triphosphate (ATP) as a substrate with converting the subject substance to act on the subject substance to generate pyrophosphate; the step of allowing pyruvate pyrophosphate dikinase (PPDK) to act on the generated pyrophosphate in the presence of adenosine monophosphate (AMP) and phosphoenolpyruvate (PEP) to generate ATP, phosphoric acid, and pyruvate; and the step of quantifying the generated pyruvate, and amount of the subject substance is determined on the basis of the obtained amount of pyruvate. According to the present invention, an amino acid in a biological sample containing a lot of various kinds of contaminants such as inorganic phosphoric acid and urea can be conveniently and quickly quantified without being influenced by the contaminants.

8 Claims, 11 Drawing Sheets

(56) References Cited

FOREIGN PATENT DOCUMENTS

WO  WO2005/070014 A3  8/2005
WO  WO2006/030620 A1  3/2006

OTHER PUBLICATIONS

Hahn, G.A. et al., Biochimica Et Biophysica Acta, 1967, vol. 146, pp. 259-263.
International Search Report and Search Opinion issued in PCT/JP2013/053146 (May 7, 2013).
Japanese version of International Preliminary Report on Patentability of Chapter I (Aug. 12, 2014) with English language translation.
Official Action issued in the corresponding Japanese application No. 2012-026534 on Dec. 11, 2012 with its English excerpt.
Abstract III of the 92nd Spring Annual Conference (2012), The Chemical Society of Japan, Mar. 9, 2012, p. 1069, 1PC-128.
Abstract III of the 90th Spring Annual Conference (2010), The Chemical Society of Japan, 2010, p. 1017, 3PC-170.
Official Action issued in the corresponding Japanese application No. 2012-069625 on Dec. 25, 2012 with its English excerpt.
Zhao Wuling, Prokaryotic Protein Synthesis, Molecular Biology, China Agricultural University Press, 2010, pp. 311-315.
Wang Jingyan, Zhu Shenggeng & Xu Changfa, Biochemistry (ver. 3), 2002, pp. 524-526.
Official Action issued in the corresponding Chinese application No. 201380008746.0 on May 22, 2015 with its English translation.
Office Action from Chinese Patent App. No. 201380008746.0 (Jan. 25, 2016) with English translation thereof.
Decision on Rejection for Chinese Patent App. No. 201380008746.0 (Oct. 27, 2016) with English language translation thereof.

* cited by examiner

Pyrophosphate Calibration Curve for the Case of Using Lactate Dehydrogenase
(For Measurement with Absorptiometer)

Pyrophosphate Calibration Curve for the Case of Using Lactate Dehydrogenase
(for Measurement with Microplate Reader)

Pyrophosphate Calibration Curve
for the Case of using Pyruvate Oxidase and Color Developing Dye Pyrophosphate Calibration Curve
for the Case of using Pyruvate Oxidase and Fluorescent Dye Pyrophosphate Calibration Curves
created with Reaction Mixtures containing Phosphoric Acid or ATP Test performed by adding Pyrophosphate to Biological Sample Methionine Calibration Curve Citrulline Calibration Curve

SEQUENCE LISTING

```
<160> NUMBER OF SEQ ID NOS: 39

<210> SEQ ID NO 1
<211> LENGTH: 2658
<212> TYPE: DNA
<213> ORGANISM: Propionibacterium freudenreichii subsp. shermanii
      NBRC12426
<220> FEATURE:
<223> OTHER INFORMATION: Inventor: ASANO, Yasuhisa
      Inventor: KAMEYA, Masafumi

<400> SEQUENCE: 1
gtgagcgaga agtacatcta cgatctgtcc gagggcgatg cctcgatgaa gtccttgctg     60
ggtggcaagg gtgccggtgt agccgagatg atgcgtctgg gcgtaccggt gcccgatggc    120
tttacggtca ccacgcaggc ctgcatcgag acgatgaaca atggcggcac ctggcccgca    180
ggccttcgcg atcagatctc tgacgcgctc gcccgcttcg aggagcgtgc cggacgcaag    240
ctcggcgcgt ccgagaagcc gctgctggtg tcggtgcgtt cgggtgccgt cgtgtcgatg    300
cccggcatga tggacaccat cctcaacctg ggtatctccg acgagtcggt ggccgccgtg    360
gccgccgagg ccaacaatga gcgcttcgcc tgggactgtt accgccgctt catccagatg    420
tacggcgagg tcgtcgaggg cctcgacgcg cacatctacg aggacgccct gactgccatg    480
aagcagcgca agggtgcctc gcaggacacc gacctgaccg ccgaggacct caaggaactc    540
accacggagt tcaagcagat cagcgatgac gcgttgggcg gcgcctggcc ctccgacccg    600
cgtgagcagt tgatgcgcgc cgtcgaggcc gtgttcaaca gctggcagaa cccgcgcgcc    660
aaggtctacc gcaaggcgaa ccatatctcc gacgacctgg gcaccgcggt gaacgtgatg    720
cagatggtct tcggcaaccg cggcgagacc tccgccaccg tgtctgcttc acccgcaac    780 ccctccaccg gtgagaacgc gctgtacggc gagttcctca ccaacgcgca gggcgaggac    840
gtggtggccg gcatccgcac cccgcgtccc ctgatcgaga tgaaggaggt gctgccgcag    900
gcgtacggcg agctggtcga caccatgcac aagatggaga cccactaccg cgacatgcag    960
gacatggagt tcaccgtcga gaacggcaag ctctacatgc tgcagacgcg taacggcaag   1020
cgcaccgccg ccgctgcgtt gaaggttgcc tccgacctgg tggacgaggg cctcatcgac   1080
aaggaagagg ccgtgcgccg catcgagccc gaccagctcg atcagctgct gcacccggcc   1140
atcgatcccg gccagagcgc cacgccgatc accaagggcc tgccggccag ccccggcgcg   1200
gccgtgggtg ccgcggtgtt cgacgccgat accgccgctg agcgcggcga ggccggtgag   1260
ccggtggtgt tgatccgctt cgagaccacc cctgatgaca tccatggcgt gctgcaggca   1320
cagggcgtgc tcaccgccca tggcggcatg accagccacg cggccgtggt ggcccgcggc   1380
ttcggcaagc cctgcgtggc aggcgccacc gacatcaaga tcgacaccga ggccaagacg   1440
atgaccgtcg gcggcgtcac ggtgcacgag ggcgacacgc tgaccctcaa cggctccacc   1500
ggcgaggtgt tcaacacggc gctgaagctg attccgccgc gtctcaacga ggacttcctc   1560
aaggtggtcg gttgggccga cgagatccgc gacctgggcg tggaggccaa cgccgacaac   1620
```

```
ggcaccgacg ccgccaaggc ccgtgagttg ggtgccgagg gcatcggcct gtgccgcacc      1680
gagcacatgt tcttcggtga cgaccggctg ccggccatgc acgagatgat cctgtcggag      1740
aacgacgagc agcgtcaggt ggcgctcgac aagatcttgc cgatgcagca gagcgacttc      1800
gaggcgatct tcaccgccat gaagggcctg ccggtgacgg tgcgcctgct cgatccgccg      1860
ctgcacgagt tcatgcccga cctggtgacc caggcgctga aggtgcagga tggagctc       1920 aagggcgccg atccgaccaa gctggccgag gagcgtcgca cgctcgcgca ggtgaagaag      1980
ctgcacgagc agaacccgat gttgggcacc cgcggttgcc gcctcggcat gctctacccg      2040
cagattcccg acatgcaggc ccgtgccatc gcgcgtgccg cgttggccgt gctcgaccgc      2100
gagggcgaga cggttgacct gcagatcatg gtgccgttgg tgcacctgcg ccaggagctg      2160
cagcgtcagc gcgagatcgt ggtggctgcg gtggacgacg agctcgacaa ggccggccag      2220
aagctcgact acctggtggg cacgatgatc gagctgccga gggccgcctt ggtggccgat      2280
cagatcgcgc aggaggctga tttcttcagc ttcggcacca acgacctgac gcagaccacg      2340
ctgggcatca gccgcgatga cgccgagaac ggcttcctcg gttggtacga ggcgcagggc      2400
gtggtgaagc gtgacccgtt cgccacgatc gacgtggatg cgtcggcca gctggtgcgc       2460 atgggcaccg agaagggccg ggccgccaat ccgaagctgt cggtgggcgt ctgcggtgag      2520
cacggtgggg atcccgactc gatcgcgttc ttccagtcgg tgggccttga ctatgtgtcg      2580
tgctcgccgt tccgcgtgcc gatcgcccgg ttcgccgcgg cgaaggccaa gctcgcccag      2640
gcggatgcaa gcaagtaa                                                    2658

<210> SEQ ID NO 2
<211> LENGTH: 27
<212> TYPE: DNA
<213> ORGANISM: Artificial Sequence
<220> FEATURE:
<223> OTHER INFORMATION: PCR primer

<400> SEQUENCE: 2
tatacatatg agcgagaagt acatcta                                            27

<210> SEQ ID NO 3
<211> LENGTH: 34
<212> TYPE: DNA
<213> ORGANISM: Artificial Sequence
<220> FEATURE:
<223> OTHER INFORMATION: PCR primer

<400> SEQUENCE: 3
tatactcgag ttacttactt gcttgcatcc gcct                                    34

<210> SEQ ID NO 4
<211> LENGTH: 2748
<212> TYPE: DNA
<213> ORGANISM: Thermoproteus tenax NBRC100435

<400> SEQUENCE: 4
atgcctaaaa agtacgtctt cgatttcgat gaagccgact atcgaaataa gaggctcttc       60
ggcggcaagg gcgccagctt ggtacagatg gcgcaactgg gcctcagagt gccgccgggc      120
tttataataa caactgaggc gtgtaaagac ttcttcgggc ccaagaggga ggagatagcg      180
gagctcgagg cacaattagc cagacagccg ccgccggatg tcagagatgc gcttatcaca      240
aagttgttct caataataga tagcttagat ctgccacagg gactgtggga ggaggtcgtg      300
```

-continued

```
gagcatatga agaggctaga ggacagaaca ggccgtagat tcggcgatcc gaagaatccc      360
ttgttggtct ccgtgagatc cggcgcggct gtgtcgatgc ctggcatgat ggacacagtg      420
ctcaacctcg gcctaaacga tgagaccgtt aaaggcctcg ccgaacagac caacaacgag      480
tggttcgcct acgatgcata tagacgcttt attaatatgt tcggaagaat tgtattaaat      540
atagatgata aactattctc aaaagcatgg gatgatatta gaggaaata tggcgtaaag      600 gaggatccgc agatgccgat cgagggccta aggaggcag ttgaaatatt taagaagata      660
gtggcagaga gccgcggagc cttcccgcaa gacccttggg agcagttgaa gttggccata      720
aaggctgtgt ttcgatcttg gatagccca agggctatct tctatagaat cgccgaaaag      780
ataacaagcg atatcgccga ctgcaccgct gtgaatgtag tcactatggt gttcggcaac      840
atgggctggg acagcggaac aggcgtcgtc ttctcgaggg acgtggccac tggagagaac      900
aggctatatg gagagtttct ccctgtggct cagggagagg acgttgtggc agggataagg      960 accccccatgg atatagacga attcaagaag aggtttccac atttatga agagttatat     1020 aatggtgtta agttattaga aaaagtaaat aaagatgtac aagacgtaga gttcactgta     1080
gagcgcggga gactctactt cctgcagtgt cgcaacgcca aaatgactcc catggcgagg     1140
gtcaagacgg ccgttgatat ggccaaagag ggcataataa ctaaggatga ggctctgatg     1200
aaggtctctc cagagcatgt cctccagctc ctttatccgc gcatcgatcc taaggcaaac     1260
gcgaggccca tcgccaaagg actgcccgcg agccctggcg ccgtctcggg gcaattagtg     1320
ttcaatccgg acgatgccgt aaagtgggcc cgcgatggaa aaaaggttgt gctcgccaga     1380
gttgagacaa agcccgacga cgtccacggc ttttacgcgg ccgtgggcat tttgaccaca     1440 agaggggta tgacctcaca cgcggctgtt gtcgctagag ctataggcaa acctgccgtt     1500
gtcggagcgg aggacgctgt tgtggatgaa cagaacaagg tgttgagagc gggcggccta     1560
atattgaagg aggggggactg ggtgactatc gatggaaaca caggccttgt atatccaggt     1620
gtggtcccaa cgttggagcc agagctgata cctgagctag aggagctgtt gaggtgggcc     1680
gacgaagtga ggaggctcgg cgttagggcc aacgccgatc ttccagagga tgccgccata     1740
gccagaaagt tcggcgcaga ggggatagggt tgttgagga tagagcggat gttcagaaag     1800
cctgagcgcc tcgacctcct tcgtcggata attttggcag aaaatagaga ggagagaata     1860
aaacatctgg aacagctcta taggatgtta aaggaggatt tcaaggcgat cttcgaaata     1920
atggatggat tgcccgtagt agtaaggctc atagatcctc cgctccacga gttcctgccg     1980
aagccggagg aggtgcttca acagatatgc gaggggagga tgtcaggtaa agatgtgtcc     2040
tcattggaga ggctgtacaa tagattgaag gccctgcagg aggccaaccc tatgttgggc     2100
catagaggtg tgcgcgtggg ggtgagctac cccgaggtct actattattt tgaccaaggct     2160 atcgcggagg ccgcctcaga gctcaagaaa gagggccgca acccggtcgt agagataatg     2220
atacctcagg tgagcgacgt aagggagatt aaatatgtaa aggaaaaggg aataatgccg     2280
gcgctgaggg atgtggagga gagctccgga gttaagttag atatcaagat aggcactatg     2340
atagagactg tgcgcgctgc gctcaccgta gagaaaatag cgcgagaggt cgacttcatc     2400
agcttcggca aaacgatct cacgcaggcc gtgtttagct tcagcagaga cgacgcagag     2460
aacaagttta taccgcaata cctcgacctc aagatactcg acgcagatcc tttcgagacg     2520
ttggatccag agggtgtggc taagctggtc gagcaggctt ccaggtcggc caaggaggct     2580
aacccggcca ttgaggttgg ggtctgcggc gaacacggcg gcgagccgaa gtccatatcg     2640
ctcttcagca gaatgaagat agattacgtc agcgcctcgc cgtttagggt tcctctggct     2700
```
agacttgcgg ccgctcaagc ggctatcgca agctccaaac gtgagtag     2748

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
tatagctagc atgcctaaaa agtacgtctt     30

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
tataaagctt ctactcacgt ttggagcttg     30

<210> SEQ ID NO 7
<211> LENGTH: 1155
<212> TYPE: DNA
<213> ORGANISM: Escherichia coli W3110

<400> SEQUENCE: 7
atggcaaaac accttttttac gtccgagtcc gtctctgaag ggcatcctga caaaattgct     60
gaccaaattt ctgatgccgt tttagacgcg atcctcgaac aggatccgaa agcacgcgtt     120
gcttgcgaaa cctacgtaaa aaccggcatg gttttagttg gcggcgaaat caccaccagc     180
gcctgggtag acatcgaaga gatcacccgt aacaccgttc gcgaaattgg ctatgtgcat     240
tccgacatgg gctttgacgc taactcctgt gcggttctga gcgctatcgg caaacagtct     300
cctgacatca accagggcgt tgaccgtgcc gatccgctgg aacagggcgc gggtgaccag     360
ggtctgatgt ttggctacgc aactaatgaa accgacgtgc tgatgccagc acctatcacc     420
tatgcacacc gtctggtaca gcgtcaggct gaagtgcgta aaaacggcac tctgccgtgg     480
ctgcgcccgg acgcgaaaag ccaggtgact tttcagtatg acgacggcaa aatcgttggt     540
atcgatgctg tcgtgctttc cactcagcac tctgaagaga tcgaccagaa atcgctgcaa     600
gaagcggtaa tggaagagat catcaagcca attctgcccg ctgaatggct gacttctgcc     660
accaaattct tcatcaaccc gaccggtcgt ttcgttatcg gtggcccaat gggtgactgc     720
ggtctgactg gtcgtaaaat tatcgttgat acctacggcg gcatggcgcg tcacggtggc     780
ggtgcattct ctggtaaaga tccatcaaaa gtggaccgtt ccgcagccta cgcagcacgt     840
tatgtcgcga aaaacatcgt tgctgctggc ctggccgatc gttgtgaaat tcaggtttcc     900
tacgcaatcg cgtggctga accgacctcc atcatggtag aaactttcgg tactgagaaa     960
gtgccttctg aacaactgac cctgctggta cgtgagttct tcgacctgcg cccatacggt     1020
ctgattcaga tgctggatct gctgcacccg atctacaaag aaaccgcagc atacggtcac     1080
tttggtcgtg aacatttccc gtgggaaaaa accgacaaag cgcagctgct gcgcgatgct     1140
gccggtctga agtaa     1155

<210> SEQ ID NO 8
<211> LENGTH: 35
<212> TYPE: DNA

```
<213> ORGANISM: Artificial Sequence
<220> FEATURE:
<223> OTHER INFORMATION: PCR primer

<400> SEQUENCE: 8
aaactgcagc atatggcaaa acaccttttt acgtc                              35

<210> SEQ ID NO 9
<211> LENGTH: 26
<212> TYPE: DNA
<213> ORGANISM: Artificial Sequence
<220> FEATURE:
<223> OTHER INFORMATION: PCR primer

<400> SEQUENCE: 9
aagaattctt acttcagacc ggcagc                                        26

<210> SEQ ID NO 10
<211> LENGTH: 1344
<212> TYPE: DNA
<213> ORGANISM: E. coli W3110

<400> SEQUENCE: 10
atgacgacga ttctcaagca tctcccggta ggtcaacgta ttggtatcgc tttttctggc     60
ggtctggaca ccagtgccgc actgctgtgg atgcgacaaa agggagcggt tccttatgca    120
tatactgcaa acctgggcca gccagacgaa gaggattatg atgcgatccc tcgtcgtgcc    180
atggaatacg gcgcggagaa cgcacgtctg atcgactgcc gcaaacaact ggtggccgaa    240
ggtattgccg ctattcagtg tggcgcattt cataacacca ccggcggcct gacctatttc    300
aacacgacgc cgctgggccg cgccgtgact ggtaccatgc tggttgctgc gatgaaagaa    360
gatggcgtga atatctgggg tgacggtagc acctacaaag aaacgatat cgaacgtttc    420 tatcgttatg gtctgctgac caatgctgaa ctgcagattt acaaaccgtg gcttgatact    480
gactttattg atgaactggg cggccgtcat gagatgtctg aatttatgat tgcctgcggt    540
ttcgactaca aaatgtctgt cgaaaaagcc tactccacag actccaacat gcttggtgca    600
acgcatgaag cgaaggatct ggaatacctc aactccagcg tcaaaatcgt caacccgatt    660
atgggcgtga attctgggga tgagagcgtg aagatcccgg cagaagaagt cacagtacgc    720
tttgaacaag gtcatccggt ggcgctgaac ggtaaaacct ttagcgacga cgtagaaatg    780
atgctggaag ctaaccgcat cggcggtcgt cacggcctgg gcatgagcga ccagattgaa    840
aaccgtatca tcgaagcgaa aagccgtggt atttacgaag ctccggggat ggcactgctg    900
cacattgcgt atgaacgcct gttgaccggt attcacaacg aagacaccat tgagcagtat    960
cacgcgcatg tcgtcagtt gggccgtctg ctgtaccagg ggcgttggtt tgactcccag   1020
gcgctgatgc tgcgtgactc tctgcaacgc tgggttgcca gccagatcac tggtgaagtt   1080
accctggagc tgcgccgtgg gaacgattat tcaatcctga ataccgtctc agagaacctg   1140
acctacaagc cagagcgtct gacgatggaa aaaggcgact cggtgttctc gccagatgat   1200
cgtattggtc aattgaccat gcgtaacctg gatatcactg atacccgcga gaaacttttc   1260
ggttatgcca aaactggcct gctttcctcc tctgccgctt caggcgtgcc gcaggtggag   1320
aatctggaaa acaaaggcca gtaa                                         1344

<210> SEQ ID NO 11
<211> LENGTH: 32
<212> TYPE: DNA
<213> ORGANISM: Artificial Sequence
```

<220> FEATURE:
<223> OTHER INFORMATION: PCR primer

<400> SEQUENCE: 11
aaggatccat atgacgacga ttctcaagca tc                                    32

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12
aaaaagctta ctggcctttg ttttccag                                         28

<210> SEQ ID NO 13
<211> LENGTH: 1257
<212> TYPE: DNA
<213> ORGANISM: Pseudomonas aeruginosa PAO1

<400> SEQUENCE: 13
atgagcacgg aaaaaaccaa acttggcgtc cactccgaag ccggcaaact gcgcaaagtg      60
atggtctgct cgcccggact cgcccaccag cgcctgaccc cgagcaactg cgacgagttg     120
ctgttcgacg acgtgatctg ggtgaaccag gccaagcgcg accacttcga cttcgtcacc     180
aagatgcgcg agcgcggcat cgacgtcctc gagatgcaca atctgctgac cgagaccatc     240
cagaacccgg aagcgctgaa gtggatcctc gatcgcaaga tcaccgccga cagcgtcggc     300
ctgggcctga ccagcgagct cgcgctcctg gctggagagcc tggagccgcg caagctggcc     360
gagtacctga tcggcggcgt cgccgctgac gacctgcccg ccagcgaagg cgccaacatc     420
ctcaagatgt accgcgagta cctgggccat tccagcttcc tgctgccgcc gttgccgaac     480
acccagttca cccgcgacac cacttgctgg atctacggcg gcgtgaccct gaacccgatg     540
tactggccgg cgcgacgaca ggaaaccctg ctgaccaccg ccatctacaa gttccacccc     600
gagttcgcca acgccgagtt cgagatctgg tacggcgacc cggacaagga ccacggctcc     660
tcgaccctgg aaggcggcga cgtgatgccg atcggcaacg gcgtggtcct gatcggcatg     720
ggcgagcgct cctcgcgcca ggccatcggt caggtcgccc agtcgctgtt cgccaagggc     780
gccgccgagc gggtgatcgt cgccggcctg ccgaagtccc cgcgccgcgat gcacctggac     840 accgtgttca gcttctgcga ccgcgacctg gtcacggtct cccggaagt ggtcaaggaa     900 atcgtgccct tcagcctgcg ccccgatccg agcagcccct acggcatgaa catccgccgc     960
gaggagaaaa ccttcctcga agtggtcgcc gaatccctcg gcctgaagaa actgcgcgtg    1020
gtcgagaccg gcggcaacag cttcgccgcc gagcgcgagc aatgggacga cggtaacaac    1080
gtggtctgcc tggagccggg cgtggtggtc ggctacgacc gcaacaccta caccaacacc    1140
ctgctgcgca aggccggcgt cgaggtcatc accatcagcg ccagcgaact gggtcgcggt    1200
cgcggcggcg gccactgcat gacctgcccg atcgtccgcg acccgatcga ctactga       1257

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
aaactgcagc atatgagcac ggaaaaaacc aaac                         34

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
aagaattcag tagtcgatcg ggtc                                   24

<210> SEQ ID NO 16
<211> LENGTH: 1383
<212> TYPE: DNA
<213> ORGANISM: Thermotoga maritima
<220> FEATURE:
<223> OTHER INFORMATION: Inventor: ASANO, Yasuhisa
        Inventor: KAMEYA, Masafumi

<400> SEQUENCE: 16
atgagaataa ccaacaccct gacaggaaaa aagaagaat ttgtgcctat caacccggt      60 gttgtgagga tgtacgtgtg cggacccacc gtgtacgatc tcatccacgt ggggaacgcg   120
agacccgcgt tggtattcga tgtgttcagg aggtacctcg agtacagggg ttacagggtc   180
ataatggttc agaattcac ggatatagac gacaagatca taaacaaggc gaatcagctc    240
ggtgtcgatt acaagaccgt ggcagatacc ttcatagccg agtactggag agacgcacat   300
gcgcttggta taagaccggc gaattttcat ccaagaacca ccgatttcgt tgaagacatt   360
gttgagataa tagaaaaact cgtagaaaaa gggttcgcgt atcaaacgga aacgggtgtc   420
tatttcgatg tgagaaagtt cgaaaagtac ggtgaactct ccaaaaagaa gatagaggat   480
ctcatcgcgg gtgccagagt cgaggtggac gaaacgaaga agtctcctct cgatttctcg   540
ctctggaaaa aggccaaacc cggtgaaccc tgctggaagt cccccctggg agagggaaga   600
ccaggttggc acatagagtg tacggttatg tccgtgaaaa tcctgggaga gagtttcgat   660
atacacgcgg gtggagaaga tctcgtgttt ccgcaccacg agaacgagaa ggctcaggcc   720
gaagccctga ccggtaaggt ttttgcgaga tactggatgc acaacggcat ggtcaggttc   780
ctcggtgata gatgagtaa atcgacggga acatcttca ccgtccgtga agccgtgaaa     840
agatacggca gagacggtct gagatacatg attctctcaa agcactacag gtcgccgatg   900
gacttctctg aagaactcct tcaggattac tccagggcgg tcaaacgtgt ttgggagatt   960
ctgggacgat acgaaaaatc tggagatatc gggatatacta agaaaacgc tgtttacgaa  1020 gagtacgtta tcgtttttgt ggaagctctc gacgacgatt tcaacacacc agtagcggtg  1080
tccttgattt ttgagctcgc aagaaacctc agcaaagcga tggatgacaa cgaccgtgag  1140
gatgcccttc tctactatca cctgatcaga agggagttcg gccccgttct gggactttc   1200 gatctcaacg aagagaagaa agaagtttcc tctgaagaac tgctcaaact gctgatagaa  1260
gtgagagatg tcttgaggaa ggaaaaaaga tacgatcttt ctgatcgaat aagggatcgc  1320
ctcagggaga ttggaatcat tttgaaggat accccttcgg ggacagaata cactgtcgag  1380
tga                                                                1383

<210> SEQ ID NO 17
<211> LENGTH: 1263
<212> TYPE: DNA
<213> ORGANISM: Thermotoga maritima

<400> SEQUENCE: 17

```
ttgaaataca gaaggataaa gggaacaaac gatatcttcg gtgaagagat atggtactgg      60
aggtacgtcg aggaaacctt cagaaatgtg tgcgaaagcg cgggaataga ggagatcaga     120
actcccatat tcgaacagac ggaacttttc gttagaagtg tgggagaaga atcagacatc     180
gttcagaaag agatgtacac cttccaggac aaagcgggaa ggagcatcac tctgagacca     240
gaaggtaccg cgcccgtcgt cagggctttt ctggagaatt ctctgataga taggggttt     300
caacagagat actactacat aggtcccatg ttccgatacg aaaaaccaca atcggggaga     360
ttgagacagt tccaccaggt gggtttcgag atcatcggcc ccgaatctcc aaaagcggat     420
ttcgaggtga tcatgctggt tgatacccttc ttgagaaggc tcggactcac gaaatacaag     480
attcacctga attccatagg ctgtccggtg tgcaggaaaa actatcgcga agccctcaag     540
gagtattacg gtcgaatcct ggacaatctc tgtgacgact gcaaaagacg ttacgagacg     600
aacattttga gactgctcga ttgcaaggtg gaccacgaat actctctgaa tgcaccaaaa     660
agcgtcgact atctctgtga ttcctgcagg gcacactaca agaagttgaa agagtacctc     720
aacactttcg agatcgaata cgtggaagat cacaccctgg tccgcgggct cgactactac     780
accagaacgg tttttgaggt gaggcacgaa ggtcttggag cccagagcgc catcgcgggt     840
ggtggaaggt acgatggcct ctttgcggag cttgggggct cttccgtacc cgcccttggt     900
tttgcaggtg gtatagagag aattatactc gctttaaaag cagagggaat agaaatcccg     960
atgaaaaatg ttcatcttgt ttacatcgca actcttggtg aaaaagcctt tatggatggt    1020
gttcggcttg cgggtgaatt gagaaagaaa ggcctgagtg tggatgtgga catcatggat    1080
agaaagctct ccgtcagct taagcacgcc agcagaatgg gatcgaggta tgcggtcatt    1140
attggtgatg aagaactgga aaaaggaatc gtcattctcc gcgacctcga gacgggagac    1200
caggttgaaa tcgatcggga cttcgccgct gactacatcg ctgaaagggt ttcaaaagat    1260
tga                                                                 1263
```

<210> SEQ ID NO 18
<211> LENGTH: 1509
<212> TYPE: DNA
<213> ORGANISM: Thermotoga maritima

<400> SEQUENCE: 18

```
gtgctgaaag agttcaaaga caacgactc aaagagatac aggaacttcg ttctatgggt      60
atagagccat atccttacaa attcgaaaag gaactcacgg ccagagaaat aagggaaaag     120
tacgactatc ttcaagctgg agaagttctt gaatctgaaa agctctcttt cgcagggaga     180
gtcatgtcga tacgtcacca cggaaagacg gccttctttc acatgaaaga tgacacgggc     240
cggatccagg cttacataaa agcagattct gttgggaagg aaaagatgga tctcttcaaa     300
agacacgtca aataggtga ctttgtagga gtaagaggct ttccgttcaa agcaaaaacc     360
ggagagttga ccatttacgt tcaagaatac acgcttctga gcaaggctct gcggcctctg     420
cccgagaagt ggcacggcat aaaagataag gaaatcatat acaggcagag gtacctcgaa     480
ctcatcgtga acgacgaggc tattgagagg ttcaaaaagc gattcaaggc cgtccgtgtg     540
atacgggaat ttctcaacag caggggattc atcgaagtgg aaacacctat tcttcattac     600
gtcacggggtg gtgcggaagc gaggcctttt gtgacccatc tcaacgtttt tgatatcgat     660
atgtatttga gaatcgcacc ggagctttac ctgaaaggt tgatcgtcgg cggttttgaa     720
aagatatacg agataggaaa gaacttcaga aacgaaggaa tatcttacaa acacagtccc     780
```

```
gagttcacca gcatagagat ctaccaggct tacgcggatt acaacgatat gatggatctc      840
actgaagagt tgatagtgga agttgtgaaa agaacatgtg gcaccttgaa aatctcctac      900
caaggcaagg agatagactt cacaccaccc tggaaaagag tgagaatgag agactttctc      960
aaagaaaaac tcggggtgga catcctcgaa gatcccgatg aagtgttgtt gaagaagctc     1020
gaagaacatg gggtagaact ggaaataaag aacagagcac acctcataga caaactcaga     1080
gatctggtgg aagaagagct ggtgaacccc accttcataa tcgatcatcc tgtggtgatt     1140
tcccctcttg ccaaaagaca ccgagaggat cctagactca cggaaaggtt cgaactcatc     1200
atattcggaa gagagatcgc gaacgcgttc agtgagctga acgatcccgt tgatcaatac     1260
cagagatttc tcgaacaggc gaaaatgaga gaagagggag atgaagaagc acacatgatg     1320
gatctcgatt ttgtgagggc cctcgagtat ggtatgcctc ccacgggagg actgggaatc     1380
ggtcttgaca ggctcttcat gttcatcacg gattccccca caataaggga tgtgattccc     1440
ttcccaattg tgaaacccaa aaagttcgag gaagaagagg cggaattcga aggagggttt     1500
gaagaatga                                                             1509

<210> SEQ ID NO 19
<211> LENGTH: 1734
<212> TYPE: DNA
<213> ORGANISM: Thermotoga maritima

<400> SEQUENCE: 19
ttgcggatga aagacctcta tgctcctact ctcaaagaaa ccccttccga tgttgagaca       60
gtaagccacg agtatcttct tcgaggaggc ttcataagaa aagtagccgc cggtatatac      120
acctacctcc cattaggaag aagagtgctt ctcaaaatag agaacatagt tcgagaagag      180
atgaacagga taggggcaca gggaaattct gatgcccatc cttcaacctgc ggaactctgg      240 aaacagtcag gaaggtggga cgattacggt cccgaaatga tgaaactcaa agacaggcac      300
gaaagagact tcacactcgg tcccacgcac gaggagatcg tcacggacct tgtgaagaac      360
gaacttcgtt catacaaaca gcttcctctc actctgtatc agatagcgaa caagtacaga      420
gacgaaatca gaccacgctt cggccttctc agggcgagag aattcatcat gaaggacgct      480
tacagctttc acgcaagctg ggaatctctg gacgagacgt acgaacagtt caaaaaagcg      540
tactcccgaa tcatggaaag gcttggtgtg cggtacatga tcatagaggc agaaacgggt      600
gccatcggag ggaacgcttc ccacgagttc gtcgttcctg cgaaaatagg agagacgaac      660
gtactcttct gtgaaaagtg cggctaccag gcaagcgacg aaaaagccga atacaaaggt      720
gaatacactc aggaacagga agaagagaaa cccctcaaga aggttcccac acccggggtg      780
aagacgatcg aggaagtttc agagtttctc ggtgttcctc cgtcgaagat tgtgaagtcc      840
cttctttaca aaggaagaga aggatacgta atggtactta agggggagac cctggagctc      900
aacgaagcga agctcaaagc acatttgaaa gatcagtcgc tgagaatggc aaccccagaa      960
gaaattctga aggacttcgg agttcccgtc ggattcattg gacccatcgg tgtggatgtg     1020
aagaaagtgg ccgatcacag cgtcagggga ctgaaaaact tcgtcgttgg gggtatggaa     1080
gaggatacgc actacgtaaa cgcaaaccac cccagagatt tcaaggtgga cgagtggtac     1140
gatctgagaa cggtggtgga gggtgatccc tgtcccgtct gtggtgagcc tctcaaggcg     1200
acaaaaggga tagagcttgg tcacatcttc aaactcggca caaaatactc cgaagccatg     1260
aaggcctact tcatggatga aaacggttga gatgaagcctt tcatcatggg ctgttatggc     1320
```

```
tggggagttt ccagaacgat ggcggctgtt gtggaacatt tccacgatga gaacggtatg    1380
atctggcccc tttcgatcgc cccttacacc gttgtggtgg acattctgaa catgaacgac    1440
gctgaacaga agcaggtggg tgagaagatt taccaggttc tctcagaaaa aggagaagag    1500
gttgttctgg atgacagaga agtctcgcct ggtttcaaat tcaaagacgc cgatctcata    1560
ggctttccca taagaataaa cgtgggaaga tccctcaagg aaggtgttgt tgaactgaag    1620
aaacgctatt cgaaagaact cgtcaaggtg aacatcaaaa acggtttcgg tgcgcttctg    1680
gagacactgg aaaagatgaa gcgggagtac gatcccaagg aggctgtcag gtga          1734

<210> SEQ ID NO 20
<211> LENGTH: 1278
<212> TYPE: DNA
<213> ORGANISM: Thermotoga maritima

<400> SEQUENCE: 20
atgatagata taaagctcat cagacaaaat cccgatttcg tgaaggaagc cctcagaaag      60
cgaggagagg atcccgctat aatcgatgag atttttgaaga tcgacgccga ctggcgcgct    120
accatcacga aaaccaacga gctgagatcc agaagaaacg aaatttccaa aaatgtggca    180
aggttgaaaa aagaagggaa aaacgcagag gcagaggcac tcatcgagga agggaaaaga    240
ttaggagaag agataaaagc gttagaagaa aaagaaaaag aacttcagaa gaagttaaac    300
gatcttcttt tgatgattcc gaacatcccg catgagagtg tccccgttgg agaagacgaa    360
tctcagaacg ttgaagtgag aaggtgggga gagccgagag aattcgactt cacccccgctc   420 gctcactggg acctcggacc tgcgtggggg ctcatggatt tcagcagggc gtccaagctc    480
agcggttcca gattcaccgt tatgtatgga aaactcgcaa gactcgagag ggctctgata    540
aacttcatgc ttgacgttca tacaaaggaa cacggttaca cggaagtgtg ggttccacac    600
ctggtgaaaa gagaaaccat caccataacc ggacagctcc ccaaattcga agaagagctt    660
tatcttgctg agagggatga cctgttcctc attccgacgg ctgaggttcc cctcgcagcg    720
cttcacagtg gagagatcct cgaagagaaa gaactaccaa agaaatacgt ctcttacact    780
ccctgttacc gcagagaagc gggaagttac gggaaagacg tgaggggggat gatcaggcag    840 catcaattcg acaaggtcga gctcgtctgg gtgaccacac cggaaagatc cttcgaagat    900
cttgaagagc ttgtgaaaga cgccgaaacc attcttagaa aattggagct ccccttacaga   960 gtcgtttcgc tctgtacggg agatctcgga ttcacctccg cgaaaaccta cgatatagaa   1020
gtgtggcttc cttcctacaa cgcatacaaa gagatatctt cctgcagtaa cgtgacggac   1080
tttcaggcga gaagaggaaa catgagatac agaaggagat cggatggaaa gctcgaatac   1140
gttcacacgt tgaacggatc gggtatcgcc gttgaaggg cactcgttgc gatactggaa   1200
aactaccagc aaccagacgg cagtgtgaga gtgccggagg tgctcgttcc ctacacaggg    1260
ttcgaggtga taccgtag                                                  1278

<210> SEQ ID NO 21
<211> LENGTH: 987
<212> TYPE: DNA
<213> ORGANISM: Thermotoga maritima

<400> SEQUENCE: 21
ttgagaatac tgagcggcat gagacctacc ggaaaactcc atataggtca tctcgtggga     60
gctctgaaaa actgggtgaa gcttcaggaa gaaggaaacg aatgtttcta ctttgtcgcg    120
gattggcacg cttttgacca ccactacgac gatgtttcga agctcaaaga atacacccgc    180
```

```
gacctggtga ggggatttct cgcctgtgga atagatcctg aaaagtccgt gattttgtt    240 cagtctggtg tcaaagagca cgctgagctt gcactgcttt tcagcatgat cgtttctgtt    300
tcacgtctcg agagggttcc cacttacaaa gagataaaaa gtgagctgaa ctacaaagat    360
cttttccacg ctggttttct catctatccc gttcttcagg cagccgatat tttgatctac    420
aaagctgaag gagtaccagt cggtgaagat caggtttacc acatagaact cacgagggag    480
atcgccaggc gttttaacta tctctacgat gaagtctttc cagaaccaga agcaattctg    540
tctcgggttc caaagcttcc aggaacggac ggccgaaaga tgagcaaaag ctatgggaac    600
ataataaacc tagaaatctc ggaaaaagaa ctggaacaga cgatactgag gatgatgacc    660
gatccagcga gggtgagaag gagcgaccct ggaaatccgg agaactgccc cgtatggaaa    720
taccaccagg cgttcgacat cagtgaagaa gagagcaaat gggtatggga aggctgtaca    780
acggccagca tcggctgtgt tgattgtaag aagttgctgt tgaagaatat gaaacgaaaa    840
ttggcaccga tctgggagaa cttcagaaaa atagacgaag atccacacta cgtggacgac    900
gttataatgg aagggacgaa gaaggccaga gaagtggctg ctaaaacgat ggaagaagtg    960
agaagggcca tgaacctgat gttctga                                        987

<210> SEQ ID NO 22
<211> LENGTH: 1206
<212> TYPE: DNA
<213> ORGANISM: Thermotoga maritima

<400> SEQUENCE: 22
atgacgccgg aggaacaggt gaaaattctc aaaagaaacg ttgttgacct cataagtgaa     60
gaagaactcc tcgacagaat aaaaagaaaa ggaaaactcc gcgtgaaact cggtgtggat    120
ccctcaaggc ccgatttgca tctgggtcac gcggtcgttc tgaggaagtt gagagaattt    180
caggatctcg gtcacacggt cgttctgatc ataggagact tcaccgcacg tattggtgat    240
ccctccggaa gaaacgaaac acgccccatg ctgaccaaag aagaggttct ggagaacgca    300
aagacctatc aggagcaggc cttcaaaata ctggatccca aaagaacgga acttcgcttc    360
aacggtgagt ggctcgacag gatgaccttc gcagatgtga tcattctggc ttcgaagtac    420
acggttgcga ggatgctcga gagagacgat ttcgcaaaga gattcaaaga aggcattccc    480
attgccatat cagagtttct gtatccgctc gcacaggcct acgattccgt tgccatccag    540
tcagatgtgg aactcggcgg aacggatcag cttttcaacc tccttgtggg aaggaagata    600
caggaagaat acggtcaaga gccccagatc gtcatgacga tgccgatcat cgagggaaca    660
gacggaaaat tgaagatgag caaaagctac ggaaactaca tcgctttcaa cgatccgccc    720
gaggagatgt acggcaaact catgtccata cctgatgaac tcatcataaa atacatgcgc    780
cttctcacgg acatcccaga gaacggatc gaagagtacg aaagaaagat gaaggaaaaa    840
acgatcaatc cacgagacgt gaagatggtt ctcgcgtacg agataacgcg cttcttccat    900
ggtgaagaaa acgcaaagaa ggcccaggaa cacttcgtga agtctttca aaagaaagaa    960 attcctgacg agatgccggt cgttgagatt tctcaggaga agaacatcgt ggatctcctc   1020
gtggagatag gagctgcatc cagcaaaagt gaggctaaaa gactcgtttc tcaaggtgga   1080
gtgtacatcg acggagagag gatagaggac ataaaattca ctgtagaacc tgatggagag   1140
cgagttttga gagttggaaa gaggaagttc tacagaatat caggtggaga gacaaaaaaa   1200
ctttag                                                              1206
```

<210> SEQ ID NO 23
<211> LENGTH: 31
<212> TYPE: DNA
<213> ORGANISM: Artificial Sequence
<220> FEATURE:
<223> OTHER INFORMATION: PCR primer CysRS F

<400> SEQUENCE: 23
tataccatgg catgagaata accaacaccc t                                    31

<210> SEQ ID NO 24
<211> LENGTH: 29
<212> TYPE: DNA
<213> ORGANISM: Artificial Sequence
<220> FEATURE:
<223> OTHER INFORMATION: PCR primer CysRS R

<400> SEQUENCE: 24
tatagcggcc gcctcgacag tgtattctg                                       29

<210> SEQ ID NO 25
<211> LENGTH: 32
<212> TYPE: DNA
<213> ORGANISM: Artificial Sequence
<220> FEATURE:
<223> OTHER INFORMATION: PCR primer HisRS F

<400> SEQUENCE: 25
tataccatgg gcttgaaata cagaaggata aa                                   32

<210> SEQ ID NO 26
<211> LENGTH: 32
<212> TYPE: DNA
<213> ORGANISM: Artificial Sequence
<220> FEATURE:
<223> OTHER INFORMATION: PCR primer HisRS R

<400> SEQUENCE: 26
tatagcggcc gcatcttttg aaacccttc ag                                    32

<210> SEQ ID NO 27
<211> LENGTH: 30
<212> TYPE: DNA
<213> ORGANISM: Artificial Sequence
<220> FEATURE:
<223> OTHER INFORMATION: PCR primer LysRS F

<400> SEQUENCE: 27
tataccatgg tgctgaaaga gttcaaagaa                                      30

<210> SEQ ID NO 28
<211> LENGTH: 32
<212> TYPE: DNA
<213> ORGANISM: Artificial Sequence
<220> FEATURE:
<223> OTHER INFORMATION: PCR primer LysRS R

<400> SEQUENCE: 28
tatagcggcc gcttcttcaa accctccttc ga                                   32

<210> SEQ ID NO 29
<211> LENGTH: 32
<212> TYPE: DNA
<213> ORGANISM: Artificial Sequence
<220> FEATURE:
<223> OTHER INFORMATION: PCR primer ProRS F

```
<400> SEQUENCE: 29
tataccatgg gcttgcggat gaaagacctc ta                              32

<210> SEQ ID NO 30
<211> LENGTH: 32
<212> TYPE: DNA
<213> ORGANISM: Artificial Sequence
<220> FEATURE:
<223> OTHER INFORMATION: PCR primer ProRS R

<400> SEQUENCE: 30
tatagcggcc gccctgacag cctccttggg at                              32

<210> SEQ ID NO 31
<211> LENGTH: 45
<212> TYPE: DNA
<213> ORGANISM: Artificial Sequence
<220> FEATURE:
<223> OTHER INFORMATION: PCR primer SerRS F

<400> SEQUENCE: 31
tataccatgg gcatagatat aaagctcatc agacaaaatc ccgat                45

<210> SEQ ID NO 32
<211> LENGTH: 42
<212> TYPE: DNA
<213> ORGANISM: Artificial Sequence
<220> FEATURE:
<223> OTHER INFORMATION: PCR primer SerRS R

<400> SEQUENCE: 32
tatagcggcc gccggtatca cctcgaaccc tgtgtaggga ac                   42

<210> SEQ ID NO 33
<211> LENGTH: 45
<212> TYPE: DNA
<213> ORGANISM: Artificial Sequence
<220> FEATURE:
<223> OTHER INFORMATION: PCR primer TrpRS F

<400> SEQUENCE: 33
tataccatgg gcatagatat aaagctcatc agacaaaatc ccgat                45

<210> SEQ ID NO 34
<211> LENGTH: 29
<212> TYPE: DNA
<213> ORGANISM: Artificial Sequence
<220> FEATURE:
<223> OTHER INFORMATION: PCR primer TrpRS R

<400> SEQUENCE: 34
tatagcggcc gcgaacatca ggttcatgg                                  29

<210> SEQ ID NO 35
<211> LENGTH: 31
<212> TYPE: DNA
<213> ORGANISM: Artificial Sequence
<220> FEATURE:
<223> OTHER INFORMATION: PCR primer TyrRS F

<400> SEQUENCE: 35
tataggatcc atgacgccgg aggaacaggt g                               31

<210> SEQ ID NO 36
```

```
<211> LENGTH: 36
<212> TYPE: DNA
<213> ORGANISM: Artificial Sequence
<220> FEATURE:
<223> OTHER INFORMATION: PCR primer TyrRS R

<400> SEQUENCE: 36
tataaagctt ctaaagtttt tttgtctctc cacctg                                    36

<210> SEQ ID NO 37
<211> LENGTH: 3132
<212> TYPE: DNA
<213> ORGANISM: Thermus thermophilus

<400> SEQUENCE: 37
atgttcaagg aggtcggcga gcccaacttt cccaagctgg aagaggaggt cttggccttc          60
tggaagcggg aaaagatctt ccaaaagagc gtggaaaacc gcaaaggcgg tcccccgctac        120 accgtctacg agggccctcc caccgccaac ggcctccccc acgtgggcca cgcccaggcc        180
cggagctaca aggacctctt ccccccgcta caagaccatg cggggctacta cgcgccccgg        240 agggcaggct gggacaccca cgggcttccc gtggagctgg aggtggagaa gaagctcggc        300
ctcaagagca agcgggagat tgaggcctac ggcattgagc gcttcaacca agcctgccgc        360
gagtccgtct tcacctacga aaggagtgg gaggccttta ccgagcgcat cgcctactgg        420
gtggacctgg agaacgccta cgccaccttg aacccacct atattgagag catctggtgg        480
agcctgaaga acctctttga ccggggcctc ctctaccggg accacaaggt ggtgccctac        540 tgccccccgct gcggcacccc cctctcctcc acgaggtcg ccctggggta caaggagatc        600
caagacccct cggtctacgt ccgcttcccc ttgaaggagc gaagaagct tggcctagag        660 aaggcgagcc tcctcatctg gaccaccacc ccctggaccc tgcccgggaa cgtggccgca        720
gcagtccacc cggagtacac ctacgccgcc ttccaggtgg agacgaggc cctgatcctg        780 gaggaggggc tggggaggaa gcttttggc gagggaaccc cggtcctcaa aaccttcccg        840
ggcaaggccc tggaaggcct ccctacacc cccccctacc ccaggccctt ggagaagggc        900
tacttcgtgg tcctcgccga ctacgtgagt caagaggacg ggacgggcat cgtccaccag        960
gcccccgcct tcggcgccga ggacctggag acggcgaggg tctacgggct tcccctcctg       1020
aagaccgtgg acgaggaggg gaagctcctc gtggagccgt taagggcct ctacttccgc       1080 gaggccaacc gggcgatcct aagggacctg aggggcggg gcctcctctt caaggaggaa       1140
agctacctcc acagctaccc ccactgctgg cggtgctcca cccccctcat gtactacgcc       1200
acggagagct ggttcatcaa aaacacccctc ttcaaggacg agctcatccg caagaaccag       1260
gagatccact gggtgccccc ccacatcaag gagggccgct acggggagtg gctcaagaac       1320
ctcgtggact gggccttaag ccgcaaccgc tactggggga caccccctccc catctgggtc       1380 tgccaggcgt gcggcaagga ggaggccatc gggagcttcc aggagctcaa ggcgagggcc       1440
acgaagcccc tccccgagcc ctttgacccc caccgccccct acgtgaccca ggtggagctc       1500
gcctgtgcct gcggcgggac catgcgccgc gtcccctacg tcattgacgt ctggtacgac       1560
tccggggcca tgcccttcgc ctccttgcac taccccttg agcacgaaga ggtgttccgg       1620
gagagcttcc ccgcggactt catcgccgag gggattgacc agacccgggg ctggttcaac       1680
tccctccacc agctcggggt gatgctcttc ggctccatcg ccttcaagaa cgtgatctgc       1740
cacgcctcca tcctggacga aaaggggcag aagatgtcca gtccaagggg aacgtggtg       1800 gacccctggg acatcatccg ggagttcggg gcggacgccc tcaggtggta catctacgtc       1860
```

```
tccgcgcctc ccgaggccga ccggcgcttc gggcccaacc tggttcggga acggtgcgg      1920 gactacttcc tcaccctctg gaacgtctac agcttcttcg tgacctacgc caacctggac     1980
cggcccgacc tcaagaaccc ccctccccc  gagaagcggc ccgagatgga ccgctggctc     2040
ctcgcccgca tgcaggacct catccagagg gtgacggagg ccctcgaggc ctacgacccc     2100
accacgagcg cccgcgccct gagggacttc gtggtggagg acctctccca gtggtacgtc     2160
cgcaggaacc ggcgccgctt ctggaagaac gaggacgccc tggaccggga ggcggcctac     2220
gccaccctct acgaggccct cgtcctggtg gccaccctcg ccgccccctt cacccccttc     2280
ctcgccgagg tcctgtggca gaacctggtg cggagcgtcc ggcccgaggc caaggagagc     2340
gtccacctcg ccgactggcc cgaggccgac ccggccctgg ccgacgaggc cctggtggcc     2400
cagatgcggg cggtgctcaa ggtggtggac ctggcccggg cggcccgggc gaaaagcggg     2460
gtcaagaccc gcacccccct tcccctcctc ctcgtcaccg ccccaccgc cttggagcgg      2520 gagggttaa  agcgcttcgc ccacgagatc gccgaggagc tcaacgtcaa ggaggtccgg     2580
gtcctggaac ccggggagga gatcctctcc tacagggtcc tgcccaacct caagctcctg     2640
gggaggaagt acggcaagct cgtccccaaa atccgggagg ccctgcaaag ggaaagggag    2700
cgcgccgccg ccttggcgct aagggcgag  gccatccccc tggaggtgga gggcgaggcc     2760
ctcaccctcc tcccggagga ggtcctcctc gaggccgagg cccccaaggg ctaccaggcc    2820
ctggagaagg acgggtacgt ggccgccctc aaggtggagg tcacggaagc cctccgcatg     2880
gagggcctcg cccgcgacct catccgcctc ctgcagcagg cccgcaaaga catgggcctc    2940
aaggtctcgg accggatccg ggtgggctac gaggcggagg gccctacct  cgaggccctg     3000 aagcggcacg ggccctggat cgccgaggag gtgctggcca ccgccttcgg ggaaggcctc    3060
ttcggcgggt ttgaggcccg ggtggaggac gaggagggca aggcggtctt ccacctggcc    3120
cgggcggagt ga                                                        3132
```

<210> SEQ ID NO 38
<211> LENGTH: 1857
<212> TYPE: DNA
<213> ORGANISM: Thermus thermophilus

<400> SEQUENCE: 38

```
atggaaaagg tcttctacgt gaccacccc  atctactacg tgaacgccga gccgcacctg       60
ggccacgcct acaccacggt ggtggcggac tttctggccc ggtggcaccg cctggacggc      120
taccgcacct tcttcctcac cggtaccgac gagcacgggg agacggtcta ccgggcggcc      180
caggcggcgg gagaggaccc caaggccttc gtggaccggg tctccgggcg cttcaaaagg      240
gcctgggacc tcctcggcat cgcctacgac gacttcatcc gcaccacgga ggaaaggcac      300
aagaaggtgg tgcagctcgt cctaaagaag gtctacgagg ccggggacat ctactacggg      360
gagtacgagg cctctactg  cgtctcctgc gagcgctttt acacggagaa ggagctcgtg      420 gagggcttt  gccccatcca cggaaggccc gtggaaaggc ggaaggaggg gaactacttc      480
ttccgcatgg agaagtaccg ccctggctc  caggagtaca tccaggaaaa tcccgacctc      540
atccgccccg agggctaccg gaacgaggtc ctggccatgc tcgccgagcc catcggggac      600
ctctccatct ccaggccaaa atcccgcgtc cctgggca   tcccctccc ctgggacgag      660 aaccacgtga cctacgtctg gtttgacgcc ctcctgaact acgtctccgc cctgactac       720 cccgaggggg aggcctaccg gaccttctgg ccccacgcct ggcacctcat cggcaaggac      780
```

```
atccttaagc cccacgccgt cttctggccc accatgctga aggcggcggg gatccccatg    840
taccgccacc tgaacgtggg agggttttg ctggggccgg acgggcgcaa gatgtccaag    900
accctgggga acgtggtgga ccccttcgcc cttctggaaa agtacggccg ggacgccctg    960
cgctattacc tccttaggga gatccnctac ggccaggaca ccccggtgag cgaggaggcc   1020
ctaaggaccc ggtacgaggc cgacctcgcc gacgacctgg gcaacctggt gcaaaggacc   1080
cgggccatgc tcttccgttt cgccgagggc cgcatccccg aacccgtggc ggggaggag    1140 ctcgccgagg ggacggggct tgccgggagg ctcaggcctt tggtgcggga gctcaagttc   1200
cacgtggccc tcgaggaggc catggcctac gtcaaggcct tgaaccgcta catcaacgag   1260
aagaagccct gggagctttt caagaaggag ccggaggagg cccgggccgt gctctaccgg   1320
gtggtggagg gcctgaggat cgcctccatc ctcctcaccc cggctatgcc cgacaagatg   1380
gcggagctca ggcgggccct ggggcttaag gaggaggtgc gcctcgagga ggccgagcgc   1440
tggggcctgg ccgagccccg ccccatcccc gaggaagccc ccgtcctttt ccccaaaaag   1500
gaggccaagg tggaggccaa gcccaaggaa gaggcctgga tcggcataga ggacttcgcc   1560
aaggtggagc tcaggtggc ggaggttttg gcggcggaga agcacccgaa cgccgaccgg   1620 ctttttggtcc tcaggctctc cctggggaac gaggagcgca ccgtggtctc ggggatcgcc   1680
aagtggtacc ggcccgagga gctcgtgggc aagaaggtgg tcctggtggc gaacctcaag   1740
cccgccaagc tccggggcat tgagagccag gggatgatcc tcgccgccca ggaggggag    1800 gccttggccc tggtgacggt ggagggggag gtgccgcccg ggcggtggt gaagtaa      1857
```

<210> SEQ ID NO 39
<211> LENGTH: 1299
<212> TYPE: DNA
<213> ORGANISM: Thermus thermophilus

<400> SEQUENCE: 39

```
atggcgggca ccggccacac cccggaagag gccctggccc tcctcaagcg ggggccgag     60 gagatcgtcc ccgaggaaga gcttctcgcc aagctcaagg aggggcggcc cctcacggtc    120
aagctcggag ccgaccccac gaggcccgac ctgcacctgg ccacgcggt ggtcctgagg    180 aagatgcgcc agttccagga gctcggccac aaggtggtcc tcatcatcgg cgacttcacc    240
gggatgatcg ggaccctttc gggccgttcc aagacccggc ccccctcac cctggaggag    300 acccgggaga acgccaagac ctacgtggcc caggcgggga gatcctcag gcaggagccc    360 cacctctttg agctccgcta caactccgag tggctggagg gcctcacctt caaggaggtg    420
gtgcgcctca cctccctcat gaccgtggcc cagatgctgg aaagggagga cttcaagaag    480
cggtacgagg cggggattcc catctcccctg cacgagcttt tgtacccctt cgcccaggcc    540
tacgactccg tggccataag ggccgacgtg gaaatgggg gcacggacca gcgcttcaac    600
ctcctggtgg ccgggaggt gcaacgggcc tacgggcaaa gccccaggt ctgcttcctc    660 atgccccttc tcgtgggcct tgacggcgg agaagatga gcaagagcct ggacaactac    720
atcggcctca ccgagccccc ggaggcgatg ttcaagaagc tcatgcgggt gccggaccct    780 ctcctccga gctacttccg gcttctcacg gacctggagg aggaggaaat agaggccctc    840
ctaaaggcgg gccccgtccc cgcccaccgg gtcctcgccc gcctcctcac gcgggcctac    900 gccctgccc agatccccc ccggatagac cgggccttt acgaaagcct cggctacgcc    960
tgggaggcct cgggcggga caaggaggcg ggccccgagg aggtaaggag ggcggaagcc   1020
cgctacgacg aggtggccaa aggggggaatc cccgaggaga tccccgaggt caccatcccc   1080
```

```
gcctcggagc tgaaggaagg ccggatctgg gtggcgaggc tttttacctt agcgggcctc    1140
accccctcca acgccgaggc gaggaggctc atccagaacc ggggcctgag gctggacggg    1200
gaggtcctca ccgaccccat gctccaggtg gacctctccc ggccccgcat cctgcagcgg    1260
ggcaaggacc gcttcgtgcg ggtgcggctt tcggactga                           1299
```

METHOD FOR QUANTIFYING AMINO ACIDS WITH PYROPHOSPHATE

CROSS REFERENCE OF THE RELATED APPLICATIONS

This application is a Continuation of, and claims priority under 35 U.S.C. §120 to, International Application No. PCT/JP2013/053146, filed Feb. 8, 2013, and claims priority therethrough under 35 U.S.C. §119 to Japanese Patent Application No. 2012-026534, filed on Feb. 9, 2012, and Japanese Patent Application No. 2012-069625, filed on Mar. 26, 2012, the entireties of which are incorporated by reference herein. Also, the Sequence Listing filed electronically herewith is hereby incorporated by reference (File name: 2014-08-06T_US-518_Seq_List; File size: 38 KB; Date recorded: Aug. 6, 2014).

BACKGROUND OF THE INVENTION

Field of the Invention

The present invention relates to a method for quantifying pyrophosphate by allowing a reaction of pyrophosphate with pyruvate pyrophosphate dikinase (PPDK), and quantifying the product pyruvate, which is suitable for a reaction system containing adenosine triphosphate (ATP) and inorganic phosphoric acid. The present invention also relates to a method for quantifying methionine, citrulline or arginine by allowing a reaction of methionine with adenosylmethionine synthetase (AdoMetS), citrulline with argininosuccinate synthetase (ASS), or arginine with arginine deiminase (ADI) and ASS, and measuring the generated pyrophosphate by the aforementioned method for quantifying pyrophosphate.

The present invention further relates to a method for measuring the amount of an amino acid in a sample, which includes the steps of reacting the amino acid in the presence of aminoacyl-tRNA synthetase (AARS) and an (aminoacyl-AMP)-AARS complex decomposition reagent, and quantifying the product.

The present invention is useful in the medical field, such as for screening of inborn metabolic abnormalities; in the biochemical field, such as analysis of protein hydrolysates; and in the food and cosmetic-related fields, such as for ingredient analyses of foods and cosmetics; and so forth.

Brief Description of the Related Art

Amino acids in biological samples such as blood can serve as markers for detection of various diseases, and the development of methods for quantifying these amino acids is strongly desired from the medical point of view. Furthermore, methods for quantifying an amino acid using an enzyme have superior characteristics, such as high selectivity and quick quantification under mild conditions, and therefore they are considered to be suitable for being applied to many samples at actual medical sites. In particular, it is known that methionine accumulates in homocystinuria patients at high concentration, and methionine serves as an important biomarker for clinical mass screening of such patients. Further, citrulline and arginine are metabolites in the urea cycle, and serve as a biomarker of metabolic abnormalities in the urea cycle including citrullinuria or arginase deficiencies. Simple and quick methods for quantifying these amino acids are also expected to be applied to mass screening for detection of such diseases as mentioned above.

Enzymatic quantification methods of methionine are known, including a method using methionine gamma lyase (Research of psychosomatic disorders, Ministry of Health and Welfare, 1993, "Research on evaluation method of mass screening system", pp. 237-240 (1993); hereinafter "Health and Welfare"), and a quantification method using a functionally modified phenylalanine dehydrogenase (Japanese Patent Unexamined Publication (Kokai) No. 2008-86312, Method for analyzing L-methionine in biological sample using functionally modified phenylalanine dehydrogenase; hereinafter "the '312 document") is known to be effective for the mass screening of homocystinuria. However, in the method using methionine gamma lyase, ammonia is also detected together with methionine. Ammonia is generally present in the blood at a concentration of 20 to 50 µM, which is a level equivalent to or higher than the blood Met concentration. Furthermore, since the blood ammonia level varies with exercise, protein intake, and so forth, the blood test based on the above method is greatly affected by ammonia. Furthermore, the methionine gamma lyase also shows reactivity with sulfur-containing amino acids such as cysteine and homocysteine, besides methionine. Therefore, using this quantification method, it is difficult to selectively quantify methionine in a sample containing these sulfur-containing amino acids. Furthermore, since the functionally modified phenylalanine dehydrogenase also shows reactivity with other branched chain amino acids other than methionine, a pretreatment for removing branched chain amino acids is required.

Methods for quantifying citrulline include reacting citrulline with diacetylmonoxime and detecting color development by the product (Boyde, T. R. & Rahmatullah M. (1980), Optimization of conditions for the colorimetric determination of citrulline, using diacetylmonoxime, Anal. Biochem., 107, 424-431; herein after "Boyde et al."). However, since urea and analogous compounds thereof also react like citrulline, it cannot be used for a biological sample containing a lot of urea. Furthermore, it also has other problems, for example, it requires the complicated operation of incubation under acidic and high temperature conditions, and since it is a stop reaction method, temporal citrulline production cannot be monitored. In addition, methods for quantifying citrulline using an enzyme are have not been previously reported.

Enzymatic methods for quantifying arginine include a method of using arginase and urease (Japanese Patent Unexamined Publication (Kokai) No. 8-336399, Method for detecting arginine and arginine sensor; hereinafter "the '399 document"). Since urea and ammonia are also detected together with arginine in this quantification method, it cannot be used in a biological sample containing these compounds.

Enzymatic methods for quantifying pyrophosphate include generating inorganic phosphoric acid from pyrophosphate with pyrophosphatase, and quantifying the inorganic phosphoric acid by any of various detection methods (I-a). Commercial products based on this principle include PiPer Pyrophosphate Assay Kit sold by Invitrogen, and EnzChek Pyrophosphate Assay Kit sold by Probe. However, since this measurement method also detects inorganic phosphoric acid together with pyrophosphate, this measurement method cannot be used for a sample contaminated with inorganic phosphoric acid. Furthermore, enzymatic methods for quantifying pyrophosphate include generating ATP from pyrophosphate with ATP sulfurylase or PPDK, and quantifying ATP by any of various detection methods (I-b) (Japanese Patent Unexamined Publication (Kokai) No. 2009-225784, Method for measuring pyrophosphate; hereinafter "the '784 document") and Japanese Patent Unexamined Publication (Kokai) No. 2007-097471, Method and reagent for determining nucleotide sequence; hereinafter "the '471 document"). Commercial products based on this principle include PPiLight Inorganic Pyrophosphate Assay Kit sold by Lanza Rockland. For the detection of ATP in this method, a luminescence method utilizing luciferase or the cycling assay method is used. However, because of the principle, it cannot be used for a sample contaminated with ATP, and when the detection is performed by the luminescence method, the luminescence rapidly decays over time, and therefore the measurement must be performed under a strict measurement environment using an expensive luminescence measuring apparatus. The detection based on the cycling assay can be performed with high sensitivity, but the measurement can be complicated, for example, it is necessary to monitor the absorbance to strictly calculate the reaction rate. In addition, concerning the measurement based on the above principle, an improved method has been reported in which a sample containing ATP can be used (refer to Japanese Patent Unexamined Publication (Kokai) No. 2006-187251, Method for quantifying pyrophosphate; hereinafter "the '251 document"). However, this method uses the steps of performing removal of ATP as a pretreatment, and then quantifying pyrophosphate. Therefore, this method can be used when removal of ATP from the reaction system does not invite any problems, but it cannot be used for a reaction system in which the presence of ATP is desired.

Furthermore, a method of generating hypoxanthine from pyrophosphate with hypoxanthine phosphoribosyltransferase has been reported, and quantifying hypoxanthine (I-c) (Japanese Patent Unexamined Publication (Kokai) No. 2003-174900, Method for quantifying pyrophosphate and nucleic acid and apparatus therefor; hereinafter "the '900 document). The reaction substrates used in this method do not contain inorganic phosphoric acid or ATP, and therefore the method enables measurement of pyrophosphate without being affected by the presence of these compounds. However, by this method, ATP cannot be reproduced in response to pyrophosphate consumption.

The aminoacyl-tRNA synthetase (AARS) is an enzyme that generates aminoacyl-tRNA, AMP, and pyrophosphate by using a specific amino acid, ATP and tRNA as substrates. There are AARSs corresponding to the respective protein-constituting amino acids. AARSs corresponding to the respective protein-constituting amino acids are henceforth indicated with amino acid names linked to "RS". For example, AARS corresponding to alanine is indicated as "AlaRS", and AARS corresponding to cysteine is indicated as "CysRS".

It is known that AARS shows very high substrate specificity for amino acids. The reaction catalyzed by this enzyme consists of the following two-step reactions.

remains trapped in the complex in the absence of tRNA, and so forth. Baldwin et al. also describe that if hydroxylamine is added to the aforementioned complex, the complex decomposes to generate amino acid hydroxamic acid and AMP.

Forbes et al. [(2007), A high-throughput competitive scintillation proximity aminoacyl-tRNA synthetase charging assay to measure amino acid concentration, Anal. Biochem., 363, 246-254; hereinafter "Forbes et al."] reports a method for quantifying an amino acid by adding an extremely small amount of tRNA to react a part of an amino acid in a sample according to the aforementioned reaction formulas 1 and 2.

Japanese Patent Unexamined Publication (Kokai) No. 2011-50357 (Method for analyzing amino acid and biosensor; hereinafter "the '357 document") and Japanese Patent Unexamined Publication (Kokai) No. 2006-166709 (Biosensing apparatus for amino acid analysis, biosensor for amino acid analysis, and aminoacyl-tRNA synthetase for amino acid analysis; "the '709 document") reports a method for quantifying an amino acid by allowing only a reaction of a part of an amino acid in a sample analogous to the reaction according to the aforementioned reaction formula 1, without adding tRNA.

SUMMARY OF THE INVENTION

Aspects to be Achieved by the Invention

Biological samples including plasma can contain a lot of various contaminants, such as inorganic phosphoric acid and urea, and methods for analyzing a subject substance contained in such samples must not be affected by these contaminants.

An enzyme that generates pyrophosphate by using ATP together with a subject substance to be measured as substrates is very promising as an enzyme for measurement, because of the high substrate specificity thereof and high reactivity thereof based on the ATP hydrolysis, which is an exoergic reaction. The high reactivity based on the ATP hydrolysis has been specifically described as a reaction that can irreversibly advance, can advance at high reaction rate, can advance even without ATP hydrolysis due to local energetic disadvantage, and so forth. Furthermore, since the blood concentration of pyrophosphate is below several μM, which is much lower than that of amino acids which typically are present on the order of several tens to several hundreds μM, use of the pyrophosphate-generating enzyme has an advantage that even if a sample is contaminated with pyrophosphate derived from test object, it scarcely affects the quantified values of amino acids. As a premise of use of Equation 1

(Reaction formula 1)  Amino acid + $ATP \rightleftarrows$ (aminoacyl-$AMP$) – $AARS$ complex + pyrophosphate
(Reaction formula 2)  (Aminoacyl–$AMP$) – $AARS$ complex + $tRNA \rightleftarrows$ minoacyl–$tRNA$ + $ATP$ + $AARS$ (Total reaction)      Amino acid + $ATP$ + $tRNA \rightleftarrows$ aminoacyl–$tRNA$ + $ATP$ + pyrophosphate It is known from Baldwin et al. [(1966), Transfer ribonucleic acid-induced hydrolysis of valyladenylate bound to isoleucyl ribonucleic acid synthetase, J. Biol. Chem., 241, 839-845; hereinafter "Baldwin et al."], etc. that the "(aminoacyl-AMP)-AARS complex" forms as shown in the above reaction formula, and this complex is rigid, since AARS such a pyrophosphate-generating enzyme for analysis of a biological sample, it is necessary to quantify pyrophosphate, and the method for quantifying pyrophosphate must satisfy the following requirements:

It can be used for a biological sample containing a lot of inorganic phosphoric acid.

It can be performed in the presence of ATP for coupling with a pyrophosphate-generating enzyme that uses ATP as the substrate.

It can reproduce ATP from pyrophosphate and avoid accumulation of the enzymatic reaction product and reproduction of the substrate.

However, a method for quantifying pyrophosphate that satisfies these requirements is not known, and therefore measurement of amino acid using the aforementioned pyrophosphate-generating enzyme has not been practically performed.

It is known that AARS shows extremely high substrate specificity for an amino acid, and hence it is a promising enzyme for use as an enzyme for quantifying an amino acid.

The quantification method of Forbes et al. mixes a sample, ATP, tRNA, and a radioactively labeled amino acid as the compound to be measured, then allows AARS to act on the mixture, adsorbing the produced aminoacyl-tRNA on beads, and measuring radioactivity thereof to quantify the amino acid. In the quantification method of Forbes et al., it is inevitable to use a radioisotope, since it is the presence of the labeled amino acid that is incorporated into the product that is calculated in this method. Therefore, this quantification method can be used only in an environment where a radioisotope can be handled. Further, this quantification method also requires complicated processes such as adsorption and separation on and from the beads. Furthermore, in this quantification method, tRNA is added to the reaction mixture at a high concentration, and can be as high as 0.5 mg/ml. However, if this concentration is converted to the molar concentration of tRNA corresponding to the amino acid to be measured, it is calculated as 30 (μg)/60 (μl)/30,000 (g/mol)/20=0.8 μM (it is assumed that the molecular weight of tRNA is 30,000, and 20 kinds of tRNAs corresponding to the amino acids are present in equal amounts). The molar concentration of the reaction product is below the aforementioned concentration, and it is difficult to quantify a compound present in such a small amount without using a radioisotope. Therefore, in such a method of adding tRNA as that of Forbes et al., an extremely small amount of the reaction product must be detected, and therefore, use of a radioisotope is inevitable.

The quantification methods of the '357 document and the '709 document include methods in which only an amino acid, ATP, and AARS are allowed to react (the condition of this reaction will be henceforth referred to as "no tRNA addition condition"), and detect a product. Since tRNA is not used in these quantification methods, it is considered that the reaction of the aforementioned reaction formula 2 cannot advance.

In the '357 document and the '709 document, the presence of a (aminoacyl-AMP)-AARS complex such as that mentioned in reaction formula 1 is not mentioned, but it is described that AARS catalyzes a reaction of the following reaction formula 1'. If it is assumed that the reaction advances as described in the reaction formula 1', and the equilibrium is disturbed so that the reaction completely advances rightward, it can be considered that pyrophosphate is produced in the same molar number as that of an amino acid, and the amino acid can be quantified by quantifying pyrophosphate. However, neither of the above patent documents mention any basis for this possibility, nor the reaction of the reaction formula 1, even though the reaction of the reaction formula 1' advances.

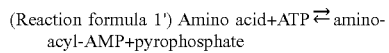

(Reaction formula 1') Amino acid+ATP ⇌ aminoacyl-AMP+pyrophosphate      Equation 2:

The inventors of the present invention performed the measurement in the absence of tRNA as described in the '357 document and the '709 document. However, at least by the detection method used by the inventors of the present invention, significant pyrophosphate production could not be detected (refer to Example 6, 11., no hydroxylamine addition sample). It is considered that the reason no significant pyrophosphate production is detected is that the reaction that actually occurred is not the reaction of the aforementioned reaction formula 1', but the reaction of the aforementioned reaction formula 1. In the reaction of the reaction formula 1, while one molecule of the amino acid reacts, one molecule of AARS is consumed in the formation of the complex. Therefore, unless AARS is added to the system at a molar concentration at least higher than that of the amino acid in the sample, it is theoretically impossible to generate pyrophosphate in the same amount as that of the amino acid in the sample.

The AARS concentration in the reaction mixture as described in Example 6, 11. is about 9 μM, and is markedly lower than the amino acid concentration. Furthermore, the '357 document, the '709 document, and Forbes et al. do not describe that AARS is added to the system at a molar concentration higher than that of the amino acid as the measurement subject. In the '399 document, paragraph [0024], the AARS concentration at the time of quantifying 0 to 100 μM of amino acid is 10 μM, and thus it can be said that AARS is not added at a concentration higher than that of amino acid. Therefore, it is reasonable to consider that, if it is assumed that the reaction of the reaction formula 1 advances to the maximum extent in the methods of the '357 document and the '709 document, only an extremely small amount of the amino acid in the sample can be used for the reaction, and the product is also obtained in a small amount. Any data denying the above are not shown in the aforementioned patent documents.

If only an extremely small amount of the product is produced compared with the amino acid in the sample, such a high sensitivity detection system based on the fluorescence method, sensor electrode, or the like as used in the '357 document becomes indispensable, and detection with a widely used detection system such as those based on absorbance methods becomes impossible. Furthermore, even when a high sensitivity detection system is used, it may cause various problems, such as decrease of sensitivity, variation of measured value, and elevation of the background value.

As described above, the known amino acid quantification methods using AARS are problematic, for example, they require complicated processes using a radioisotope, and only an extremely small amount of the amino acids in the sample can react, and therefore they have not been widely used.

Means for Achieving the Aspects of the Invention

The inventors of the present invention found that if pyrophosphate was reacted with PPDK, and the produced pyruvate was reacted with pyruvate dehydrogenase or pyruvate oxidase, pyrophosphate could be quantified without being affected by the presence of inorganic phosphoric acid or ATP, and with enabling reproduction of ATP.

They further found that if methionine was reacted with AdoMetS, and the produced pyrophosphate was measured with the aforementioned pyrophosphate quantification system, methionine could be selectively quantified without any pretreatment, and accomplished a methionine quantification system based on the above. Furthermore, they also found that if citrulline was reacted with ASS, and the produced pyrophosphate was measured with the aforementioned pyrophosphate quantification system, citrulline could be selectively quantified under a mild condition, and accomplished a citrulline quantification system based on the above. Furthermore, they also found that if arginine was reacted with ADI, and the produced pyrophosphate was measured with the aforementioned pyrophosphate quantification system, arginine could be selectively quantified, and accomplished an arginine quantification system based on the above.

The inventors of the present invention further found that significant pyrophosphate production was not observed in an AARS reaction mixture without added tRNA, but if a reagent that decomposes the (aminoacyl-AMP)-AARS complex was added, pyrophosphate was generated in an amount equivalent to that of the amino acid in the sample. Therefore, they found that an amino acid could be quantified with high sensitivity and little error by reacting the total amount of the amino acid in the reaction mixture as the complex decomposition reaction according to the aforementioned reaction formula 1.

It is an aspect of the present invention to provide a method for quantifying a subject substance, which comprises:
a step of allowing an enzyme to act on the subject substance to generate pyrophosphate in the presence of adenosine triphosphate (ATP);
a step of allowing pyruvate pyrophosphate dikinase (PPDK) to act on the generated pyrophosphate in the presence of adenosine monophosphate (AMP) and phosphoenolpyruvate (PEP) to generate ATP, phosphoric acid, and pyruvate; and
a step of quantifying the generated pyruvate, and wherein the amount of the subject substance is determined based on the amount of generated pyruvate.

It is a further aspect of the present invention to provide a method as described above, wherein the subject substance is an amino acid.

It is an aspect of the present invention to provide a method for quantifying methionine, which comprises:
a step of allowing adenosylmethionine synthetase (AdoMetS) to act on methionine in the presence of ATP to generate adenosylmethionine and pyrophosphate;
a step of allowing PPDK to act on the generated pyrophosphate in the presence of AMP and phosphoenolpyruvate (PEP) to generate ATP, phosphoric acid, and pyruvate; and
a step of quantifying the generated pyruvate, and wherein amount of methionine is determined based on the amount of generated pyruvate.

It is an aspect of the present invention to provide a method for quantifying citrulline, which comprises:
a step of allowing argininosuccinate synthetase (ASS) to act on citrulline in the presence of aspartic acid and ATP to generate AMP, argininosuccinic acid, and pyrophosphate;
a step of allowing PPDK to act on the generated pyrophosphate in the presence of AMP and PEP to generate ATP, phosphoric acid, and pyruvate; and
a step of quantifying the generated pyruvate, and wherein amount of citrulline is determined based on the amount of pyruvate.

It is an aspect of the present invention to provide a method for quantifying arginine, which comprises:
a step of allowing arginine deiminase (ADI) to act on arginine to generate ammonia and citrulline;
a step of allowing ASS to act on the generated citrulline to generate AMP, arginosuccinic acid, and pyrophosphate;
a step of allowing PPDK to act on the generated pyrophosphate in the presence of AMP and PEP to generate ATP, phosphoric acid, and pyruvate; and
a step of quantifying the generated pyruvate, and wherein amount of arginine is determined based on the amount of the generated pyruvate.

It is an aspect of the present invention to provide a method for quantifying an amino acid, which comprises:
a step (A) of allowing an aminoacyl-tRNA synthetase (AARS) corresponding to the amino acid to act on the amino acid and ATP in the presence of an (aminoacyl-AMP)-AARS complex decomposition reagent to obtain pyrophosphate; and
a step (B) of quantifying pyrophosphate generated in step (A), and
wherein step (B) comprises the step of allowing PPDK to act on the generated pyrophosphate in the presence of AMP and PEP to generate ATP, phosphoric acid, and pyruvate; and
a step of quantifying the generated pyruvate, and wherein the amount of the amino acid is determined based on the amount of the generated pyruvate.

It is a further aspect of the present invention to provide a method as described above, wherein the complex decomposition reagent is an amine or carbanion.

It is a further aspect of the present invention to provide a method as described above, wherein the complex decomposition reagent is selected from the group consisting of hydroxylamine, hydrazine, and methylamine.

It is a further aspect of the present invention to provide a method as described above, which is performed in the absence of tRNA.

It is a further aspect of the present invention to provide a method as described above, which is for quantifying two or more kinds of amino acids in one sample, and comprises the steps of:
preparing AARSs corresponding to the respective amino acids as quantification subjects,
preparing a reaction reagent containing required components other than AARSs,
mixing the reaction reagent and the sample,
dividing the mixture into portions at least in the number of the kinds of the subject amino acids, and
adding different AARSs to the divided portions, respectively.

It is a further aspect of the present invention to provide a method as described above, wherein AARS is derived from a thermophile, and step (A) is performed at a temperature of 50° C. or higher.

It is a further aspect of the present invention to provide a method as described above, wherein the step of quantifying pyruvate comprises:
a step of allowing and enzyme or enzymes selected from the group consisting of: (i) lactate dehydrogenase, (ii) pyruvate oxidase, (iii) pyruvate decarboxylase and alcohol dehydrogenase, and (iv) pyruvate decarboxylase and aldehyde dehydrogenase to act on pyruvate.

It is a further aspect of the present invention to provide a method as described above, which is a method for quantifying a subject substance in a sample, and wherein the sample may contain ATP or phosphoric acid.

It is a further aspect of the present invention to provide a method as described above, wherein the sample is derived from blood.

It is an aspect of the present invention to provide a kit for use in the method for quantifying methionine as described above, which comprises ATP, AdoMetS, AMP, PEP, and PPDK, separately or as a mixture of any two or more of these.

It is a further aspect of the present invention to provide a kit for use in the method for quantifying citrulline as described above, which comprises ATP, ASS, AMP, PEP, and PPDK, separately or as a mixture of any two or more of these.

It is a further aspect of the present invention to provide a kit for use in the method for quantifying arginine as described above, which comprises ATP, ASS, ADI, AMP, PEP, and PPDK, separately or as a mixture of any two or more of these.

It is a further aspect of the present invention to provide a kit for use in the method for quantifying an amino acid as described above, which comprises ATP, AARS, AMP, PEP, and PPDK, separately or as a mixture of any two or more of these.

It is an aspect of the present invention to provide a method for quantifying an amino acid, which comprises:
 a step (A) of allowing an aminoacyl-tRNA synthetase (AARS) corresponding to the amino acid to act on the amino acid and ATP in the presence of an (aminoacyl-AMP)-AARS complex decomposition reagent to obtain a reaction product; and
 a step (B) of quantifying the product generated in step (A), and
 wherein amount of the amino acid is determined based on the amount of the generated product.

The present invention also provides the following:
It is an aspect of the present invention to provide a method for quantifying pyrophosphate, which comprises:
 a step of allowing pyruvate pyrophosphate dikinase (PPDK) to act on pyrophosphate in the presence of adenosine monophosphate (AMP) and phosphoenolpyruvate (PEP) to generate adenosine triphosphate (ATP), phosphoric acid, and pyruvate, and
 a step of quantifying the generated pyruvate, and
 wherein the amount of pyrophosphate is determined based on the amount of generated pyruvate.

It is a further aspect of the present invention to provide the method as described above, wherein the step of quantifying pyruvate comprises:
 a step of allowing an enzyme or enzymes selected from the group consisting of: (i) lactate dehydrogenase, (ii) pyruvate oxidase, (iii) pyruvate decarboxylase and alcohol dehydrogenase, and (iv) pyruvate decarboxylase and aldehyde dehydrogenase to act on pyruvate.

It is a further aspect of the present invention to provide the method as described above, which is a method for quantifying pyrophosphate in a sample, and wherein the sample may contain ATP or phosphoric acid.

It is a further aspect of the present invention to provide the method as described above, wherein the sample is derived from blood.

It is an aspect of the present invention to provide a method for quantifying a subject substance, which comprises:
 a step of allowing an enzyme to act on the subject substance to generate pyrophosphate in the presence of ATP;
 a step of allowing PPDK to act on the generated pyrophosphate in the presence of AMP and phosphoenolpyruvate (PEP) to generate ATP, phosphoric acid, and pyruvate; and
 a step of quantifying the generated pyruvate, and
 wherein amount of the subject substance is determined based on the amount of generated pyruvate.

It is a further aspect of the present invention to provide a method for quantifying methionine, which comprises:
 a step of allowing adenosylmethionine synthetase (AdoMetS) to act on methionine in the presence of ATP to generate adenosylmethionine and pyrophosphate;
 a step of allowing PPDK to act on the generated pyrophosphate in the presence of AMP and phosphoenolpyruvate (PEP) to generate ATP, phosphoric acid, and pyruvate; and
 a step of quantifying the generated pyruvate, and
 wherein amount of methionine is determined based on the amount of generated pyruvate.

It is a further aspect of the present invention to provide a method for quantifying citrulline, which comprises:
 a step of allowing argininosuccinate synthetase (ASS) to act on citrulline in the presence of aspartic acid and ATP to generate AMP, arginosuccinic acid, and pyrophosphate;
 a step of allowing PPDK to act on the generated pyrophosphate in the presence of AMP and PEP to generate ATP, phosphoric acid, and pyruvate; and
 a step of quantifying the generated pyruvate, and
 wherein amount of citrulline is determined based on the amount of generated pyruvate.

It is a further aspect of the present invention to provide a method for quantifying arginine, which comprises:
 a step of allowing arginine deiminase (ADI) to act on arginine to generate ammonia and citrulline;
 a step of allowing ASS to act on the generated citrulline to generate AMP, arginosuccinic acid, and pyrophosphate;
 a step of allowing PPDK to act on the generated pyrophosphate in the presence of AMP and PEP to generate ATP, phosphoric acid, and pyruvate; and
 a step of quantifying the generated pyruvate, and
 wherein the amount of arginine is determined based on the amount of generated pyruvate.

It is an aspect of the present invention to provide a kit for use in the method for quantifying methionine as described above, which comprises ATP, AdoMetS, AMP, PEP, and PPDK, separately or as a mixture of any two or more of these.

It is an aspect of the present invention to provide a kit for use in the method for quantifying citrulline as described above, which comprises ATP, ASS, AMP, PEP, and PPDK, separately or as a mixture of any two or more of these.

It is an aspect of the present invention to provide a kit for use in the method for quantifying arginine as described above, which comprises ATP, ASS, ADI, AMP, PEP, and PPDK, separately or as a mixture of any two or more of these.

The present invention further provides the following:
It is a further aspect of the present invention to provide a method for quantifying an amino acid, which comprises:
 a step (A) of allowing an aminoacyl-tRNA synthetase (AARS) corresponding to the amino acid to act on the amino acid and adenosine triphosphate (ATP) in the presence of an (aminoacyl-AMP)-AARS complex decomposition reagent to obtain a reaction product; and
 a step (B) of quantifying the product generated in step (A), and
 wherein the amount of the amino acid is determined based on the amount of the generated product.

It is a further aspect of the present invention to provide the method as described above, which is performed in the absence of tRNA.

It is a further aspect of the present invention to provide the method as described above, wherein the complex decomposition reagent is an amine or carbanion.

It is a further aspect of the present invention to provide the method as described above, wherein the complex decomposition reagent is selected from the group consisting of hydroxylamine, hydrazine, and methylamine.

It is a further aspect of the present invention to provide the method as described above, wherein the product is quantified in step (B) by measuring absorbance.

It is a further aspect of the present invention to provide the method as described above, wherein the product quantified in step (B) is pyrophosphate, and the quantification of pyrophosphate comprises the step of allowing pyruvate pyrophosphate dikinase (PPDK) to act on pyrophosphate.

It is a further aspect of the present invention to provide the method as described above, which is for quantifying an amino acid in a sample, and the sample is derived from blood.

It is a further aspect of the present invention to provide the method as described above, which is for quantifying two or more kinds of amino acids in one sample, and comprises the steps of:
preparing AARSs corresponding to the respective amino acids to be quantified,
preparing a reaction reagent containing required components other than AARSs,
mixing the reaction reagent and the sample,
dividing the mixture into portions at least in the number of the kinds of the subject amino acids, and
adding different AARSs to the divided portions, respectively.

It is a further aspect of the present invention to provide the method as described above, wherein AARS is derived from a thermophile, and step (A) is performed at a temperature of 50° C. or higher.

Effect of the Invention

Since the quantification ability of the method for quantifying pyrophosphate of the present invention is not affected by the presence of inorganic phosphoric acid or ATP, it can be performed in a sample containing a lot of contaminants such as blood. Furthermore, since PPDK is used, in a coupled system with an enzyme that generates pyrophosphate by using ATP as a substrate, ATP can be regenerated from pyrophosphate. According to the present invention, the system shows only a small change in signal intensity for the quantification after completion of the reaction, and the system enables the quantification on the basis of absorbance measurement. Therefore, the method can be conveniently performed even in a measurement environment lack expensive special-purpose apparatuses such as luminescence detection apparatus.

The methionine quantification method of the present invention can be performed in a sample containing amino acids other than methionine or ammonia without any pretreatment. Furthermore, since it is not a stop reaction method, and a substantial amount of the total methionine in a sample can be quantified as the corresponding amount to pyrophosphate, it enables easy monitoring of methionine production over time.

The citrulline quantification method of the present invention can be performed in a sample containing amino acids other than a citrulline or urea without any pretreatment. Furthermore, it does not require incubation at a high temperature, and enables easy monitoring of citrulline production over time.

The arginine quantification method of the present invention can be performed for a sample containing amino acids other than arginine and citrulline, urea, or ammonia without any pretreatment.

The quantification methods using AARS of the present invention show the following superior advantages compared with the quantification method described in Forbes et al.:
Since they do not use a radioisotope and a detection apparatus therefor, it can be used with usual equipment and in a usual environment;
They do not require complicated processes such as adsorption and separation on and from beads after the enzymatic reaction, and a mixture of the reaction mixture and a sample as it is can be used for the measurement;
Whereas the quantification method described in Forbes et al. requires 2 hours for the measurement even if the time required for the adsorption on beads and the following processes is excluded, the methods of the present invention enable the measurement within about 10 minutes;

The quantification methods using AARS of the present invention show the following superior advantages compared with the quantification methods described in the '357 document and the '709 document;
Since the product is obtained in an amount equivalent to the amount of the amino acid in the sample, they enable highly sensitive and highly precise quantification;
They enable the quantification with usual absorbance measurement without using any fluorescence reagent or sensor electrode.
Whereas the quantification methods described in the '357 document and the '709 document require 40 minutes (see the '357 document, paragraph [0075]) and 55 minutes (see the '709 document, paragraph [0024]), respectively, for the measurement, the methods of the present invention enable the measurement within about 10 minutes.

DESCRIPTION OF THE PREFERRED EMBODIMENTS

Figure 1A:
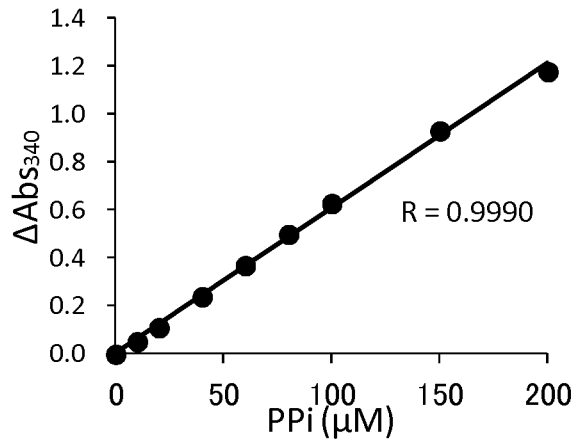
FIGS. 1A and 1B are graphs showing a pyrophosphate calibration curve when using lactate dehydrogenase (for measurement with absorptiometer).

The present invention provides a method for quantifying a subject substance, such as, for example, amino acids. The method of the present invention includes the following steps:

a step of allowing an enzyme, which can generate pyrophosphate by using adenosine triphosphate (ATP) as a substrate to convert the subject substance, to act on the subject substance to generate pyrophosphate;

a step of allowing pyruvate pyrophosphate dikinase (PPDK) to act on the generated pyrophosphate in the presence of adenosine monophosphate (AMP) and phosphoenolpyruvate (PEP) to generate ATP, phosphoric acid, and pyruvate; and a step of quantifying the generated pyruvate.

Furthermore, in the method of the present invention, the amount of the subject substance is determined based on the amount of pyruvate. The method of the present invention also has the characteristic that the ATP consumed in the first reaction is regenerated simultaneously with detection of pyrophosphate.

Various enzymes are known that generate pyrophosphate by using ATP together with a subject substance as substrates, and several tens or more enzymes according to the EC classification are registered. Examples include, for example, flavine adenine dinucleotide synthetase (FAD synthetase), phosphoribulokinase, streptomycin 3"-adenylyltransferase, biotin-CoA ligase, and acetoacetate-CoA ligase. The enzyme that generates pyrophosphate by using ATP together with a subject substance as substrates can be exemplified by, in particular, adenosylmethionine synthetase (AdoMetS), argininosuccinate synthetase (ASS), arginine deiminase (ADI), and aminoacyl-tRNA synthetase (AARS), but those skilled in the art will be able to understand that the descriptions herein can be appropriately applied to use of other enzymes, and so are not limited to these examples.

The enzymes that generate pyrophosphate by using ATP together with a subject substance as substrates can be classified according to origin, location (membrane, cytoplasm, outside of cell, etc.), substrate specificity and reaction specificity, active site, residue of active site, and so forth. For example, there are no organisms that do not have AARS that have been reported to date, however organisms not having AdoMetS, ASS, or ADI are known to exist. Furthermore, AdoMetS and ASS react with the side chain moiety of amino acids, and AARS reacts with the carboxyl group of amino acids.

I. Method for Quantifying Amino Acid Utilizing Specific Pyrophosphate Quantification Method According to one embodiment of the present invention, methods for quantifying methionine, citrulline, and arginine using a specific method for quantifying pyrophosphate are provided.

The term "quantification (quantify)" of a subject substance can mean the measurement of the amount of the subject substance, unless especially indicated, and the amount may be measured as an absolute amount, or may be measured as a concentration in a sample.

Method for Quantifying Pyrophosphate:

The method for quantifying pyrophosphate is:

a first step of allowing PPDK to act on pyrophosphate in the presence of a metal ion, AMP and phosphoenolpyruvate (PEP) to generate ATP, phosphoric acid, and pyruvate, and a second step of quantifying the generated pyruvate, and the amount of pyrophosphate is determined on the basis of the amount of pyruvate generated in the first step.

The first step can be performed by incubating pyrophosphate in a test sample with PPDK, metal ion, AMP and PEP. This reaction catalyzed by PPDK is represented by the following reaction formula.

Formula 1: 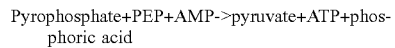

Pyrophosphate+PEP+AMP->pyruvate+ATP+phosphoric acid

The term "phosphoric acid" can refer to inorganic phosphoric acid ($H_3PO_4$), unless especially indicated. Phosphoric acid may also be referred to as orthophosphoric acid.

PPDK is not limited by origin, enzyme name, EC number, production method, and so forth, so long as it is an enzyme that is able to catalyze the aforementioned reaction. For example, PPDK enzymes derived from the genus *Propionibacterium* or the genus *Thermoproteus*, more specifically, those derived from *Propionibacterium freudenreichii* (Pf) and *Thermoproteus tenax* (Tt) can be used. The Pf-derived PPDK is one of the well-studied enzymes of bacterium origin. It is advantageous in that a large expression amount thereof can be expected in an *Escherichia coli* expression system, it can be stably stored at 4° C. as a mixture with glycerol, and it does not show marked decrease of activity even after repetition of freezing and thawing. Since Tt is a super-thermophile, the Tt-derived PPDK is superior in that it can be purified at an ordinary temperature, and it is not denatured and is usable even at a high temperature. More specifically, the enzyme derived from the *Propionibacterium freudenreichii* subsp. *shermanii* NBRC 12426 strain or the *Thermoproteus tenax* NBRC 100435 strain can be used.

The amount of PPDK to be used is not particularly limited so long as it enables the quantification of pyrophosphate according to the present invention, and it can be appropriately determined according to amount of pyrophosphate contained in a sample, apparatus to be used, purity and type of PPDK. The amount of PPDK to be used can be, as for the minimum amount, 0.001 U/ml or more, 0.005 U/ml or more, 0.01 U/ml or more. As for the maximum amount, the amount can be 10 U/ml or less, 5 U/ml or less, or 1 U/ml or less.

The first step is performed in the presence of AMP. The concentration of AMP can be, at a minimum, 0.01 mM or higher, 0.025 mM or higher, 0.05 mM or higher. Furthermore, at a maximum, the concentration can be 20 mM or lower, 10 mM or lower, or 5 mM or lower.

The first step can be performed in the presence of a high energy phosphate compound such as PEP. The concentration of PEP can be, at a minimum, 0.01 mM or higher, 0.025 mM or higher, or 0.05 mM or higher. Furthermore, at a maximum, the concentration can be 20 mM or lower, 10 mM or lower, or 5 mM or lower.

The first step can be performed in the presence of a metal ion. The metal ion can be magnesium ion, cobalt ion, or manganese ion, and a particular example is magnesium ion. The amount of the metal ion can be, at a minimum, for example, for magnesium ion, 0.1 equivalent or more, 0.2 equivalent or more, or 0.4 equivalent or more, relative to the concentration of AMP. Furthermore, at a maximum, the amount of magnesium ion can be 10 equivalents or less, 5 equivalents or less, 2.5 equivalents or less. A particular example is 0.5 to 2 equivalents, for example, 1 equivalent, relative to the phosphate donor.

In the second step, the pyruvate in the reaction system is quantified using, for example, a lactate dehydrogenase reaction. Lactate dehydrogenase is an enzyme that is distributed over a wide range of organisms, and catalyzes the following reaction.

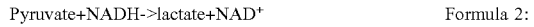

Pyruvate+NADH->lactate+NAD⁺    Formula 2:

Lactate dehydrogenases can be derived from various types of organisms. For example, lactate dehydrogenase from rabbit, swine, bovine, fowl, lactic acid bacteria, or yeast can be used.

The amount of lactate dehydrogenase to be used is not particularly limited so long as the quantification of pyrophosphate is enabled, and it can be appropriately determined according to amount of pyrophosphate contained in a sample, apparatus to be used, purity and type of the enzyme. The amount of the enzyme to be used can be, at a minimum, 0.002 U/ml or more, 0.005 U/ml or more, or 0.01 U/ml or more. Furthermore, at a maximum, the amount of the enzyme can be 4 U/ml or less, 2 U/ml or less, or 1 U/ml or less.

Further, the second step can be performed also in the presence of NADH. The influence of the NADH concentration is comparatively significant. For example, if the NADH concentration is unduly low, detection of absorbance becomes difficult, and if it is unduly high, the accuracy of the measured value of the decreased amount thereof reduces. The amount of NADH can be, at a minimum, 0.01 mM or higher, 0.02 mM or higher, 0.05 mM or higher. At a maximum, the amount of NADH can be 4 mM or lower, 2 mM or lower, 1 mM or lower.

In a system using lactate dehydrogenase, the amount of pyruvate that is produced is calculated by measuring the decrease in the amount of NADH, which decreases as the reaction advances, through measurement of the absorbance at 340 nm.

In a system using lactate dehydrogenase, the second step can progress simultaneous with the first step (I-A). Although the reaction temperature is appropriately determined in accordance with optimum temperature for the chosen enzyme, and so forth, the reaction can be performed at room temperature to 37° C., for example, 30° C. Although the reaction time can be appropriately determined in consideration of the amount of pyrophosphate contained in a test sample, and so forth, the reaction advances promptly, and the total amount of pyrophosphate in a sample can be used for the oxidation of NADH within 20 minutes, for example, in about 7 to 13 minutes. If necessary, these steps can be performed in an appropriate buffer such as 20 mM imidazole-HCl (pH 7.0). The concentrations of the components in the same system can be appropriately determined by those skilled in the art, and for example, they may be in the following ranges.

MgCl₂: 0.5 to 50 mM
PEP: 0.05 to 5 mM
AMP: 0.05 to 5 mM
NADH: 0.05 to 1 mM
PPDK: 0.01 to 1 U/ml
Lactate dehydrogenase: 0.01 to 1 U/ml In the embodiment using the lactate dehydrogenase reaction, pyrophosphate in the range of at least 0 to 200 μM can be quantified.

The second step can also be performed in a hydrogen peroxide detection system by using a reaction catalyzed by pyruvate oxidase.

The pyruvate oxidase catalyzes the following reaction:

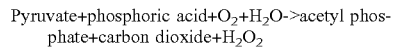

Pyruvate+phosphoric acid+O₂+H₂O->acetyl phosphate+carbon dioxide+H₂O₂    Formula 3:

The pyruvate oxidase is not particularly limited, and can include pyruvate oxidase derived from various organisms, for example, those derived from the genus *Pseudomonas*, can be used.

The amount of the pyruvate oxidase is not particularly limited so long as the quantification of pyrophosphate is enabled, and can be appropriately determined according to the amount of pyrophosphate contained in a sample, apparatus to be used, and purity and type of the enzyme. The amount of the enzyme can be, at a minimum, 0.03 U/ml or more, 0.07 U/ml or more, or 0.15 U/ml or more. At a maximum, the enzyme amount can be 60 U/ml or less, 30 U/ml or less, or 15 U/ml or less.

Hydrogen peroxide generated by the action of the pyruvate oxidase can be quantified by a known method, for example, by using a peroxidase reaction. The peroxidase may be any peroxidase that can be used in the quantification of hydrogen peroxide, and examples thereof include horseradish-derived peroxidase.

The amount of the peroxidase is not particularly limited so long as the quantification of pyrophosphate of the present invention is enabled, and it can be appropriately determined according to amount of pyrophosphate contained in a sample, apparatus to be used, and purity and type of the enzyme. The amount of the enzyme can be, at a minimum, 0.03 U/ml or more, 0.07 U/ml or more, or 0.15 U/ml or more. At a maximum, the enzyme amount can be 300 U/ml or less, 150 U/ml or less, or 75 U/ml or less.

Furthermore, as the electron acceptor that reacts with peroxidase, any color developing agent or fluorescent agent that can serve as a substrate of the peroxidase can be used. Examples of the color developing agent include, for example, 4-aminoantipyrine:phenol, and so forth. With the horseradish-derived peroxidase, hydrogen peroxide, and the aforementioned color developing agent react as shown below, and the quinoneimine dye can be detected by measuring the absorbance at 505 nm.

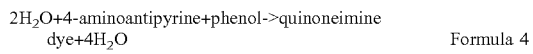

$2H_2O + 4\text{-aminoantipyrine} + \text{phenol} \rightarrow \text{quinoneimine dye} + 4H_2O$  Formula 4

Further, examples of the fluorescent agent that reacts with the peroxidase include 10-acetyl-3,7-dihydroxyphenoxazine (ADHP), and so forth. With the horseradish-derived peroxidase, resorufin, which is a fluorescent substance, is generated by the reaction of hydrogen peroxide and ADHP, and it can be detected on the basis of fluorescence of 590 nm (excitation, 530 nm). The color developing agent and fluorescent agent such as 4-aminoantipyrine and ADHP can be appropriately chosen by those skilled in the art according to the type of peroxidase. Furthermore, the wavelength for the detection can also be appropriately chosen by those skilled in the art according to the type of the color developing agent or fluorescent agent used.

The second step using the pyruvate oxidase can also be simultaneously advanced with the first step in the same system. Although the reaction temperature is appropriately determined in consideration of the optimum temperature for the enzyme to be used, and so forth, the reaction can be appropriately performed at room temperature to 37° C., for example, 30° C. Although the reaction time can be appropriately determined in consideration of the amount of pyrophosphate present in a test sample, the reaction advances promptly, and the total amount of pyrophosphate in a sample can be substantially consumed by the generation of hydrogen peroxide within 20 minutes, for example, in about 7 to 13 minutes. If necessary, these steps can be performed in an appropriate buffer such as 20 mM imidazole-HCl (pH 7.0).

When all the steps are performed in the same system by using 4-aminoantipyrine and phenol, the concentrations of the components can be appropriately determined by those skilled in the art, and for example, they may be in the following ranges:
$MgCl_2$: 2.5 to 250 mM
$NH_4Cl$: 1 to 100 mM
PEP: 0.05 to 5 mM
AMP: 0.05 to 5 mM
PPDK: 0.01 to 1 U/ml
4-Aminoantipyrine: 0.1 to 10 mM
Phenol: 0.1 to 10 mM
Pyruvate oxidase: 0.15 to 15 U/ml
Peroxidase: 0.15 to 75 U/ml In the embodiment using 4-aminoantipyrine and phenol, pyrophosphate in the range of at least 0 to 200 μM can be quantified.

When all the steps are performed in the same system by using ADHP, the concentrations of the components can be appropriately determined by those skilled in the art, and for example, they may be in the following ranges:
$MgCl_2$: 0.5 to 50 mM
$NH_4Cl$: 1 to 100 mM
PEP: 0.05 to 5 mM
AMP: 0.05 to 5 mM
PPDK: 0.01 to 1 U/ml
Na—$PO_4$: 0.05 to 5 mM
ADHP: 50 μM
Pyruvate oxidase: 0.15 to 15 U/ml
Peroxidase: 0.15 to 75 U/ml In the embodiment using ADHP, pyrophosphate in the range of at least 0 to 10 μM can be quantified. According to this embodiment, a trace amount of pyrophosphate can be measured.

The second step may also be performed in a system constructed so that pyruvate is reacted with a color developing reagent such as 2,4-dinitrophenylhydrazine, besides two kinds of the aforementioned enzymes, and absorbance of the product is measured. This system may similarly develop a color with a 2-oxo acid other than pyruvate. The second step may also be performed in a system constructed so that decrease of NADH is detected by using pyruvate decarboxylase and alcohol dehydrogenase. Furthermore, the second step may also be performed in a system constructed so that generation of NADH is detected by using pyruvate decarboxylase and acetaldehyde dehydrogenase. Conditions required for performing these steps can be appropriately designed by those skilled in the art.

The method for quantifying pyrophosphate of the present invention can be performed even in the presence of phosphoric acid or ATP. Furthermore, it has the advantage that ATP can be generated. Conventional methods for quantifying pyrophosphate include generating inorganic phosphoric acid from pyrophosphate with pyrophosphatase, and quantifying inorganic phosphoric acid by any of various detection methods (I-a), generating ATP from pyrophosphate with ATP sulfurylase or PPDK, and quantifying ATP by any of various detection methods (I-b), and generating hypoxanthine from pyrophosphate with hypoxanthine phosphoribosyltransferase, and quantifying hypoxanthine (I-c), but these method do not have the characteristics as mentioned above.

The characteristics of the method of the present invention and the conventional methods are summarized in the following table.

TABLE 1

|  | Conventional method 1-a | Conventional method 1-b | Conventional method 1-c | Pyrophosphate quantification method of the present invention |
|---|---|---|---|---|
| Quantification in the presence of inorganic phosphoric acid | X | ◯ | ◯ | ◯ |
| Quantification in the presence of ATP | ◯ | X | ◯ | ◯ |
| Reproduction of ATP | X | ◯ | X | ◯ |

◯ . . . Possible,
X . . . impossible

Since the method for quantifying pyruvate of the present invention can also be performed in the presence of ATP, it can be used to quantify a subject substance in which the quantification of the subject substance is coupled with an enzymatic reaction that generates pyrophosphate by using ATP together with a subject substance as substrates, such as sequential reactions catalyzed by two or more kinds of enzymes, especially sequential reactions in which a product generated with one enzyme is used as a substrate for another enzyme. Since the enzyme that generates pyrophosphate by using ATP together with a subject substance as substrates shows high substrate specificity, and high reactivity based on the ATP hydrolysis as an exoergic reaction, it is very promising as an enzyme for measurement. Examples of the subject substance to be measured include methionine, citrulline, arginine, and so forth.

In the method of the present invention in which the pyrophosphate-dependent decrease of absorbance is measured, pyrophosphate-non-dependent decrease of absorbance may also occur, although it may occur very weakly. The velocity of this non-dependent decrease of absorbance is in proportion to the amount of PPDK which is added. Therefore, if a large excess amount of PPDK is added to the reaction mixture, pyrophosphate-non-dependent decrease of absorbance becomes large, and may cause errors. Accordingly, the amount of PPDK can be suppressed relative to the chosen enzyme (lactate dehydrogenase, AdoMetS described later, etc.). This is because, if the amount of PPDK is suppressed as described above, the reaction catalyzed by PPDK becomes the rate-limiting step, and the influence of the aforementioned decrease of absorbance can be suppressed. Furthermore, PPDK catalyzes a reversible reaction, and therefore even if the reaction proceeds with only PPDK in the presence of pyrophosphate, the reaction reaches equilibrium before pyrophosphate is completely consumed. However, in the embodiment of present invention in which the reactions are simultaneously allowed in the same system, the reaction is coupled with a reaction catalyzed by an enzyme that irreversibly catalyzes the reaction, such as lactate dehydrogenase (the reaction substantially completely advances to produce lactic acid in the presence of sufficient amount of NADH) and pyruvate oxidase (catalyzes irreversible reaction), and thereby pyrophosphate can be substantially completely converted. Furthermore, the enzymes AdoMetS, ASS, and ADI described later also show strong irreversibility, and also contribute to the complete reaction of the total amount of the substrate.

From such a viewpoint as mentioned above, in the method of the present invention in which the reactions are performed in the same system, the amount of PPDK may be, for example, 1/20 to 1/2, or 1/10 to 1/2, of the amount of lactate dehydrogenase, or 1/10 to 1/1.5, or 1/5 to 1/1.5, of the amount of AdoMetS, ASS, or ADI.

Method for Quantifying Methionine

The method for quantifying methionine of the present invention is:

a first step of allowing PPDK to act on pyrophosphate in the presence of AMP and phosphoenolpyruvate (PEP) to generate ATP, phosphoric acid, and pyruvate; and a second step (II-B) of quantifying the generated pyruvate, wherein the amount of methionine is determined based the amount of generated pyruvate, and pyrophosphate is generated by a third step, that is the step of allowing adenosylmethionine synthetase (AdoMetS) to act on methionine in the presence of ATP to generate adenosylmethionine and pyrophosphate.

The second step can be performed by incubating methionine in a test sample with the adenosylmethionine synthetase (AdoMetS) and ATP. The reaction catalyzed by AdoMetS is represented by the following reaction formula.

Methionine+ATP+$H_2O$->adenosylmethionine+pyrophosphate+phosphoric acid     Formula 5:

The term "methionine" can mean L-methionine, unless especially indicated. Furthermore, the "adenosylmethionine synthetase" may be generally called "S-adenosylmethionine synthetase" or "methionine adenosyltransferase".

AdoMetS derived from various organisms can be used. AdoMetS is distributed over a comparatively wide range of microorganisms. For example, AdoMetS derived from *Escherichia coli* and yeast are known, and any of these can be used. If the enzyme is derived from a host, it is expected that a large expression amount can be obtained, and therefore when it is expressed in *Escherichia coli* as a host and used, the enzyme derived from *Escherichia coli* may be chosen.

The amount of AdoMetS to be used is not particularly limited so long as quantification of methionine is enabled, and it can be appropriately determined according to amount of methionine contained in a sample, apparatus to be used, purity and type of the enzyme. The amount of the enzyme can be, at a minimum, 0.001 U/ml or more, 0.005 U/ml or more, or 0.01 U/ml or more. Furthermore, at a maximum, the enzyme amount can be 10 U/ml or less, 5 U/ml or less, or 1 U/ml or less.

The explanations and descriptions of the first and second steps as applied to the method of quantifying pyrophosphate can be applied to the steps in the method for quantifying methionine, respectively, unless indicated otherwise.

The second step in the method for quantifying methionine may be performed in a system using lactate dehydrogenase or a system using pyruvate oxidase. Furthermore, as in the second step of the pyrophosphate quantification, the second step in the methionine quantification may be performed in a system so that pyruvate reacts with a color developing reagent such as 2,4-dinitrophenylhydrazine, and absorbance of the product is measured, so that decrease of NADH is detected by using pyruvate decarboxylase and alcohol dehydrogenase, or so that the generation of NADH is detected by using pyruvate decarboxylase and acetaldehyde dehydrogenase.

The first, second, and third steps of the methionine quantification can occur simultaneously in the same system. Although the reaction temperature is appropriately determined in consideration of the optimum temperature for the chosen enzyme, and so forth, the reaction can be appropriately performed at room temperature to 37° C., for example, 30° C. Although the reaction time can be appropriately determined in consideration of the amount of pyrophosphate present in a test sample, and so forth, the reaction advances promptly, and the total amount of methionine in a sample can be substantially measured by measuring the corresponding amount of pyruvate within 20 minutes, for example, in about 7 to 13 minutes. If necessary, these steps can be performed in an appropriate buffer such as 20 mM imidazole-HCl (pH 7.0).

The concentrations of the components in the system can be appropriately determined by those skilled in the art, and for example, they may be in the following ranges.

$MgCl_2$: 0.5 to 50 mM
ATP: 0.1 to 10 mM
PEP: 0.04 to 4 mM
AMP: 0.04 to 4 mM

NADH: 0.025 to 2.5 mM
PPDK: 0.01 to 1 U/ml
AdoMetS: 0.01 to 1 U/ml
Lactate dehydrogenase: 0.01 to 1 U/ml In the embodiment using the lactate dehydrogenase reaction, methionine in the range of at least 0 to 200 µM can be quantified.

Further, by this method of the present invention, methionine can be selectively quantified even if the sample is contaminated with 19 kinds of amino acids constituting proteins, other than methionine, and ammonia.

Method for Quantifying Citrulline:

The method for quantifying citrulline of the present invention includes the following steps:

a first step of allowing PPDK to act on pyrophosphate in the presence of AMP and phosphoenolpyruvate (PEP) to generate ATP, phosphoric acid, and pyruvate; and a second step (III-B) of quantifying the generated pyruvate, wherein the amount of citrulline is determined based on the amount of generated pyruvate, and pyrophosphate is generated by a third step, that is, the step of allowing argininosuccinate synthetase (ASS) to act on citrulline in the presence of aspartic acid (Asp) and ATP to generate AMP, arginosuccinic acid, and pyrophosphate.

The third step can be performed by incubating citrulline in a test sample with ASS, ATP, etc. The reaction catalyzed by ASS is represented by the following reaction formula.

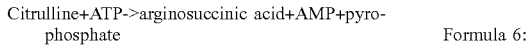

Citrulline+ATP->arginosuccinic acid+AMP+pyrophosphate      Formula 6:

ASS derived from various kinds of organisms can be used. ASS is distributed over a comparatively wide range of microorganisms. For example, ASS derived from *Escherichia coli* and yeast are known, and any of these can be used. If the enzyme is derived from a host, it is expected that a larger expression amount can be obtained, and therefore when it is expressed in *Escherichia coli* as a host, the enzyme derived from *Escherichia coli* may be chosen.

The amount of ASS to be used is not particularly limited so long as quantification of citrulline is enabled, and it can be appropriately determined according to amount of citrulline contained in a sample, apparatus to be used, purity and type of the enzyme. The amount of the enzyme to be used can be, at a minimum, 0.001 U/ml or more, 0.005 U/ml or more, or 0.01 U/ml or more. Furthermore, at a maximum, the enzyme amount can be 10 U/ml or less, 5 U/ml or less, or 1 U/ml or less.

The explanations and descriptions of the aforementioned first and second steps in the pyrophosphate quantification can be applied to the first and second steps in the citrulline quantification, respectively, unless otherwise indicated.

The second step may be performed in a system using lactate dehydrogenase or a system using pyruvate oxidase. Furthermore, like the aforementioned second step (I-B) in the pyrophosphate quantification, the second step in the citrulline quantification may be performed so that pyruvate is reacted with a color developing reagent such as 2,4-dinitrophenylhydrazine, and absorbance of the product is measured, so that a decrease of NADH is detected by using pyruvate decarboxylase and alcohol dehydrogenase, or so that the generation of NADH is detected by using pyruvate decarboxylase and acetaldehyde dehydrogenase.

The first, second, and third steps of the citrulline quantification can occur simultaneously in the same system. Although the reaction temperature is appropriately determined in consideration of the optimum temperature for the chosen enzyme, and so forth, the reaction can be appropriately performed at room temperature to 37° C., for example, 30° C. Although the reaction time can be appropriately determined in consideration of amount of pyrophosphate present in a test sample, and so forth, the reaction advances promptly, and the total amount of citrulline in a sample can be substantially measured by measuring the corresponding amount of pyruvate within 20 minutes, for example, in about 7 to 13 minutes. If necessary, these steps can be performed in an appropriate buffer such as 20 mM imidazole-HCl (pH 7.0).

When the reactions are performed in the same system, AMP is generated in the reaction in which ASS is involved, therefore addition of AMP is not theoretically absolutely necessary, but if AMP is not added, such an influence as described below may occur. If AMP is not added, the generated AMP concentration is lower than if excess AMP is added, that is, it becomes the same concentration as that of pyrophosphate at each time point, and therefore the reaction rate of the PPDK reaction may decrease. This influence becomes more significant especially immediately before the end of the reaction. When all the pyrophosphate is consumed by the reaction, not only the pyrophosphate concentration, but also the AMP concentration correspondingly decreases, and the PPDK reaction may become extremely difficult to advance due to the decrease of the concentrations of two of the substrates. This may result in a lot of unreacted pyrophosphate. In such a case, the quantified amount is lower than the correct value by the amount corresponding to the unreacted pyrophosphate, and therefore the quantified value may be inaccurate.

The concentrations of the components in the system can be appropriately determined by those skilled in the art, and for example, they may be within the following ranges:
MgCl$_2$: 0.5 to 50 mM
Aspartic acid: 0.2 to 20 mM
PEP: 0.02 to 2 mM
ATP: 0.1 to 10 mM
AMP: 0.025 to 2.5 mM
NADH: 0.025 to 2.5 mM
PPDK: 0.01 to 1 U/ml
ASS: 0.01 to 1 U/ml
Lactate dehydrogenase: 0.01 to 1 U/ml In the embodiment using the lactate dehydrogenase reaction, citrulline in the range of at least 0 to 200 µM can be quantified.

By this method of the present invention, citrulline can be selectively quantified in the presence of various contaminants, such as the 20 different kinds of amino acids that make up proteins and urea. In addition, even when a test sample is contaminated with aspartic acid, the method enables selective quantification of citrulline.

Method for Quantifying Arginine:

The method for quantifying arginine of the present invention can include the following steps:

a first step of allowing PPDK to act on pyrophosphate in the presence of AMP and phosphoenolpyruvate (PEP) to generate ATP, phosphoric acid, and pyruvate; and a second step of quantifying the generated pyruvate, wherein the amount of arginine is determined based on the amount of generated pyruvate, and pyrophosphate is generated by a fourth step of allowing arginine deiminase (ADI) to act on arginine to generate ammonia and citrulline; and a third step of allowing ASS to act on the generated citrulline to generate AMP, arginosuccinic acid, and pyrophosphate.

The fourth step can be performed by incubating arginine in a test sample with arginine deiminase (ADI). The reaction catalyzed by this ADI is represented by the following reaction formula.

Arginine->citrulline+ammonia    Formula 7:

The term "arginine" can mean L-arginine, unless especially indicated.

ADI derived from various kinds of organisms can be used. For example, ADI derived from *Pseudomonas aeruginosa* and lactic acid bacteria are known, and any of these can be used. Furthermore, ADI derived from *P. aeruginosa*, which is considered to contain an ADI gene, and in which the gene product thereof is considered to physiologically function, may be prepared and used.

The amount of ADI to be used is not particularly limited so long as quantification of arginine is enabled, and it can be appropriately determined according to amount of arginine contained in a sample, apparatus to be used, purity and type of the enzyme. The amount of the enzyme can be, at a minimum, 0.001 U/ml or more, 0.005 U/ml or more, or 0.01 U/ml or more. Furthermore, at a maximum, the enzyme amount can be 10 U/ml or less, 5 U/ml or less, 1 U/ml or less.

The explanations and descriptions of the aforementioned first and second steps in the pyrophosphate quantification can be applied to the first and second steps of the arginine quantification, respectively, unless otherwise indicated. Furthermore, the explanation and description of the aforementioned third step of the citrulline quantification can be applied to the third step of the arginine quantification, unless otherwise indicated.

The second step of the arginine quantification may be performed in a system using lactate dehydrogenase or a system using pyruvate oxidase. Furthermore, like the aforementioned second step in the pyrophosphate quantification, the second step in the arginine quantification may be performed in a system constructed so that pyruvate is reacted with a color developing reagent such as 2,4-dinitrophenylhydrazine, and absorbance of the product is measured, so that decrease of NADH is detected by using pyruvate decarboxylase and alcohol dehydrogenase, or so that generation of NADH is detected by using pyruvate decarboxylase and acetaldehyde dehydrogenase.

The first, second, third, and fourth steps of the arginine quantification can occur simultaneously in the same system. Although the reaction temperature is appropriately determined in consideration of the optimum temperature for the chosen enzyme to be used, and so forth, the reaction can be appropriately performed at room temperature to 37° C., for example, 30° C. Although the reaction time can be appropriately determined in consideration of amount of pyrophosphate present in the test sample, and so forth, the reaction advances promptly, and the total amount of arginine in a sample can be substantially measured by measuring the corresponding amount of pyruvate within 20 minutes, for example, in about 7 to 13 minutes. If necessary, these steps can be performed in an appropriate buffer such as 20 mM imidazole-HCl (pH 7.0).

The concentrations of the components in the system can be appropriately determined by those skilled in the art, and for example, they may be in the following ranges:
MgCl$_2$: 0.5 to 50 mM
Aspartic acid: 0.2 to 20 mM
PEP: 0.02 to 2 mM
ATP: 0.1 to 10 mM
AMP: 0.025 to 2.5 mM
NADH: 0.025 to 2.5 mM
PPDK: 0.01 to 1 U/ml
ASS: 0.01 to 1 U/ml
ADI: 0.01 to 1 U/ml
Lactate dehydrogenase: 0.01 to 1 U/ml In the embodiment using the lactate dehydrogenase reaction, arginine in the range of at least 0 to 200 µM can be quantified.

By this method of the present invention, arginine can be selectively and solely quantified even in the presence of contaminants, such as the 19 kinds of amino acid, other than arginine, that make up proteins, urea, and ammonia. In addition, even when a test sample is contaminated with aspartic acid, the method enables selective quantification of arginine.

II. Method for Quantifying Amino Acids Using AARS

The method for quantifying an amino acid as described herein can include a step (A) of allowing an aminoacyl-tRNA synthetase (AARS) corresponding to the amino acid to act on the amino acid and adenosine triphosphate (ATP) in the presence of an (aminoacyl-AMP)-AARS complex decomposition reagent to obtain a reaction product; and a step (B) of quantifying the product generated in step (A), wherein the amount of the amino acid is determined based on the amount of the product obtained.

Amino acids that can be quantified according to the present invention include those for which a corresponding AARS exists. If an AARS is available, any kind of amino acid can be quantified according to the present invention. For example, the 20 kinds of amino acids that make up proteins, that is, L-alanine, L-cysteine, L-aspartic acid, L-glutamic acid, L-phenylalanine, glycine, L-histidine, L-isoleucine, L-lysine, L-leucine, L-methionine, L-asparagine, L-proline, L-glutamine, L-arginine, L-serine, L-threonine, L-valine, L-tryptophan, and L-tyrosine, can be quantified according to the present invention. In the present invention, although "L-" may be omitted in the descriptions of amino acids, those skilled in the art can appropriately determine whether a certain amino acid is limited to the L-isomer thereof or not, in consideration of the relation with AARS. Furthermore, in the present invention, amino acids may be indicated with the typically used three-letter codes.

Step A:

In step (A) of the aforementioned method of the present invention, an aminoacyl-tRNA synthetase (AARS) corresponding to the amino acid is allowed to act on the amino acid and adenosine triphosphate (ATP) in the presence of an (aminoacyl-AMP)-AARS complex decomposition reagent to obtain a reaction product.

AARS corresponding to the amino acid to be measured is used. If the required AARS is commercially available, such a commercial product can be used. Furthermore, those skilled in the art can appropriately prepare an AARS with available appropriate resources by using genetic engineering techniques, and so forth. For the preparation of AARS by genetic engineering techniques, typical methods for the preparation of proteins well known to those skilled in the art can be used, and AARS can be prepared by referring to the procedures and conditions described in the examples described herein.

It is known that, with GlnRS, GluRS, and ArgRS derived from *Escherichia coli*, the reaction of the aforementioned reaction formula 1 may not advance, unless the enzymes are activated by binding with tRNA. When these AARSs are used, tRNA can be added in step (A). The molar concentration of the added tRNA should not be as high as that of the amino acid to be measured, and it is sufficient for the molar concentration of the added tRNA to be as low as that of the AARS. The methods for preparing tRNA are well known to those skilled in the art (for example, the method described in "Methods of Basic Biochemical Experiments, vol. 4, Experiments for nucleic acids and genes", Ed. by Japanese Biochemical Society, etc.).

When tRNA is used, contamination of different kinds of tRNAs other than the tRNA corresponding to the subject amino acid, mRNA, and rRNA does not particularly adversely affect the reactions, and therefore a total RNA extract can be used when any of the three kinds of AARSs mentioned above are used.

The term "AARS" is not limited to AARS produced by a particular species, unless especially indicated. Any AARS can be used that can specifically or selectively act on the subject amino acid to be quantified, and can form the (aminoacyl-AMP)-AARS complex. The term "corresponding amino acid" used for AARS refers to the amino acid on which that AARS specifically or selectively acts.

AARS may be a naturally occurring AARS, or may be a modified AARS. Further, AARS used for the present invention may be a recombinant enzyme obtained by expressing a gene coding for AARS in *Escherichia coli* or other host organisms.

The method for preparing AARS is not particularly limited, and it may be a chemically synthesized protein, or a recombinant protein prepared by a gene recombination technique. When a recombinant protein is prepared, the aforementioned AARS can be prepared by obtaining a gene coding for the protein as DNA, and introducing it into an appropriate expression system. A typical preparation method can include amplifying a corresponding gene by PCR from the genomic DNA extracted from an appropriate biological species, constructing a vector consisting of a plasmid such as pET or pUC into which the gene is incorporated, then transforming a host bacterium strain such as BL21 and JM109 with the vector, and culturing the transformant. Other known methods other than the above can also be appropriately used.

An (aminoacyl-AMP)-AARS complex decomposition reagent is used. This reagent may also be simply referred to as "complex decomposition reagent".

The term "(aminoacyl-AMP)-AARS complex decomposition reagent" or "complex decomposition reagent" can refer to a reagent that can decompose the (aminoacyl-AMP)-AARS complex to regenerate AARS in the free form, unless especially indicated. In other words, it can be said that the complex decomposition reagent is a compound that can cleave the ester bond between the amino acid and AMP in the aminoacyl-AMP by a nucleophilic substitution reaction, or a compound that can dislocate the aminoacyl group to a subject other than AMP. It is preferably a concept not containing tRNA (that is, the complex decomposition reagent (except for tRNA)), and is specifically an amine or carbanion, and more specific examples thereof are dimethylamine, trimethylamine, hydroxylamine, hydrazine, and methylamine.

A preferred particular example of the complex decomposition reagent is hydroxylamine ($NH_2OH$). Hydroxylamine advances the following reaction in the present invention.

(Aminoacyl-AMP)-AARS complex+hydroxylamine→amino acid hydroxamic acid+AMP+AARS  [Equation 3]

In the aforementioned reaction, hydroxylamine causes decomposition of the (aminoacyl-AMP)-AARS complex by inducing a nucleophilic reaction at the carbon of the carboxyl group of the aminoacyl-AMP.

In the present invention, any nucleophilic reagent that can cause the same reaction as that caused by hydroxylamine, and can access the substrate pocket of the (aminoacyl-AMP)-AARS complex can be used as the complex decomposition reagent. Examples of such a reagent include hydrazine ($H_2NNH_2$) and methylamine ($CH_3NH_2$).

In step (A), adenosine triphosphate (ATP) is also used.

The reaction product of step (A) is, for example, pyrophosphate, and when hydroxylamine is used as described above, it is an amino acid hydroxamic acid.

Step B:

In step (B) of the aforementioned method of the present invention, any of the products of step (A) can be quantified.

When pyrophosphate is quantified as the product of step (A), various methods for quantifying pyrophosphate can be used. A particular example of the method for measuring pyrophosphate is a method that can be performed in the same system in which step (A) is performed.

Examples of the method for quantifying pyrophosphate that can be performed in the same system in which step (A) is performed include the method described in detail in Japanese Patent Application No. 2012-026534 and section I. of this specification; specifically, a method of generating pyruvate from pyrophosphate by using pyruvate pyrophosphate dikinase (PPDK) and quantifying pyruvate. Since the method for quantifying pyruvate using PPDK can be performed also in the presence of ATP, it can be coupled with a reaction catalyzed by an enzyme that generates pyrophosphate by using ATP together with a subject substance as substrates (specifically AARS in this case) (as sequential reactions catalyzed by two or more kinds of enzymes, especially sequential reactions in which a product generated with one enzyme is used as a substrate for another enzyme). Furthermore, AARS shows high substrate specificity, and high reactivity based on the ATP hydrolysis as an exoergic reaction. The embodiment of the present invention in which AARS and PPDK are coupled can enjoy such advantages.

Specific examples of the method for quantifying pyruvate include (1) a method of reacting pyruvate with lactate dehydrogenase (LDH) (refer to Example 6, 8.), and (2) a method of reacting pyruvate with pyruvate oxidase and peroxidase. These methods for quantifying pyrophosphate have characteristics that they are not affected by the presence of inorganic phosphoric acid or ATP, and can regenerate ATP as the substrate of AARS from AMP. PPDK, LDH, pyruvate oxidase, and peroxidase catalyze the reactions shown below, respectively.

PPDK: Pyrophosphate+phosphoenolpyruvate+
AMP→pyruvate+ATP+inorganic phosphoric
acid LDH: Pyruvate+NADH→lactate+$NAD^+$ Pyruvate oxidase: Pyruvate+phosphoric acid+$O_2$+
$H_2O$→acetyl phosphate+carbon dioxide+$H_2O_2$ Peroxidase: $2H_2O_2$+4-aminoantipyrine+phenol→quinoneimine dye+$4H_2O$  [Equation 4]

Examples of the method for quantifying pyrophosphate other than the above include a method of converting pyrophosphate into inorganic phosphoric acid by a reaction with pyrophosphatase, and quantifying inorganic phosphoric acid by any of various methods. Examples of the method for quantifying inorganic phosphoric acid include, for example, the molybdenum blue method (refer to Example 6, 9.). This is a method of spectrophotometrically quantifying a dye generated by a reaction of phosphoric acid with ammonium molybdate and a reducing agent under an acidic condition. Pyrophosphatase catalyzes the reaction shown below.

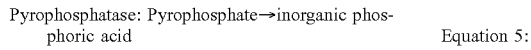

Equation 5:

As a method for quantifying pyrophosphate other than the above, a method of generating ATP from pyrophosphate with an enzymes such as ATP sulfurylase, and quantifying ATP by using luciferase or the like is known. However, in this pyrophosphate quantification method, the amount of pyrophosphate may be overestimated due to ATP added as the substrate of AARS, and the reaction catalyzed by AARS may not advance due to depletion of ATP caused by luciferase or the like. Therefore, when such a method for quantifying pyrophosphate based on ATP production as described above is used for the AARS-coupled system according to the present invention, special consideration will be required. ATP sulfurylase catalyzes the reaction shown below.

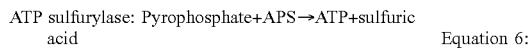

Equation 6:

Examples of the reaction product of step (A) that is measurable in step (B) include a decomposition product of the (aminoacyl-AMP)-AARS complex. For example, when hydroxylamine is used as the complex decomposition reagent, an amino acid hydroxamic acid and AMP are generated as decomposition products, and any of these may be measured. AMP can be quantified by using, for example, HPLC. Hydroxamic acid can be photospectrometrically quantified by, for example, reacting it with ferric chloride under an acidic condition, and measuring absorbance at 540 nm.

Reaction Conditions:

The amount of AARS used in step (A) is not particularly limited so long as the quantification of pyrophosphate is enabled, and can be appropriately determined according to amount of pyrophosphate contained in a sample, apparatus to be used, purity and type of PPDK. When it is desired to complete the reaction within several tens of minutes, the amount of AARS to be used can be, at a minimum, 0.05 mU/ml or more, 0.1 mU/ml or more, 0.5 mU/ml or more. When it is desired to advance the reaction more quickly, a larger amount can be used. Furthermore, the maximum amount may be determined from an economical point of view etc., and it may be 10 U/ml or less, 5 U/ml or less, or 1 U/ml or less. Concentrations of components in a reaction system mentioned in the present invention are final concentrations in the system, unless especially indicated.

AARS is regenerated by the use of the complex decomposition reagent. Therefore, the amount of AARS may be such an amount that AARS can function as an enzyme, and may be less than the amount of the subject amino acid to be quantified. According to the study of the inventors of the present invention, 200 μM of Tyr could be quantified in the presence of 2 μM of TyrRS. Therefore, the method of the present invention can be performed with a comparatively small amount of AARS, and can be as small as not larger than μM order, or as small as a molar concentration of 1% or lower with respect to the amino acid.

In step (A), the complex decomposition reagent is used. When hydroxylamine is used as the complex decomposition reagent (when it is described that hydrazine is used as the complex decomposition reagent in the present invention, it also means use of hydrazine as a salt, and the same shall apply to use of other complex decomposition reagents), and it is desired to complete the reaction within several tens of minutes, the concentration thereof can be, at a minimum, 5 mM or higher, 50 mM or higher, 400 mM or higher. If the reaction time is prolonged, the reaction may be performed with a smaller amount of the regent. Furthermore, in any case, the maximum amount may be determined from the viewpoints of safety of handling, economy, etc., and it may be 8000 mM or lower, 4000 mM or lower, or 2000 mM or lower.

According to the study of the inventors of the present invention, it was confirmed that when hydrazine or methylamine is used as the complex decomposition reagent, amino acids can be quantified with a final concentration thereof of 400 mM or 20 mM in the reaction system, respectively. Therefore, when these complex decomposition reagents are used, the quantification will be favorably performed by using them at a concentration 1/100 time or more, more specifically 1/10 time or more, of the concentration confirmed to be effective. In any case, the maximum amount may be determined from the viewpoints of safety of handling, economy, etc., and it may be 8000 mM or lower, 4000 mM or lower, or 2000 mM or lower.

Furthermore, when a complex decomposition reagent showing a comparatively high reactivity is chosen, adverse effects can be avoided by adding it to the reaction system immediately before the reaction. Those skilled in the art will be able to easily design step (A) also in consideration of such a point. According to the study of the inventors of the present invention, when hydroxylamine was used, any problematic influence was not seen about 10 minutes after hydroxylamine was mixed with the other components.

The amount of ATP used in step (A) can be appropriately determined by those skilled in the art in consideration of concentrations of the other components and reaction conditions. Since a concentration of ATP higher than that of the amino acid to be measured is usually required in step (A), the concentration of ATP should be at least 5 μM, which is the lower limit of the amino acid concentration measurable according to the present invention, or higher.

When step (A) and step (B) using pyruvate pyrophosphate dikinase (PPDK) are performed in the same system, theoretically, the concentration of ATP may be lower than that described above. From this point of view, the concentration of ATP can be, at a minimum, 0.002 mM or higher, 0.02 mM or higher, or 0.2 mM or higher.

In any case, as for the maximum concentration, the concentration of ATP may be 200 mM or lower, 20 mM or lower, or 2 mM or lower.

When step (B) is performed as a step for measuring pyrophosphate in the same system in which step (A) is performed, then pyruvate is generated from pyrophosphate with pyruvate pyrophosphate dikinase (PPDK), and pyruvate is reacted with lactate dehydrogenase (LDH) in this step (referred to as "step (B1)"), the amount of PPDK to be used is not particularly limited so long as the quantification of pyrophosphate is enabled, and can be appropriately determined according to amount of pyrophosphate contained in a sample, apparatus to be used, purity and type of PPDK. The amount of PPDK to be used can be, at a minimum, 0.001 U/ml or more, 0.005 U/ml or more, or 0.01 U/ml or more. Furthermore, at a maximum concentration, the PPDK concentration can be 10 U/ml or less, 5 U/ml or less, 1 U/ml or less.

The step (B1) is performed in the presence of a high energy phosphate compound such as PEP. The concentration of PEP can be, at a minimum, 0.01 mM or higher, 0.025 mM or higher, or 0.05 mM or higher. Furthermore, at a maximum, is the PEP concentration can be 20 mM or lower, 10 mM or lower, 5 mM or lower.

The step (B1) is performed in the presence of AMP. The concentration of AMP can be, at a minimum, 0.01 mM or higher, 0.025 mM or higher, or 0.05 mM or higher. Furthermore, at a maximum, the AMP concentration can be 20 mM or lower, 10 mM or lower, 5 mM or lower.

The step (B1) can be performed in the presence of a metal ion. The metal ion may be any of magnesium ion, cobalt ion, and manganese ion, and magnesium ion is particular example. The amount of the metal ion to be used can be, at a minimum, for example, magnesium ion, 0.1 equivalent or more, 0.2 equivalent or more, 0.4 equivalent or more, with respect to the concentration of AMP. Furthermore, at a maximum, the concentration of the metal ion can be 10 equivalents or less, 5 equivalents or less, or 2.5 equivalents or less. The most preferred concentration is 0.5 to 2 equivalents, for example, 1 equivalent, of the phosphate donor.

The amount of the lactate dehydrogenase used in the step (B1) is not particularly limited so long as the quantification of pyrophosphate is enabled, and can be appropriately determined according to amount of pyrophosphate contained in a sample, apparatus to be used, purity and type of the enzyme. The amount of the enzyme to be used can be, at a minimum, 0.002 U/ml or more, 0.005 U/ml or more, or 0.01 U/ml or more. Furthermore, at a maximum, the enzyme concentration can be 4 U/ml or less, 2 U/ml or less, 1 U/ml or less.

The step (B1) can also be performed in the presence of NADH. Influence of the NADH concentration is comparatively significant, for example if the NADH concentration is unduly low, detection of absorbance is difficult, and if it is unduly high, accuracy of the measured value of decrease of the NADH concentration is degraded. The concentration of NADH can be, at a minimum, 0.01 mM or higher, 0.02 mM or higher, 0.05 mM or higher. In any case, at a maximum, the NADH concentration can be 4 mM or lower, 2 mM or lower, 1 mM or lower.

In step (B1), the decrease of the NADH amount that occurs as the reaction progresses is measured by measuring the absorbance at 340 nm, and the amount of generated pyruvate can be calculated.

When step (B) is performed as a step for measuring pyrophosphate, in which pyrophosphate is converted into inorganic phosphoric acid by the reaction with pyrophosphatase, and inorganic phosphoric acid is quantified by any of various methods (referred to as "step (B2)"), the amount of pyrophosphatase to be used is not particularly limited so long as the quantification of pyrophosphate is enabled, and can be appropriately determined according to amount of pyrophosphate contained in a sample, apparatus to be used, purity and type of pyrophosphatase. The amount of pyrophosphatase to be used can be, at a minimum, 0.151 U/ml or more, 1.5 U/ml or more, 15 U/ml or more. Furthermore, at a maximum, the amount of pyrophosphate can be 6000 U/ml or less, 600 U/ml or less, or 60 U/ml or less. As the color developing reagent, a solution prepared by mixing water and concentrated sulfuric acid, dissolving $(NH_4)_6Mo_7O_{24}$ in the mixture, mixing water and concentrated sulfuric acid with the solution, and dissolving $FeSO_4$ in the mixture can be used (molybdenum blue method). As for the examples of the color developing reagent, the example section of this specification can be referred to.

The reaction temperature for the steps (A) and (B) can be appropriately set in consideration of the optimum temperature for the enzyme to be used, and so forth. When such enzymes as shown in the examples of this specification are used, these steps can be appropriately performed at room temperature to 37° C. Also when step (A) and step (B) for measuring pyrophosphate using PPDK are simultaneously advanced in the same system, the reaction temperature is appropriately determined in consideration of the optimum temperature for the enzyme to be used, and so forth, and it can be appropriately performed at room temperature to 37° C., for example, 30° C.

Although the reaction times of the steps (A) and (B) depend on the amount of amino acid present in a test sample or amount of AARS to be used, the reaction promptly advances, and the reaction time may be 40 minutes or shorter, for example, about 20 minutes or shorter.

According to one of the embodiments of the present invention, AARS derived from a thermophile is used as the AARS used in step (A). Examples of the thermophile include organisms belonging to the genus *Thermus*. It is considered that such an embodiment has advantages that the reaction can be performed at a relatively high temperature, and the enzyme may be used in a small amount, because the reaction is performed at a high temperature. Although those skilled in the art can appropriately determine the reaction temperature for such an embodiment depending on the AARS to be used, it is, for example, 50° C. or higher, 60° C. or higher, or 65° C. or higher. The amount of AARS may be ½ or less, ⅕ or less, or ⅛ or less, of the amount described above.

When step (A) is performed at a relatively high temperature, an example of step (B) that can be combined is the molybdenum blue method described above as the step (B2).

III. Use of the Present Invention Etc.

It is known that methionine accumulates in homocystinuria patients at high concentration, and therefore methionine serves as an important biomarker for clinical mass screening for the disease. Furthermore, citrulline is an amino acids that exists in the body, and contributes to blood flow promotion, immunity activation, and so forth. Because of the efficacies thereof, citrulline is widely used for foods and drugs such as supplements. Further, citrulline is also one of the metabolites in the urea cycle, and is considered to be important as a biomarker for detecting metabolic abnormality in the urea cycle of human bodies, including citrullinuria. Furthermore, arginine is an amino acid found in proteins, and is one of the important constituents present in foods and drugs. Arginine is also one of the metabolites in the urea cycle, and is considered to be important as a biomarker for detecting metabolic abnormality in the urea cycle of human bodies, including arginase deficiency. For these purposes, the present invention can be used for quantifying a subject substance.

The method for quantifying pyrophosphate, the method for quantifying methionine, the method for quantifying citrulline, and the method for quantifying arginine of the present invention enable accurate quantification of each subject substance even in the presence of contaminants derived from various biological origins. Therefore, the methods of the present invention can be applied to samples of biological origins, for example, blood, blood serum, plasma, urine, and sweat. The methods of the present invention are especially suitable for quantification in a sample derived from blood. Although the present invention may be explained for the method for quantifying pyrophosphate as an example, the explanations therefor are applied to the method for quantifying methionine, the method for quantifying citrulline, and the method for quantifying arginine, unless especially explained.

The methods of the present invention can be used for identification or quantification of a comparatively small amount of subject substances. The methods of the present invention can be performed in a system having a volume of several tens to several hundreds of microliters. When it is intended to perform the methods of the present invention for a blood sample, the blood sample may be plasma, blood serum, or dried filter paper blood. The dried filter paper blood may be, for example, blood extracted from the heel of neonate and impregnated in filter paper for exclusive use for blood collection in a sufficient volume, and such a sample is especially useful for mass screening of neonates. Specific conditions of the methods for dried filter paper blood as the object can be appropriately designed by those skilled in the art by referring to the conditions for the existing methods for such mass screening.

The present invention also provides kits or commercial packages for use in a method for quantifying pyrophosphate, method for quantifying methionine, method for quantifying citrulline, and method for quantifying arginine. The kits or packages of the present invention comprise a unit including each or any combination of the aforementioned components in the aforementioned concentration ranges preferably together with a material on which use and directions of the kits are described (box, package, label, instruction for use, etc.).

By the present invention, there is provided simple and quick methods for quantifying at least methionine, citrulline, and arginine. The multivariate analysis of concentrations of a plurality of kinds of amino acids attracts attention for use in test and diagnosis for determining presence or absence of a disease, and health condition. The quantification methods of the present invention can also be used for such analysis.

By the methods of the present invention using AARS, an amino acid existing at a concentration of 5 to 200 μM can be quantified.

The methods of the present invention can be used for quantifying an amino acid in a sample. The sample may be any sample so long as it is a sample that may contain an amino acid as the subject of measurement, and the methods can be applied to, for example, samples of biological origins such as blood, blood serum, plasma, urine, and sweat. Further, they can also be applied to foods, cosmetics, drugs, and so forth.

The sample may contain two or more kinds of amino acids, and each of the amino acids can be quantified according to the present invention. When two or more kinds of amino acids contained in one sample are quantified, the method of the present invention includes the steps of preparing AARSs corresponding to the respective subject amino acids, preparing a reaction reagent containing the other required components other than AARS, mixing the reaction reagent and a sample, dividing the mixture into samples at least in the number of the types of the subject amino acids, and adding different AARSs to the divided samples, respectively.

The methods of the present invention enable quick and simultaneous quantification of a plurality of amino acids.

EXAMPLES

The present invention will be specifically explained below with reference to the following non-limiting examples.

Example 1

1. Example of Preparation of Enzymes
1-1. Construction of PPDK Expression Plasmids
Plasmids for expression of PPDK derived from the *Propionibacterium freudenreichii* subsp. *shermanii* NBRC 12426 strain (PfPPDK) and PPDK derived from the *Thermoproteus tenax* NBRC 100435 strain (TtPPDK) were constructed. Genomic DNA was prepared from cells of each strain.

The gene of PfPPDK was amplified by PCR performed by using the genomic DNA obtained above as the template, and primers (SEQ ID NOS: 2 and 3) designed on the basis of the PPDK gene sequence (SEQ ID NO: 1) obtained from a database. The amplification product was inserted into pET-28a to obtain a plasmid for expression of PfPPDK. The gene of TtPPDK was amplified by PCR performed by using the genomic DNA obtained above as the template, and primers (SEQ ID NOS: 5 and 6) designed on the basis of the PPDK gene sequence (SEQ ID NO: 4) obtained from a database. The amplification product was inserted into pET-28a to obtain a plasmid for expression of TtPPDK.

Sequencing of each expression plasmid was performed to confirm the nucleotide sequence. The sequences were compared with those of the genes found in the database, and sequences of sites where non-conservative substitution occurred were corrected by using QuikGene Kit, so that a translation product of the same sequence as that of the database could be obtained.

1-2. Construction of AdoMetS Expression Plasmid
Genomic DNA was prepared from the *Escherichia coli* W3110 strain cells. By using this DNA as the template and primers (SEQ ID NOS: 8 and 9) designed on the basis of the AdoMetS gene sequence (SEQ ID NO: 7) found in a database, PCR was performed to amplify the AdoMetS gene. The amplification product was inserted into pET-28a to obtain a plasmid for expression of AdoMetS.

1-3. Construction of ASS Expression Plasmid
By using the aforementioned genomic DNA of the *Escherichia coli* W3110 strain as the template and primers (SEQ ID NOS: 11 and 12) designed on the basis of the ASS gene sequence (SEQ ID NO: 10) found in a database, PCR was performed to amplify the ASS gene. The amplification product was inserted into pET-28a to obtain a plasmid for expression of ASS.

1-4. Construction of ADI Expression Plasmid
Genomic DNA was prepared from the *Pseudomonas aeruginosa* PAO1 strain cells. By using this DNA as the template and primers (SEQ ID NOS: 14 and 15) designed on the basis of the ADI gene sequence (SEQ ID NO: 13) found in a database, PCR was performed to amplify the ADI gene. The amplification product was inserted into pET-28a to obtain a plasmid for expression of ADI.

1-5. Expression and Purification of Enzymes
The *Escherichia coli* BL21 (DE3) strain was transformed with each of the expression plasmids, and used as overexpression strains.

Each expression strain was cultured at 37° C. with shaking until $OD_{600}$ became 0.6 to 0.8, and the expression was induced by adding IPTG at a final concentration of 0.5 mM. After the induction of expression, the PPDK and ADI expression strains were cultured at 30° C., and the AdoMetS and ASS expression strains were cultured at 37° C. each for 4 hours with shaking, and then the cells were collected. The cells were disrupted by ultrasonication, and the subject enzyme was obtained in a soluble fraction.

The supernatant of the cell disruption suspension of each expression strain was loaded on a Ni Sepharose column produced by GE Healthcare, washed with a 20 mM Tris-HCl, 50 mM imidazole solution, and eluted with the 20 mM Tris-HCl, 500 mM imidazole solution to purify and collect the subject enzyme. The above enzyme solutions were subjected to dialysis or ultrafiltration to eliminate imidazole or change the buffer, if needed, and then used.

When each purified enzyme solution was mixed with glycerol at a final concentration of 20%, and the mixture was cryopreserved at −80° C., stable long-term storage of the enzyme was possible.

Example 2

2. Example of Quantification of Pyrophosphate 2-1. Example of Reaction Conditions for Quantification of Pyrophosphate (1)

A test sample containing pyrophosphate and a reaction mixture for quantifying pyrophosphate having the following composition were mixed. The mixture was maintained at 30° C. to allow the reaction to advance, and decrease of the absorbance at 340 nm was measured. The volume of the mixture was 1 ml or 200 μl. The measurement of the absorbance was performed with a cuvette having an optical path length of 1 cm and absorptiometer for the former volume, or with a microplate and a microplate reader (optical path length is not fixed) for the latter volume. In the graphs shown in the drawings, the absorbance measured with a cuvette having an optical path length of 1 cm is indicated as Abs, and the absorbance measured with a microplate is indicated as AU.

Reaction mixture for quantifying pyrophosphate: 20 mM imidazole-HCl (pH 7.0), 5 mM $MgCl_2$, 0.5 mM PEP, 0.5 mM AMP, 0.25 mM NADH, 0.1 U/ml PPDK, and 0.5 U/ml lactate dehydrogenase (derived from rabbit muscle, Oriental Yeast) (concentrations are final concentrations obtained after mixing with test sample)

2-2. Example of Reaction Conditions for Quantification of Pyrophosphate (2)

A test sample containing pyrophosphate and a reaction mixture for quantifying pyrophosphate having the following composition were mixed. The mixture in a volume of 200 μl was maintained at 30° C. to allow the reaction to advance, and increase of the absorbance at 505 nm was measured with a microplate reader.

Reaction mixture for quantifying pyrophosphate: 20 mM imidazole-HCl (pH 7.0), 5 mM $MgCl_2$, 10 mM $NH_4Cl$, 0.5 mM PEP, 0.5 mM AMP, 0.1 U/ml PPDK, 0.5 mM Na—$PO_4$, 1 mM 4-aminoantipyrine, 1 mM phenol, 1.5 U/ml pyruvate oxidase (PYRUVATE OXIDASE from Microorganism (Diagnostic Reagent Grade) TOYOBO ENZYMES), and 7.5 U/ml peroxidase (concentrations are final concentrations obtained after mixing with test sample)

2-3. Example of Reaction Conditions for Quantification of Pyrophosphate (3)

A test sample containing pyrophosphate and a reaction mixture for quantifying pyrophosphate having the following composition were mixed. The mixture in a volume of 200 μl was maintained at 30° C. to allow the reaction to advance, and increase of the fluorescence at 590 nm (excitation, 530 nm) was measured with a microplate reader.

Reaction mixture for quantifying pyrophosphate: 20 mM imidazole-HCl (pH 7.0), 5 mM $MgCl_2$, 10 mM $NH_4Cl$, 0.5 mM PEP, 0.5 mM AMP, 0.1 U/ml PPDK, 0.5 mM Na—$PO_4$, 50 μM ADHP, 1.5 U/ml pyruvate oxidase, and 7.5 U/ml peroxidase (concentrations are final concentrations obtained after mixing with test sample)

2-4. Example of Preparation of Calibration Curve for Quantification of Pyrophosphate Whether a calibration curve could be created was verified by using pyrophosphate standard solutions of various concentrations as test samples.

Figure 1B:
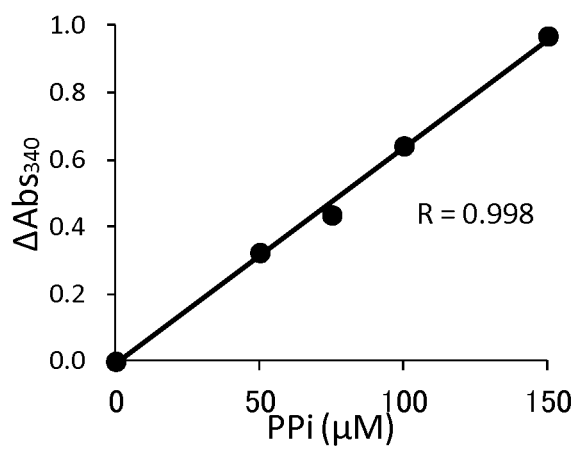

By using the reaction conditions of Example 2-1, the measurement was performed with a cuvette having an optical path length of 1 cm and an absorptiometer. The reaction was completed 10 minutes after the mixing, and the calibration curves shown in FIGS. 1A and 1B were obtained with the systems using PfPPDK and TtPPDK, respectively. The linearity of the calibration curves is high, and thus it was demonstrated that pyrophosphate can be quantified by this method at least in the range of 0 to 200 μM. Further, inclinations of the calibration curves are 6.0 $mM^{-1}.cm^{-1}$ and 6.4 $mM^{-1}.cm^{-1}$ for the cases of using PfPPDK and TtPPDK, respectively, which are substantially equivalent to the molar absorption coefficient of NADH (6.2 $mM^{-1}.cm^{-1}$). Therefore, it was demonstrated that a substantial amount of pyrophosphate in the test sample was used for oxidation of NADH.

Figure 2:
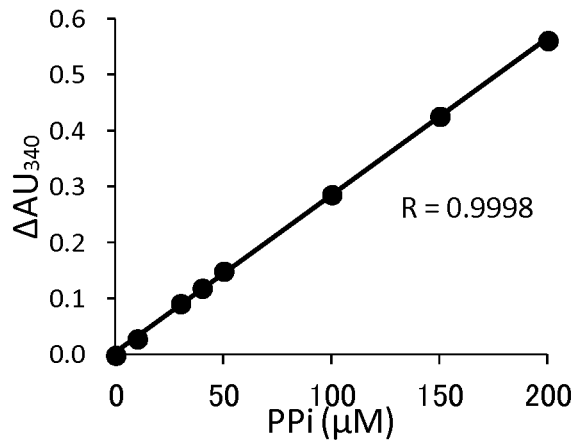
FIG. 2 is a graph showing a pyrophosphate calibration curve when using lactate dehydrogenase (for measurement with microplate reader).

When the reaction was performed by using PfPPDK with the reaction conditions described in Example 2-1, and the measurement was performed with a microplate and a microplate reader, the results were as shown in FIG. 2. A calibration curve of high linearity was obtained as in the case of using an absorptiometer, and thus it was demonstrated that the quantification of pyrophosphate with this method can also be performed with a microplate reader.

Figure 3:
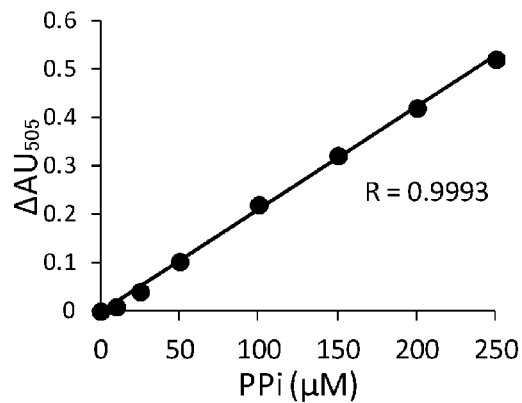
FIG. 3 is a graph showing a pyrophosphate calibration curve when using pyruvate oxidase and a color developing dye.

When the reaction and the measurement were performed by using PfPPDK with the reaction conditions described in Example 2-2, such a calibration curve as shown in FIG. 3 was obtained. A calibration curve of high linearity was obtained as in Example 2-1, and thus it was demonstrated that this method can also be used in a color developing system using 4-aminoantipyrine.

Figure 4:
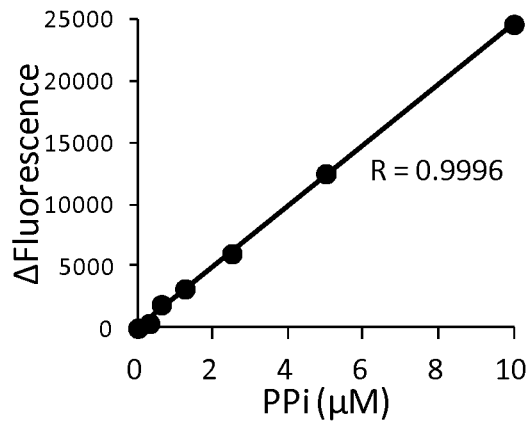
FIG. 4 is a graph showing a pyrophosphate calibration curve when using pyruvate oxidase and a fluorescent dye.

When the reaction and the measurement were performed by using PfPPDK with the reaction conditions described in Example 2-3, such a calibration curve as shown in FIG. 4 was obtained. High linearity of the calibration curve was obtained for the pyrophosphate concentrations in the range of 0 to 10 μM, and thus it was demonstrated that even a low concentration of pyrophosphate can be quantified with high sensitivity by using a fluorescent dye such as ADHP.

2-5. Quantification of Pyrophosphate in the Presence of Phosphoric Acid or ATP

In order to verify whether this quantification system can also be used in the presence of phosphoric acid or ATP, it was verified whether a calibration curve could be prepared for pyrophosphate by using any of the following three kinds of solutions as test samples.

Pyrophosphate standard solutions of various concentrations

Pyrophosphate standard solutions of various concentrations and 0.3 mM phosphoric acid standard solution (concentration is the final concentration obtained after mixing with reaction mixture)

Pyrophosphate standard solutions of various concentrations and 0.3 mM ATP standard solution (concentration is the final concentration obtained after mixing with reaction mixture)

Figure 5:
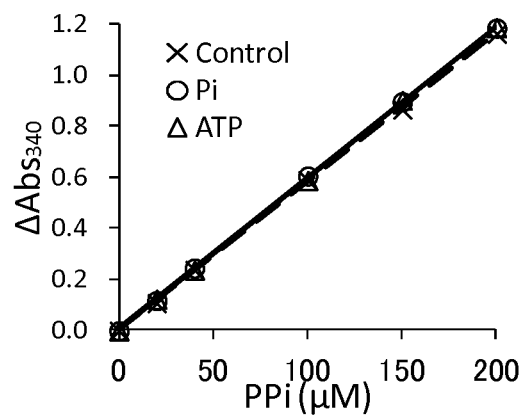
FIG. 5 is a graph showing pyrophosphate calibration curves created with reaction mixtures containing phosphoric acid or ATP.

The reaction conditions were those described in Example 2-1, and PfPPDK was used as PPDK. The measurement was performed with each of the aforementioned three kinds of samples, and as a result, such calibration curves as shown in FIG. 5 were obtained. There was observed no significant difference in absorbance values for various concentrations of pyrophosphate or inclinations of the calibration curves for the three kinds of conditions due to the presence of phosphoric acid or ATP. Therefore, it was demonstrated that this pyrophosphate quantification system is not influenced by the presence of phosphoric acid or ATP, and enables the quantification even in the presence of them.

2-6. Example of Addition and Collection of Pyrophosphate in Biological Sample

In order to verify whether this quantification system can also be used for a biological sample, it was verified whether a calibration curve can be prepared for pyrophosphate by using each of the following two kinds of solutions as test samples.

Pyrophosphate standard solutions of various concentrations

Pyrophosphate standard solutions of various concentrations and 50% human blood plasma (concentration is the final concentration obtained after mixing with reaction mixture)

Figure 6:
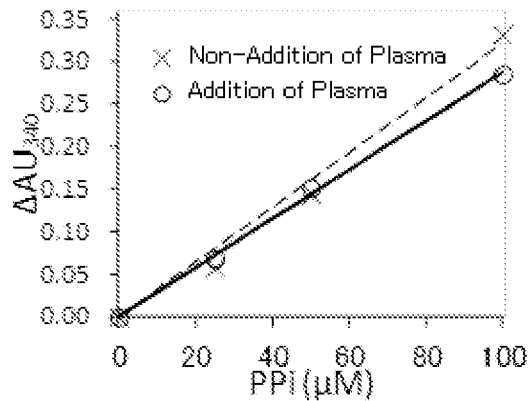
FIG. 6 is a graph showing results of a test performed by adding pyrophosphate to a biological sample.

The reaction conditions were those described in Example 2-1, and PfPPDK was used as PPDK. The measurement was performed with each of the aforementioned two kinds of samples, and as a result, such calibration curves as shown in FIG. 6 were obtained. There was observed no significant difference in absorbance values for various concentrations of pyrophosphate or inclinations of the calibration curves for the two kinds of conditions due to the presence of the human plasma. Therefore, it was demonstrated that this pyrophosphate quantification system is not influenced by the presence of human plasma, and enables the quantification even in a biological sample.

Example 3

3. Example of Quantification of Methionine 3-1. Example of Reaction Conditions for Quantification of Methionine A test sample containing methionine and a reaction mixture for quantifying methionine having the following composition were mixed. The mixture in a volume of 200 µl was maintained at 30° C. to allow the reaction to advance, and decrease of the absorbance at 340 nm was measured with a microplate reader.

Reaction mixture for quantifying methionine: 20 mM imidazole-HCl (pH 7.0), 5 mM $MgCl_2$, 1 mM ATP, 0.5 mM PEP, 0.4 mM AMP, 0.25 mM NADH, 0.1 U/ml PfPPDK, 0.5 U/ml lactate dehydrogenase, and 0.2 U/ml AdoMetS (concentrations are final concentrations obtained after mixing with test sample)

Figure 7:
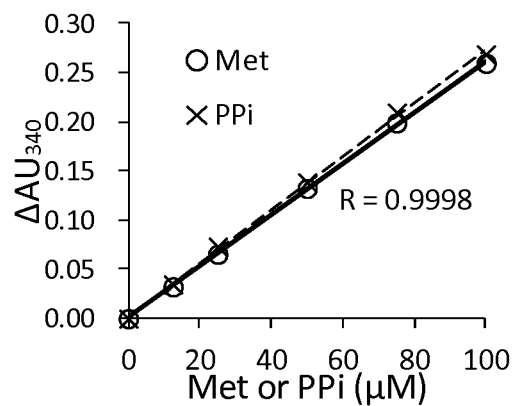
FIG. 7 is a graph showing a methionine calibration curve.

3-2. Example of Preparation of Calibration Curve for Quantification of Methionine As test samples, standard methionine solutions and standard pyrophosphate solutions giving final concentrations of 0 to 100 µM after mixing with the reaction mixture were used. Plotting results of the methionine or pyrophosphate final concentrations versus absorbance differences of the samples are shown in FIG. 7. A calibration curve of high linearity was also obtained with samples containing methionine, as in the case of samples containing pyrophosphate, and thus it was demonstrated that methionine quantification is enabled with this reaction mixture. Further, inclinations of the methionine calibration curve and the pyrophosphate calibration curve were substantially the same, and thus it was demonstrated that substantially all methionine in the reaction mixture was converted into pyrophosphate and used for the reaction.

3-3. Reactivity with Various Amino Acids and Ammonia

As test samples, various amino acids and $NH_4Cl$ were used at a concentration giving a final concentration of 200 µM after mixing with the reaction mixture. As the amino acids, 19 kinds of the amino acids constituting proteins other than methionine were used.

As a result of the measurement, test sample-dependent absorbance change was not observed for all the samples. This result demonstrated that this quantification system does not show reactivity with the amino acids constituting proteins other than methionine and ammonia, and enables highly selective methionine quantification.

Example 4

4. Example of Quantification of Citrulline 4-1. Example of Reaction Conditions for Quantification of Citrulline There was prepared a reaction mixture containing 20 mM imidazole-HCl (PH 7.0), 5 mM $MgCl_2$, 2 mM aspartic acid, 2 mM PEP, 1 mM ATP, 0.25 mM AMP, 0.25 mM NADH, 0.1 U/ml PfPPDK, 0.5 U/ml lactate dehydrogenase, 0.2 U/ml ASS, and 0 to 200 µM citrulline as final concentrations. The mixture in a volume of 200 µl was maintained at 30° C. to allow the reaction to advance, and decrease of the absorbance at 340 nm was measured with a microplate reader.

Figure 8:
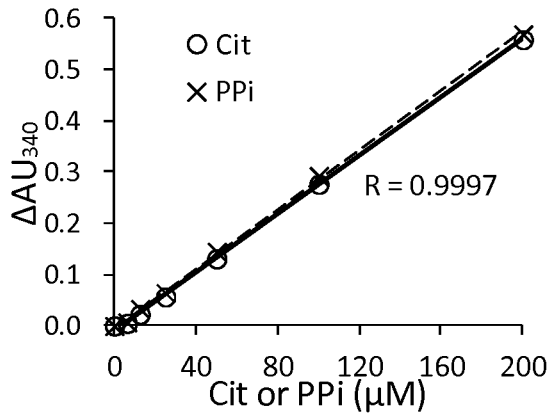
FIG. 8 is a graph showing a citrulline calibration curve.

4-2. Example of Preparation of Calibration Curve for Quantification of Citrulline As test samples, standard citrulline solutions and standard pyrophosphate solutions giving final concentrations of 0 to 200 µM after mixing with the reaction mixture were used. Plotting results of the citrulline or pyrophosphate final concentrations versus the absorbance differences of the samples are shown in FIG. 8. A calibration curve of high linearity was also obtained with samples containing citrulline, as in the case of samples containing pyrophosphate, and thus it was demonstrated that citrulline quantification is enabled with this reaction mixture. Further, inclinations of the citrulline calibration curve and the pyrophosphate calibration curve were substantially the same, and thus it was demonstrated that substantially all citrulline in the reaction mixture was converted into pyrophosphate and used for the reaction.

4-3. Reactivity with Various Amino Acids and Urea

As test samples, various amino acids and urea were used at a concentration giving a final concentration of 200 µM after mixing with the reaction mixture. As the amino acids, 19 kinds of the amino acids constituting proteins other than aspartic acid were used.

As a result of the measurement, test sample-dependent absorbance change was not observed for all the samples. This result demonstrated that this quantification system does not show reactivity with the amino acids constituting proteins other than citrulline and urea, and enables highly selective quantification of citrulline.

Example 5

5. Example of Quantification of Arginine 5-1. Example of Reaction Conditions for Quantification of Arginine There was prepared a reaction mixture containing 20 mM imidazole-HCl (PH 7.0), 5 mM $MgCl_2$, 2 mM aspartic acid, 2 mM PEP, 1 mM ATP, 0.25 mM AMP, 0.25 mM NADH, 0.1 U/ml PfPPDK, 0.5 U/ml lactate dehydrogenase, 0.2 U/ml ASS, 0.2 U/ml ADI, and 0 to 200 µM arginine as final concentrations. The mixture in a volume of 200 µl was maintained at 30° C. to allow the reaction to advance, and decrease of the absorbance at 340 nm was measured with a microplate reader.

5-2. Example of Preparation of Calibration Curve for Quantification of Arginine

Figure 9:
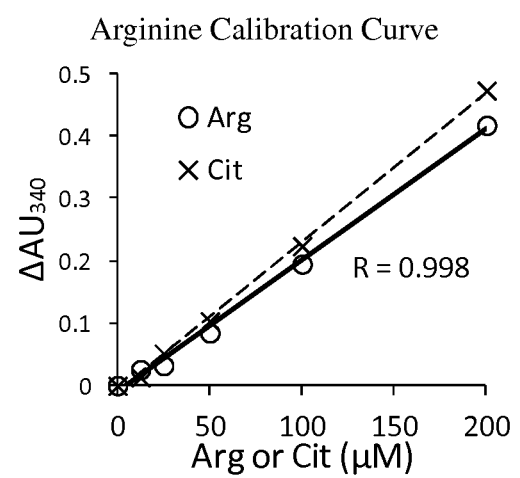
FIG. 9 is a graph showing an arginine calibration curve.
Figure 10A:
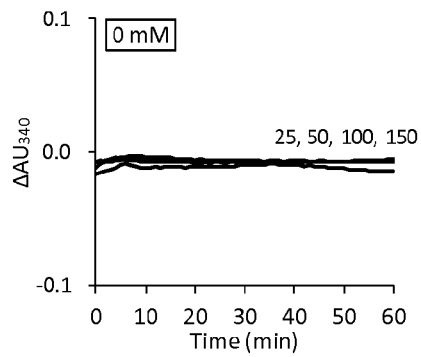
FIGS. 10A-10H show temporal change of absorbance in Tyr quantification reaction mixtures at the time of adding various concentrations of hydroxylamine (0, 50, 100, 200, 400, 600, 800, and 1000 mM). The numbers in the graphs (25, 50, 100, and 150) represent Tyr concentrations (µM) in the reaction mixtures. The horizontal axes represent time after the start of the measurement, and the vertical axes represent difference of absorbance compared with that observed for a no Tyr addition sample. The results were obtained by preparing one sample for each reaction mixture, and performing the measurement with it.
Figure 10B:
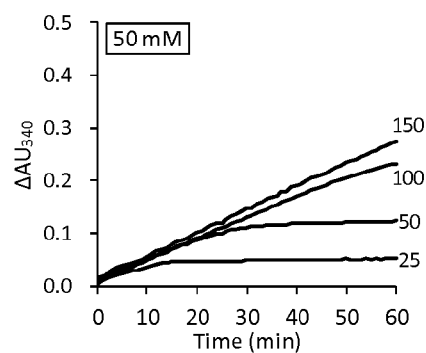
Figure 10C:
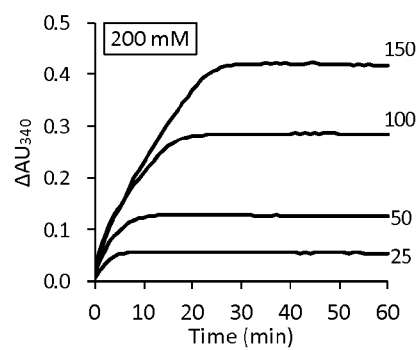
Figure 10D:
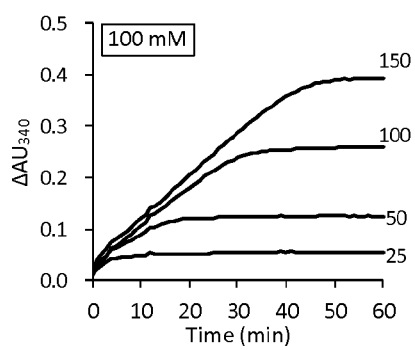
Figure 10E:
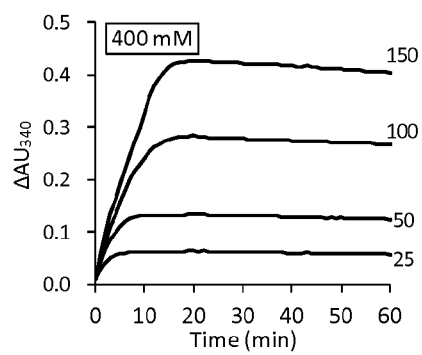
Figure 10F:
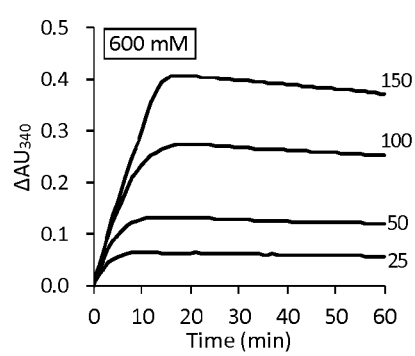
Figure 10G:
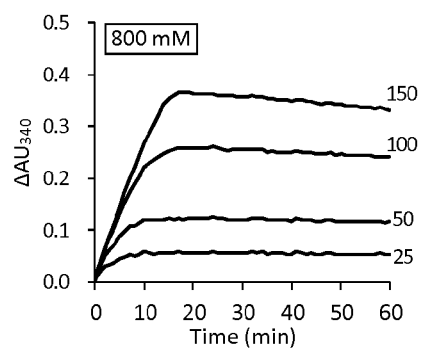
Figure 10H:
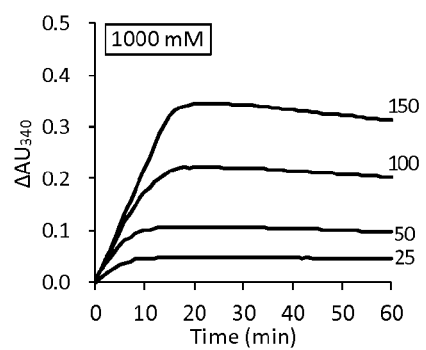

As test samples, standard arginine solutions or standard citrulline solutions giving final concentrations of 0 to 200 µM after mixing with the reaction mixture were used. Plotting results of the arginine or citrulline final concentrations versus the absorbance differences of the samples are shown in FIG. 9. A calibration curve of high linearity was also obtained with samples containing arginine, as in the case of samples containing citrulline, and thus it was demonstrated that arginine quantification is enabled with this reaction mixture. Further, difference of inclinations of the arginine calibration curve and the citrulline calibration curve was about 10%, and thus it was demonstrated that substantially all arginine in the reaction mixture was converted into citrulline and used for the reaction.

5-3. Reactivity with Various Amino Acids and Urea

As test samples, various amino acids, ammonia and urea were used at a concentration giving a final concentration of 200 µM after mixing with the reaction mixture. As the amino acids, 18 kinds of the amino acids constituting proteins other than arginine and aspartic acid were used.

As a result of the measurement, any test sample-dependent absorbance change was not observed for all the samples. This result demonstrated that this quantification system does not show reactivity with the amino acids constituting proteins other than arginine and citrulline and urea, and enables highly selective quantification of arginine.

Example 6

6. Construction of AARS Expression Systems

Expression systems for heterogenous expression of CysRS, HisRS, LysRS, ProRS, SerRS, TrpRS, and TyrRS derived from the *Thermotoga maritima* MSB8 strain (NBRC 100826) in *Escherichia coli* were constructed as follows.

PCR was performed by using the genomic DNA of the T maritima strain provided by NBRC as the template and primers (SEQ ID NOS: 23 to 36) designed on the basis of the various AARS gene sequences (SEQ ID NOS: 16 to 22) found in a database to amplify each gene. The amplification products were each inserted into pET-28a to obtain plasmids for expression of respective AARSs. When the primers were designed, an NdeI site and an HindIII site were added for the TyrRS gene so that a His tag was attached to the N-terminus, and an NcoI site and an NotI site were added for the other genes so that a His tag was attached to the C-terminus.

For the heterogenous expression of IleRS, MetRS, and TyrRS derived from the *Thermus thermophilus* HB8 strain (SEQ ID NOS: 37 to 39) in *Escherichia coli*, a *Thermus thermophilus* gene expression plasmid set provided by RIKEN BioResource Center, DNA Bank was used.

7. Expression and Purification of AARS

The *Escherichia coli* BL21 (DE3) strain was transformed with each of the expression plasmids, and used as overexpression strains. Each expression strain was cultured at 37° C. with shaking until $OD_{600}$ became 0.6 to 0.8, and the expression was induced by adding IPTG at a final concentration of 0.5 mM. After the induction of expression, each strain was cultured at 30° C. for 4 hours with shaking, and the cells were collected. The cells were disrupted by ultrasonication, and the subject enzyme was obtained in a soluble fraction.

The supernatant of the cell disruption suspension of each expression strain was loaded on a Ni Sepharose column produced by GE Healthcare, washed with a 20 mM Tris-HCl, 50 mM imidazole solution, and eluted with the 20 mM Tris-HCl, 500 mM imidazole solution to purify and collect the subject enzyme. The enzyme solution was subjected to dialysis or ultrafiltration to eliminate imidazole, or change or concentrate the buffer, if needed, and then used.

8. Method for Measuring AARS Activity with Coupled PPDK and LDH

A test sample containing an amino acid as the measurement subject and a reaction mixture for quantifying amino acid having the following composition were mixed. The mixture was left standing at 30° C. to allow the AARS, PPDK, and LDH reactions to advance, and decrease of the absorbance at 340 nm was measured. The volume of the mixture was 200 µl, and after the reaction mixture was put into the wells of a 96-well microplate, the absorbance was measured with a microplate reader.

Reaction mixture for quantifying amino acid: 20 mM Tris-HCl (pH 7.0), 10 mM $MgCl_2$, 10 mM $NH_4Cl$, 0.3 mM PEP, 0.3 mM NADH, 0.2 mM ATP, 0.2 mM AMP, 70 mU/ml PPDK, 50 U/ml LDH, and AARS (concentrations are final concentrations obtained after mixing with test sample)

9. Method for Measuring AARS Activity Based on Molybdenum Blue Reaction

A test sample containing an amino acid as the measurement subject and a reaction mixture for quantifying amino acid having the following composition were mixed. The mixture was left standing at 30° C. to allow the AARS reaction to advance. The mixture in a volume of 33 µl, 66 µl of water, and 1 µl of a 300 U/ml yeast pyrophosphatase solution were mixed, and left standing at room temperature for 20 minutes to allow the pyrophosphatase reaction to advance. Then, the reaction mixture was mixed with 100 µl of a color development solution A and 30 µl of a color developing solution B having the following compositions, then the mixture was left standing at room temperature for 5 minutes, and the absorbance was measured at 700 nm or 900 nm with a microplate reader.

Reaction mixture for quantifying amino acid: 20 mM Tris-HCl (pH 7.0), 5 mM $MgCl_2$, 2 mM ATP, and AARS (concentrations are final concentrations obtained after mixing with test sample)

Color developing solution A: A solution obtained by mixing water and concentrated sulfuric acid at a ratio of 3:1 and dissolving $(NH_4)_6Mo_7O_{24} \cdot 4H_2O$ in the mixture at a concentration of 0.066 g/ml Color developing solution B: A solution obtained by mixing water and concentrated sulfuric acid at a ratio of 10000:7 and dissolving $FeSO_4 \cdot 7H_2O$ in the mixture at a concentration of 145 mg/ml 10. Method for Measuring AARS Activity at 70° C.

A test sample containing an amino acid as the measurement subject and a reaction mixture for quantifying amino acid having the following composition were mixed. The mixture was left standing at 70° C. to allow the AARS reaction to advance. The mixture in a volume of 600 µl, 60 µl of a 1 M 2-mercaptoethanol solution, and 240 µl of the color development solution mentioned below were mixed, then the mixture was left standing at room temperature for 20 minutes, and the absorbance was measured at 580 nm in a cuvette having an optical path length of 1 cm.

Reaction mixture for quantifying amino acid: 20 mM HEPES-NaOH (pH 8.0), 5 mM $MgCl_2$, 0.5 mM ATP, and AARS (concentrations are final concentrations obtained after mixing with test sample)

Color developing solution: A solution obtained by mixing water and concentrated sulfuric acid at a ratio of 6:1 and dissolving $(NH_4)_6Mo_7O_{24} \cdot 4H_2O$ in the mixture at a concentration of 0.025 g/ml 11. Verification of Effect of Addition of Hydroxylamine The AARS activity was measured with adding hydroxylamine to the reaction mixture at various concentrations by using the AARS activity measurement method described in 8. As AARS, TyrRS derived from *Thermotoga* was used. As test samples, standard Tyr solutions giving final concentrations of 0, 25, 50, 100, and 150 μM after mixing with a test sample were used. Hydroxylamine was added to the reaction mixture at final concentrations of 0, 50, 100, 200, 400, 600, 800, and 1000 mM after mixing with a test sample. Hydroxylamine used in this example and the following examples was hydroxylamine neutralized beforehand to pH 7.0 by addition of hydrochloric acid. TyrRS was added to the reaction mixture at a final concentration of 125 μg/ml (10 mU/ml). The test samples and the reaction mixture containing Tyr and hydroxylamine at various concentrations were mixed, and then promptly set on a microplate reader, and monitoring of the absorbance at 340 nm was started. For the sample groups of the various hydroxylamine concentration conditions, absorbance differences were calculated with respect to that of 0 mM Tyr sample were calculated and plotted. As a result, such change thereof over time as shown in FIG. 10 was obtained.

50, 100, 200, 400, 600, and 800 mM of hydroxylamine was added, and Tyr concentration-dependent change of the absorbance was observed, which is considered to be induced by the coupled AARS, PPDK and LDH reactions. These reactions continued for 5 minutes to 1 hour or more after mixing of the sample, and thereafter the absorbance difference settled at a certain constant level. As for the samples for which 400 mM or lower of hydroxylamine was used, a higher hydroxylamine concentration gave a shorter time until the absorbance difference settled to a constant level. As for the samples for which more than 400 mM of hydroxylamine was used, significant difference was not observed for the time until the absorbance difference settled to a constant level.

On the other hand, when hydroxylamine is not added, the absorbance change considered to be induced by coupled TyrRS, PPDK and LDH reactions was not observed. Under this condition, the differences of absorbance values of the samples were small, and they were within the order of difference caused by contamination on wells of microplate or experimental errors. Therefore, it was demonstrated that addition of hydroxylamine is indispensable for observing advance of the TyrRS reaction by using the aforementioned detection system.

The condition of not adding hydroxylamine used in this example is based on the same principle as that of the reaction conditions used in Japanese Patent Unexamined Publication (Kokai) No. 2008-86312 and Japanese Patent Unexamined Publication (Kokai) No. 8-336399.

In spite of use of the similar conditions, significant pyrophosphate generation by the AARS reaction was detected in the above patent documents, whereas it could not be detected in this example. Although the cause of this difference of the results is unknown, it may be partly caused by the difference of the detection methods. That is, the detection was performed by the absorbance method in this example, whereas the detection was performed by the sensor electrode method or fluorescence method in the aforementioned patent documents, and whether the detection is possible or not may differ by the difference in the sensitivities of the detection methods. Anyway, the result of this example demonstrated that, at least in the case of using such a detection system as used in this example, pyrophosphate generation by the AARS reaction that is undetectable with no addition of hydroxylamine can be made detectable by addition of hydroxylamine.

Figure 11:
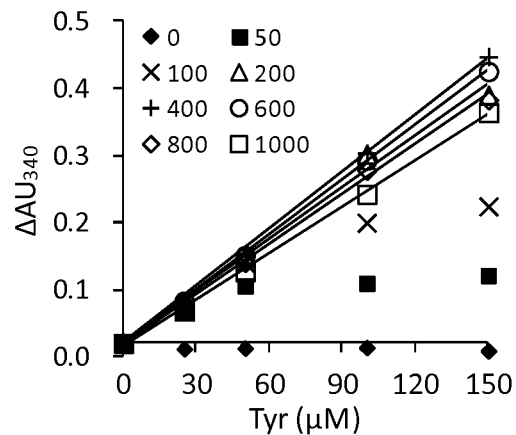
FIG. 11 shows Tyr calibration curves created from the measured values obtained 20 minutes after the start of the measurement. The numbers in the graph (0, 50, 100, 200, 400, 600, 800, and 1000) represent hydroxylamine concentrations (mM) for the respective calibration curves. For the results obtained for the samples containing 200, 400, 600, 800, and 1000 mM hydroxylamine, primary approximate lines are also drawn.

Calibration curves for various hydroxylamine concentrations prepared by plotting the data shown in FIG. 10 along a vertical axis indicating absorbance difference observed 20 minutes after the measurement and a horizontal axis indicating Tyr concentration are as shown in FIG. 11. For the conditions of hydroxylamine concentrations of 200, 400, 600, 800, and 1000 mM, the correlation coefficients of the absorbance difference and the Tyr concentration are 0.9952, 0.9998, 0.9998, 0.9988, and 0.9995, respectively. It can be said that all the calibration curves have high linearity, and it was demonstrated that this reaction system enables highly precise Tyr quantification.

Figure 12:
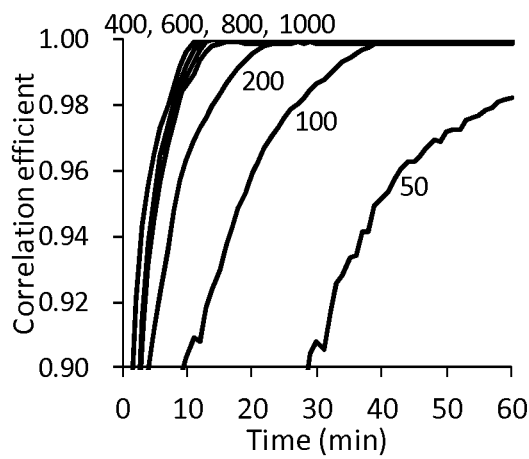
FIG. 12 shows temporal change of the correlation coefficient for Tyr concentration and absorbance difference. The numbers in the graph (0, 50, 100, 200, 400, 600, 800, and 1000) represent hydroxylamine concentrations (mM).
Figure 13:
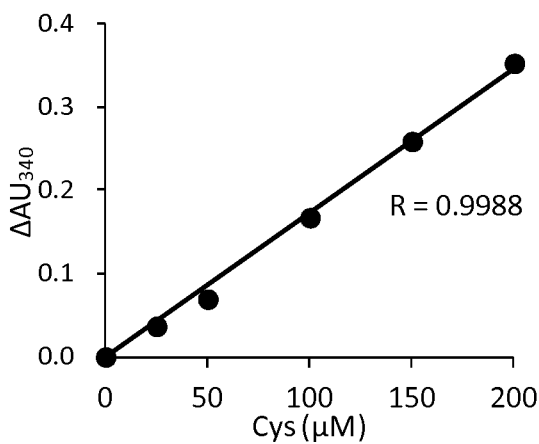
FIG. 13 shows a Cys calibration curve obtained by using CysRS derived from *Thermotoga*.
Figure 14:
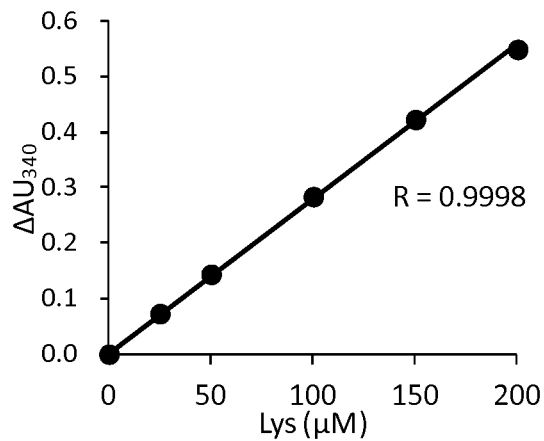
FIG. 14 shows a Lys calibration curve obtained by using LysRS derived from *Thermotoga*.
Figure 15:
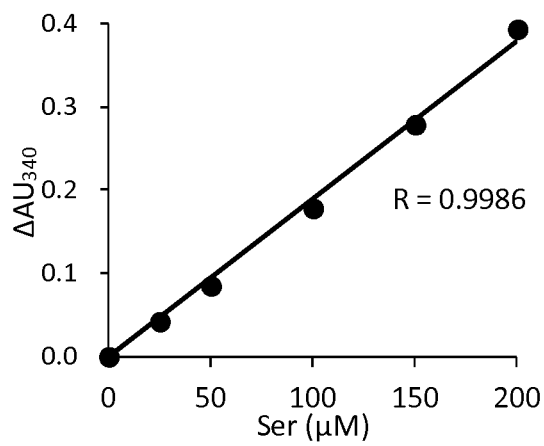
FIG. 15 shows a Ser calibration curve obtained by using SerRS derived from *Thermotoga*.
Figure 16:
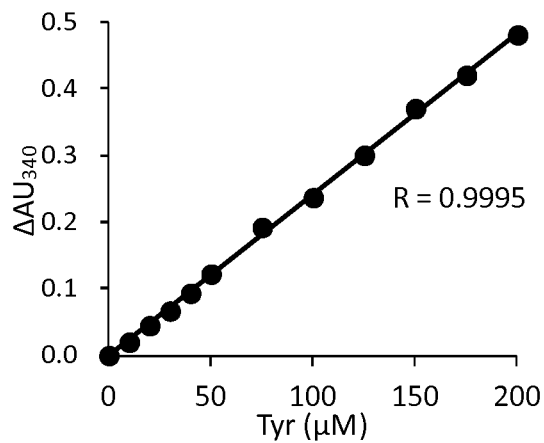
FIG. 16 shows a Tyr calibration curve obtained by using TyrRS derived from *Thermotoga*.

Calibration curves were similarly prepared for time points other than 20 minutes after the measurement, and the correlation coefficients were calculated. The result of plotting the correlation coefficients along a horizontal axis indicating time is as shown in FIG. 12. For all the hydroxylamine concentrations, there was observed a tendency that the correlation coefficient stably increases over time. As for the samples for which 400 mM or lower of hydroxylamine was used, a higher hydroxylamine concentration gave a shorter time until the correlation coefficient was stabilized, and as for the samples for which higher concentration of hydroxylamine was used, significant difference was not observed. Thus, it was demonstrated that if the system is not adversely affected by hydroxylamine of high concentration, by adding hydroxylamine at a higher concentration, the reaction can be completed more quickly.

12. Preparation of Calibration Curve for Quantification of Amino Acid by Coupled PPDK and LDH Calibration curves were prepared by using the AARS activity measurement method described in 8. and standard Cys, Lys, Ser, and Tyr solutions as test samples. The concentrations of the aforementioned amino acids were set so that the final concentrations thereof are in the range of 0 to 200 μM. The hydroxylamine concentration was 200 mM for the samples used for the Tyr calibration curve, or 1000 mM for the samples used for the Cys, Lys, and Ser calibration curves. The *Thermotoga*-derived CysRS, LysRS, SerRS, TyrRS, and the *Thermus*-derived TyrRS were added to the reaction mixture at final concentrations of 0.2 (7 mU/ml), 0.1 (10 mU/ml), 0.2 (8 mU/ml), 0.4 (40 mU/ml), and 0.1 mg/ml, respectively.

When the *Thermotoga*-derived AARSs were used, the calibration curves shown in FIGS. 13 to 16 were obtained for the amino acids. It was shown that all the calibration curves have high linearity. By these results, it was demonstrated that, not only Tyr, but also Cys, Lys, and Ser can be quantified by this quantification method. When hydroxylamine was not added, significant absorbance change was not observed in all the reaction mixtures.

Calibration curves could be similarly prepared when adding pyrophosphate instead of the aforementioned amino acids, but the inclinations of the Lys, Ser, and Tyr calibration curves (absorbance change per mM of substrate) were 80% or more of the inclination of the pyrophosphate calibration curve. This indicates that 80% or more of the amino acids in the test samples were used for the reaction, and the same molar number of pyrophosphate was generated. The inclination of the Cys calibration curve was slightly smaller than those of the other calibration curves, and it is considered that this is because a part of cysteine in the test sample was converted into cystine by air oxidation, and the real concentration of cysteine was reduced.

Figure 17:
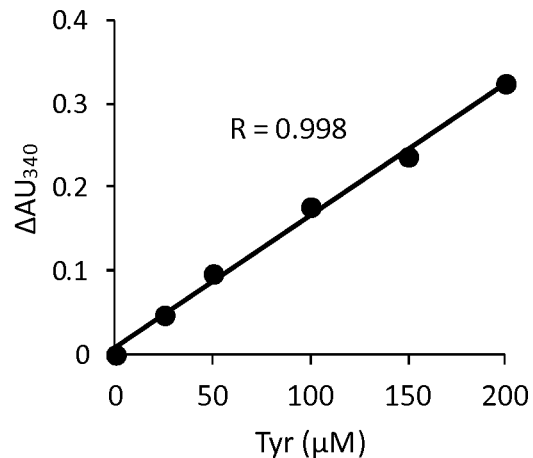
FIG. 17 shows a Tyr calibration curve obtained by using TyrRS derived from *Thermus*.

Further, when the *Thermus*-derived TyrRS was used, the calibration curve as shown in FIG. 17 was obtained. Such a calibration curve of high linearity was obtained as in the case of using the *Thermotoga*-derived TyrRS, and thus it was demonstrated that the quantification is enabled with AARS derived from an organism other than *Thermotoga*.

13. Preparation of Calibration Curve for Quantification of Amino Acid Based on Molybdenum Blue Method Calibration curves were prepared by using the AARS activity measurement method described in 9. and standard His, Pro, and Trp solutions as test samples. The concentrations of the aforementioned amino acids were set so that the final concentrations thereof are in the range of 0 to 80 µM. HisRS, ProRS, and TrpRS were added to the reaction mixture at final concentrations of 0.1, 0.2, and 0.1 mg/ml, respectively.

Figure 18:
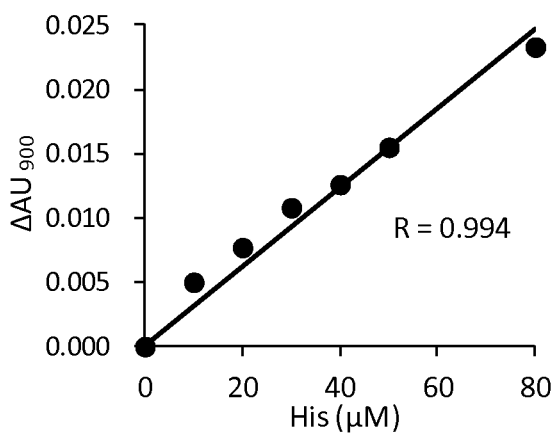
FIG. 18 shows a His calibration curve obtained by using the molybdenum blue method.
Figure 19:
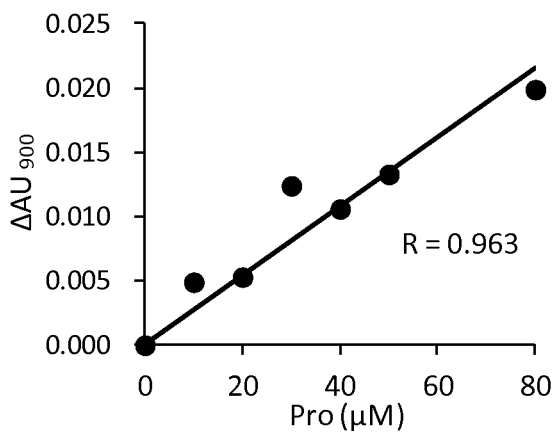
FIG. 19 shows a Pro calibration curve obtained by using the molybdenum blue method.
Figure 20:
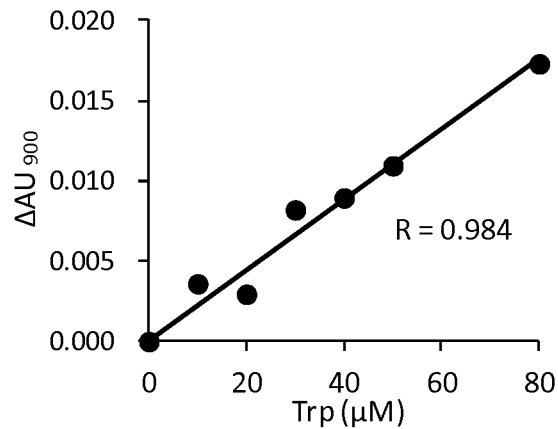
FIG. 20 shows a Trp calibration curve obtained by using the molybdenum blue method.

Such calibration curves as shown in FIGS. 18 to 20 were obtained for the amino acids. Since samples containing amino acids at a low concentration close to the detection limit were used, the correlation coefficients are inferior to those of the systems of which results are shown in FIGS. 13 to 16, but the calibration curves shows such linearity that the curves can be used as calibration curves. Therefore, it was demonstrated that His, Pro, and Trp can also be quantified by this quantification method, and the quantification is enabled even by using a method other than the method for quantifying pyrophosphate described in 8. When hydroxylamine was not added, significant absorbance change was observed for all the reaction mixtures.

14. Preparation of Calibration Curve for Quantification of Amino Acid at 70° C.

Calibration curves were prepared by using the AARS activity measurement method described in 10. and standard Ile, Met, and Tyr solutions as test samples. As AARS, the *Thermus*-derived IleRS, MetRS, and TyrRS were used. These AARSs were added to the reaction mixture at final concentrations of 0.01, 0.08, and 0.08 mg/ml, respectively. The concentrations of the aforementioned amino acids were set so that the final concentrations thereof were in the range of 0 to 100 µM. Further, as the complex decomposition reagent, hydroxylamine was added at a final concentration of 400 mM.

Figure 21:
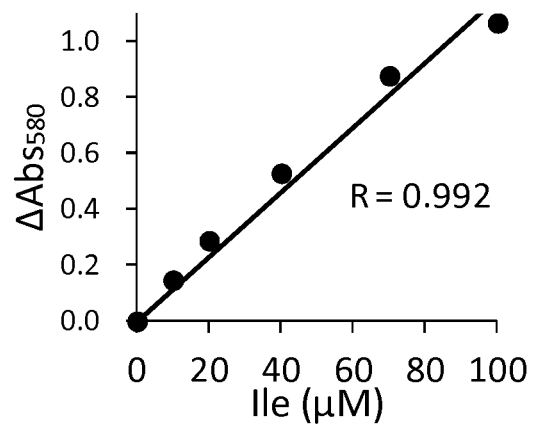
FIG. 21 shows an Ile calibration curve obtained by using IleRS derived from *Thermus* and performing the reaction at 70° C.
Figure 22:
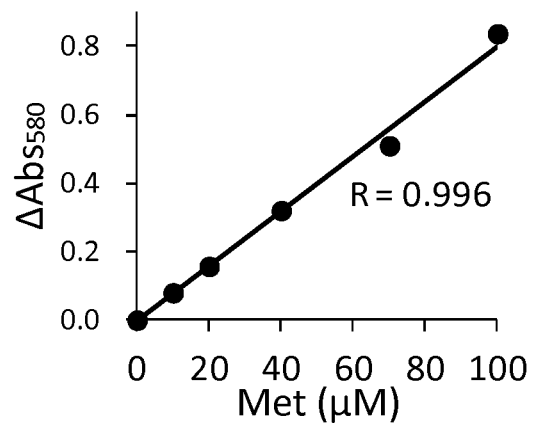
FIG. 22 shows a Met calibration curve obtained by using MetRS derived from *Thermus* and performing the reaction at 70° C.
Figure 23:
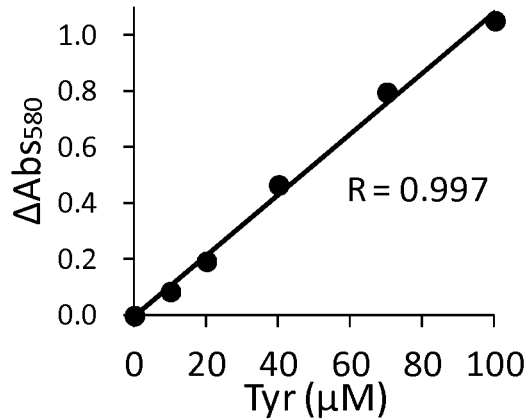
FIG. 23 shows a Tyr calibration curve obtained by using TyrRS derived from *Thermus* and performing the reaction at 70° C.

Such calibration curves as shown in FIGS. 21 to 23 were obtained for the amino acids. This result revealed that Ile and Met can also be quantified by this quantification method. Further, it was also simultaneously revealed that the reaction temperature in the step A is not limited to 30° C., but it can be set to be a high temperature such as 70° C. Furthermore, in the case of the *Thermus*-derived TyrRS, the quantification was enabled with an enzyme concentration 1 order lower than that used in the method described in 11., wherein the reaction was performed at 30° C. Hence, AARS derived from a thermophile has an advantage that the amount of the enzyme to be used can be reduced by performing the reaction at a high temperature such as 70° C.

15. Substrate Specificity of AARS

Presence or absence of pyrophosphate generation was verified for the *Thermotoga*-derived CysRS, HisRS, LysRS, ProRS, SerRS, TrpRS, and TyrRS by using the AARS activity measurement method described in 9. and standard solutions of the various amino acids as test samples. AARSs were added to the reaction mixture at final concentrations of 0.3 (8 mU/ml), 0.1, 0.2 (3 mU/ml), 0.2, 0.1 (1 mU/ml), 0.1, 0.2 (20 mU/ml) mg/ml, respectively. The reaction mixtures were prepared so that the final concentration of Tyr was 1 mM, and the final concentrations of the other amino acids were 5 mM. As for the hydroxylamine concentration, it was added at a final concentration of 1000 mM for all the cases. Further, presence or absence of pyrophosphate production was also verified for the *Thermus*-derived MetRS and TyrRS by using the AARS activity measurement method described in 10. and standard solutions of the various amino acids as test samples. The reaction mixtures were prepared so that the final concentrations of the amino acids were 200 µM. Hydroxylamine was added at a final concentration of 400 mM.

Detection or no detection of the activity in the reaction mixtures containing a combination of each AARS and amino acid are shown in Table 2. The symbol + indicates detection of the activity, and − indicates no detection of the activity. Each AARS exhibited activity for only one corresponding amino acid. From these results, it was revealed that highly selective quantification of each amino acid species is enabled with a quantification system using any of these AARSs.

TABLE 2

Table 2: Qualitative test for various AARSs

| | *Thermotoga*-derived AARS | | | | | | | *Thermus*-derived AARS | |
|---|---|---|---|---|---|---|---|---|---|
| | CysRS | HisRS | LysRS | ProRS | SerRS | TrpRS | TyrRS | MetRS | TyrRS |
| Ala | − | − | − | − | − | − | − | − | − |
| Cys | + | − | − | − | − | − | − | − | − |
| Asp | − | − | − | − | − | − | − | − | − |
| Glu | − | − | − | − | − | − | − | − | − |
| Phe | − | − | − | − | − | − | − | − | − |
| Gly | − | − | − | − | − | − | − | − | − |
| His | − | + | − | − | − | − | − | − | − |
| Ile | − | − | − | − | − | − | − | − | − |
| Lys | − | − | + | − | − | − | − | − | − |
| Leu | − | − | − | − | − | − | − | − | − |
| Met | − | − | − | − | − | − | − | + | − |
| Asn | − | − | − | − | − | − | − | − | − |
| Pro | − | − | − | + | − | − | − | − | − |
| Gln | − | − | − | − | − | − | − | − | − |
| Arg | − | − | − | − | − | − | − | − | − |
| Ser | − | − | − | − | + | − | − | − | − |
| Thr | − | − | − | − | − | − | − | − | − |

TABLE 2-continued

Table 2: Qualitative test for various AARSs

| | Thermotoga-derived AARS | | | | | | | Thermus-derived AARS | |
|---|---|---|---|---|---|---|---|---|---|
| | CysRS | HisRS | LysRS | ProRS | SerRS | TrpRS | TyrRS | MetRS | TyrRS |
| Val | − | − | − | − | − | − | − | − | − |
| Trp | − | − | − | − | − | + | − | − | − |
| Tyr | − | − | − | − | − | − | + | − | + |

+ . . . Activity was detected, − . . . Activity was not detected

16. Effect of Various Complex Decomposition Reagents

Calibration curves were prepared by using the AARS activity measurement method described in 10. and adding hydrazine or methylamine as the complex decomposition reagent. As AARS, the *Thermus*-derived TyrRS was added to the reaction mixture at a final concentration of 0.01 mg/ml. Tyr concentration was adjusted so as to give a final concentration of 0 to 100 µM. Further, hydrazine and methylamine were added at final concentrations of 400 mM and 20 mM, respectively.

Figure 24:
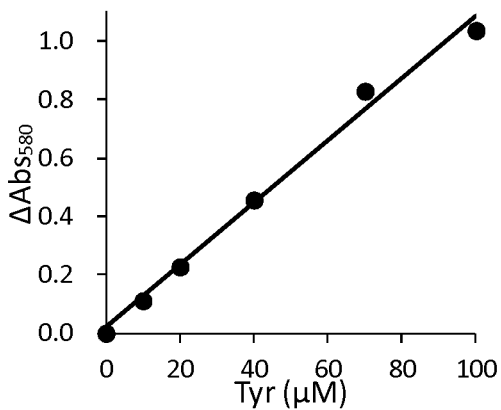
FIG. 24 shows a Tyr calibration curve obtained by using hydrazine as the complex decomposition reagent.
Figure 25:
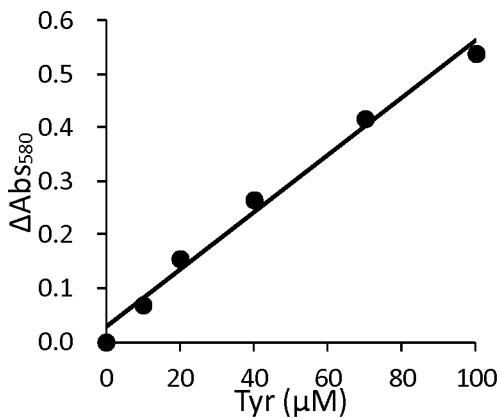
FIG. 25 shows a Tyr calibration curve obtained by using methylamine as the complex decomposition reagent.

Calibration curves were prepared for the complex decomposition reagents by plotting absorbance differences observed 20 minutes after the measurement along the vertical axis and Tyr concentration along the horizontal axis. The calibration curves prepared by using hydrazine and methylamine are shown in FIGS. 24 and 25, respectively. It can be said that both have high linearity as a calibration curve, and it was demonstrated that this reaction system enables highly precise quantification of amino acids.

INDUSTRIAL APPLICABILITY

Methionine, citrulline and arginine are important amino acid species in the living body, and are also important constituents contained in foods and drugs. Methionine is one of the essential amino acids, and it is known to have effects of reducing blood cholesterol or histamine and eliminating active oxygen, but extensive administration thereof also causes fatty liver. Citrulline is known to contribute to blood flow promotion, immune activation, etc., and is widely used in foods and drugs such as supplements, because of the efficacies thereof. Arginine is a semi-essential amino acid of which intake is necessary during growth, and is used in foods and drugs for improvement of immune activity or recovery from fatigue. Therefore, quantification of these amino acids would be useful in food analysis, quality control of drugs and supplements, blood test of excess symptom and deficiency, and enzyme sensing.

Further, it is known that methionine accumulates in homocystinuria patients at high concentration, and methionine clinically serves as an important biomarker for mass screening of such patients. Further, citrulline and arginine are metabolites in the urea cycle, and serve as a biomarker of metabolic abnormalities in the urea cycle including citrullinuria or arginase deficiency. Therefore, use of quantification of these amino acids as simple and convenient mass screening for detection of such diseases as mentioned above is also expected.

Amino acid analysis is used for quality control of foods and detection of markers of various diseases, and it considered a technique in demand in a wide range of industrial fields. In order to conduct amino acid analysis for multiple kinds of amino acids, there is substantially only a single choice of using analytical instruments for HPLC etc. at present. However, such instrumental analysis requires expensive and large-scale analytical instruments, and it is difficult to thereby perform quick on-site analysis. Further, when the measurement is not performed on site, but such analysis is entrusted to outside organizations, analysis, transport and storage of samples can be very expensive, and hence limiting in such use.

Unlike such instrumental analysis methods as mentioned above, the methods of the present invention are enzymatic quantification methods, and do not require any expensive analytical instrument for exclusive use. Further, also unlike the conventional enzymatic quantification methods that require highly sensitive detection systems, such as use of radioisotope or the fluorescence method, the methods of the present invention can be easily used in a wide range of environments. By performing the methods of the present invention, many kinds of amino acids can be quickly measured. For example, by mixing an AARS activity measurement solution and a test sample, then dividing the mixture, and mixing different kinds of AARSs with the divided portions of the mixture, simultaneous quantification of many kinds of amino acids can be easily performed. Moreover, it is also demonstrated in the examples of this specification that the methods of the present invention can be performed with a high throughput measurement equipment such as microplate reader.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

Sequence Listing Free Text
SEQ ID NO: 1, PfPPDK gene sequence
SEQ ID NO: 2, Primer sequence
SEQ ID NO: 3, Primer sequence
SEQ ID NO: 4, TtPPDK gene sequence
SEQ ID NO: 5, Primer sequence
SEQ ID NO: 6, Primer sequence
SEQ ID NO: 7, AdoMetS gene sequence
SEQ ID NO: 8, Primer sequence
SEQ ID NO: 9, Primer sequence
SEQ ID NO: 10, ASS gene sequence
SEQ ID NO: 11, Primer sequence
SEQ ID NO: 12, Primer sequence
SEQ ID NO: 13, ADI gene sequence
SEQ ID NO: 14, Primer sequence
SEQ ID NO: 15, Primer sequence
SEQ ID NO: 16, *Thermotoga*-derived CysRS
SEQ ID NO: 17, *Thermotoga*-derived HisRS
SEQ ID NO: 18, *Thermotoga*-derived LysRS
SEQ ID NO: 19, *Thermotoga*-derived ProRS
SEQ ID NO: 20, *Thermotoga*-derived SerRS
SEQ ID NO: 21, *Thermotoga*-derived TrpRS SEQ ID NO: 22, *Thermotoga*-derived TyrRS
SEQ ID NO: 23, Primer CysRS F
SEQ ID NO: 24, Primer CysRS R
SEQ ID NO: 25, Primer H is RS F
SEQ ID NO: 26, Primer H is RS R
SEQ ID NO: 27, Primer LysRS F
SEQ ID NO: 28, Primer LysRS R
SEQ ID NO: 29, Primer ProRS F
SEQ ID NO: 30, Primer ProRS R
SEQ ID NO: 31, Primer SerRS F
SEQ ID NO: 32, Primer SerRS R
SEQ ID NO: 33, Primer TrpRS F
SEQ ID NO: 34, Primer TrpRS R
SEQ ID NO: 35, Primer TyrRS F
SEQ ID NO: 36, Primer TyrRS R
SEQ ID NO: 37, *Thermus*-derived IleRS
SEQ ID NO: 38, *Thermus*-derived MetRS
SEQ ID NO: 39, *Thermus*-derived TyrRS

The invention claimed is:

1. A method for quantifying an amino acid, which comprises:
 (A) reacting an aminoacyl-tRNA synthetase (AARS) corresponding to the amino acid with the amino acid and adenosine triphosphate (ATP) in the presence of an (aminoacyl-adenosine monophosphate (AMP))-AARS complex decomposition reagent to generate pyrophosphate, wherein the AARS is regenerated in free form via decomposition of a formed (aminoacyl-AMP)-AARS complex,
 (B) quantifying the pyrophosphate generated in (A) by a method comprising reacting pyrophosphate dikinase (PPDK) with the generated pyrophosphate in the presence of AMP and phosphoenolpyruvate (PEP) to generate ATP, phosphoric acid, and pyruvate, and
 (C) quantifying the generated pyruvate;
 wherein the amount of the amino acid is determined based on the amount of pyruvate,
 and wherein said method is performed in the absence of tRNA.

2. The method according to claim 1, wherein the complex decomposition reagent is an amine or carbanion.

3. The method according to claim 2, wherein the complex decomposition reagent is selected from the group consisting of hydroxylamine, hydrazine, and methylamine.

4. The method according to claim 1, further comprising the steps of, prior to said (A):
 a) preparing AARSs corresponding to the respective amino acids to be quantified,
 b) preparing a reaction reagent containing required components other than AARSs,
 c) mixing the reaction reagent and the sample,
 d) dividing the mixture into a number of portions at least corresponding to the two or more kinds of amino acids to be quantified, and
 e) adding different AARSs to the divided portions, respectively.

5. The method according to claim 1, wherein AARS is derived from a thermophile, and (A) is performed at a temperature of 50° C. or higher.

6. The method according to claim 1, wherein the step of quantifying the generated pyruvate comprises reacting (i) lactate dehydrogenase, (ii) pyruvate oxidase, (iii) pyruvate decarboxylase and alcohol dehydrogenase, or (iv) pyruvate decarboxylase and aldehyde dehydrogenase with pyruvate.

7. The method according to claim 1, wherein the amino acid is present in a sample containing adenosine triphosphate (ATP) or phosphoric acid.

8. The method according to claim 7, wherein the sample is derived from blood.

* * * * *